US009833433B1

(12) United States Patent
Chen et al.

(10) Patent No.: US 9,833,433 B1
(45) Date of Patent: Dec. 5, 2017

(54) COMPOSITIONS, METHODS OF USE, AND METHODS OF TREATMENT

(71) Applicant: Board of Supervisors of Louisiana State University and Agricultural and Mechanical College, Baton Rouge, LA (US)

(72) Inventors: Chu Chen, Harvey, LA (US); Jian Zhang, Harvey, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/672,817

(22) Filed: Aug. 9, 2017

Related U.S. Application Data

(62) Division of application No. 15/033,141, filed as application No. PCT/US2014/063118 on Oct. 30, 2014, now Pat. No. 9,763,912.

(60) Provisional application No. 61/897,344, filed on Oct. 30, 2013.

(51) Int. Cl.
| | | |
|---|---|---|
| A61K 31/352 | (2006.01) | |
| A61K 31/365 | (2006.01) | |
| A61K 31/415 | (2006.01) | |
| A61K 31/616 | (2006.01) | |
| A61K 45/06 | (2006.01) | |

(52) U.S. Cl.
CPC .......... *A61K 31/352* (2013.01); *A61K 31/365* (2013.01); *A61K 31/415* (2013.01); *A61K 31/616* (2013.01); *A61K 45/06* (2013.01)

(58) Field of Classification Search
CPC .. A61K 31/352; A61K 31/365; A61K 31/415; A61K 31/616; A61K 45/06
USPC ........................................................ 514/406
See application file for complete search history.

(56) References Cited

U.S. PATENT DOCUMENTS

| | | |
|---|---|---|
| 8,222,292 B2 | 7/2012 | Goskonda et al. |
| 8,410,064 B2 | 4/2013 | Radominska-Pandya et al. |
| 2005/0063909 A1 | 3/2005 | Wright, IV et al. |
| 2009/0117197 A1 | 5/2009 | Bascomb et al. |
| 2010/0159001 A1 | 6/2010 | Cardinal et al. |

OTHER PUBLICATIONS

Sang, N., Zhang, J., Marcheselli, V., Bazan, N. G., and Chen, C. (2005). Postsynaptically synthesized prostaglandin E2 modulates hippocampal synaptic transmission via a presynaptic PGE2 EP2 receptor. J. Neurosci. 25, 9858-9870.

Sanzgiri, R.P., Araque, A., Haydon, P.G. (1999). Prostaglandin E(2) stimulates glutamate receptor-dependent astrocyte neuromodulation in cultured hippocampal cells. J. Neurobiol. 41, 221-229.
Solowij, N., Stephens, R.S., Roffman, R.A., Babor, T., Kadden, R., Miller, M., Christiansen, K., McRee, B., and Vendetti, J. (2002). Marijuana Treatment Project Research Group.. Cognitive functioning of long-term heavy cannabis users seeking treatment. J. Am. Med. Assoc. 287, 1123-1131.
Suárez, I., Bodega, G., Fernández-Ruiz, J., Ramos, J.A., Rubio, M., and Fernández, B. (2003). Down-regulation of the AMPA glutamate receptor subunits GluR1 and GluR2/3 in the rat cerebellum following pre- and perinatal Δ9-tetrahydrocannabinol exposure. Cerebellum 2, 66-74.
Suárez, I., Bodega, G., Rubio, M., Fernández-Ruiz, J.J., Ramos, J.A., and Fernández, B. (2004). Prenatal cannabinoid exposure down-regulates glutamate transporter expressions (GLAST and EAAC1) in the rat cerebellum. Dev. Neurosci. 26, 45-53.
Teather, L.A., Packard, M.G., and Bazan, N.G. (2002). Post-training cyclooxygenase-2 (COX-2) inhibition impairs memory consolidation. Learn Mem. 9, 41-47.
Tomasini, M.C., Ferraro, L., Bebe, B.W., Tanganelli, S., Cassano, T., Cuomo, V., and Antonelli, T. (2002). Δ9-Tetrahydrocannabinol increases endogenous extracellular glutamate levels in primary cultures of rat cerebral cortex neurons: involvement of CB1 receptor. J. Neurosci. Res. 68, 449-453.
Tonini, R., Ciardo, S., Cerovic, M., Rubino, T., Parolaro, D., Mazzanti, M., and Zippel, R. (2006). ERK-dependent modulation of cerebellar synaptic plasticity after chronic Δ9-tetrahydrocannabinol exposure. J Neurosci. 26, 5810-5818.
Wilson, R.I., Kunos, G., Nicoll, R.A. (2001). Presynaptic specificity of endocannabinoid signaling in the hippocampus. Neuron 31, 453-462.
Yao, L., Fan, P., Jian, Z., Mailliard, W.S., Gordon, A.S., and Diamond, I. (2003). Addicitng drugs untilize a synergistic molecular mechanism in common requiring adenosine and Gi-βγ dimmers. Proc. Natl. Acad. Sci. USA 100, 14379:14384.
Zhang J., and Chen, C. (2008). Endocannabinoid 2-arachidonoylglycerol protects neurons by limiting COX-2 elevation. J. Biol. Chem. 283, 22601-22611.
Clapp P, Gibson ES, Dell'acqua ML, Hoffman PL. (2010). Phosphorylation regulates removal of synaptic N-methyl-D-aspartate receptors after withdrawal from chronic ethanol exposure. J. Pharmacol. Exp. Ther. 332, 720-729.
Chen, Q., Nakajima, A., Meacham, C. & Tang, Y.P. (2006b). Elevated cholecystokininergic tone constitutes an important molecular/neuronal mechanism for the expression of anxiety in the mouse. Proc. Natl. Acad. Sci. U. S. A. 103, 3881-3886.
Dumitriu D, Rodriguez A, Morrison JH. (2011). High-throughput, detailed, cell-specific neuroanatomy of dendritic spines using microinjection and confocal microscopy. Nat Protoc. 6, 1391-1411.
Feng, Y., Nie, L., Thakur, M.D., Su, Q., Chi, Z., Zhao, Y., and Longmore, G.D. (2010). A multifunctional lentiviral-based gene knockdown with concurrent rescue that controls for off-target effects of RNAi. Genomics Proteomics Bioinformatics 8, 238-245.

(Continued)

Primary Examiner — Yevegeny Valenrod
(74) Attorney, Agent, or Firm — Thomas | Horstemeyer, LLP

(57) ABSTRACT

Embodiments of the present disclosure provide for compositions including an antimicrobial agent, pharmaceutical compositions including the composition or pharmaceutical composition, methods of treating a condition or disease, methods of treatment using compositions or pharmaceutical compositions, and the like.

18 Claims, 22 Drawing Sheets

(56) References Cited

OTHER PUBLICATIONS

LaPlant Q, Vialou V, Covington HE 3rd, Dumitriu D, Feng J, Warren BL, Maze I, Dietz DM, Watts EL, Iñiguez SD, Koo JW, Mouzon E, Renthal W, Hollis F, Wang H, Noonan MA, Ren Y, Eisch AJ, Bolaños CA, Kabbaj M, Xiao G, Neve RL, Hurd YL, Oosting RS, Fan G, Morrison JH, Nestler EJ. (2010). Dnmt3a regulates emotional behavior and spine plasticity in the nucleus accumbens. Nat Neurosci. 13, 1137-1143.
Oakley, H., Cole, S.L., Logan, S., Maus, E., Shao, P., Craft, J., Guillozet-Bongaarts, A., Ohno, M., Disterhoft, J., Van Eldik, L., Berry, R., and Vassar, R. (2006). Intraneuronal β-amyloid aggregates, neurodegeneration, and neuron loss in transgenic mice with five familial Alzheimer's disease mutations: potential factors in amyloid plaque formation. J. Neurosci. 26, 10129-10140.
Pertwee, R.G. & Wickens, A.P. (1991). Enhancement by chlordiazepoxide of catalepsy induced in rats by intravenous or intrapallidal injections of enantiomeric cannabinoids. Neuropharmacol 30, 237-244.
Rodriguez, A., Ehlenberger, D.B., Hof, P.R., Wearne, S.L. (2006). Rayburst sampling, an algorithm for automated three-dimensional shape analysis fromlaser scanning microscopy images. Nat. Protoc. 1, 2152-2161.
International Search Report for PCT/US2014/063118 dated Feb. 17, 2015.
Chen, et al., "D9-THC-Caused Synaptic and Memory Impairments Are Mediated through COX-2 Signaling", Cell 155, 1154-1165, Nov. 21, 2013.
Saito et al. "Cannabinoid Modulation of Neuroinnammatory Disorders," Curr Neuropharmacol, Jun. 1, 2012 (Jun. 1, 2012), vol. 10, pp. 159-166.
Alger, B.E. (2009). Endocannabinoid signaling in neural plasticity. Curr Top Behav Neurosci 1, 141-172.
Akaneya Y, Tsumoto T. (2006). Bidirectional trafficking of prostaglandin E2 receptors involved in long-term potentiation in visual cortex. J. Neurosci. 26, 10209-10221.
Bahr, B.A., Karanian, D.A., Makanji, S.S., and Makriyannis, A. (2006). Targeting the endocannabinoid system in treating brain disorders. Expert Opin Investig Drugs. 15, 351-365.
Bezzi, P., Carmignoto, G., Pasti, L., Vesce, S., Rossi, D., Rizzini, B.L., Pozzan, T., and Volterra, A. (1998). Prostaglandins stimulate calcium-dependent glutamate release in astrocytes. Nature 391, 281-285.
Brock, T.G., McNish, R.W., and Peters-Golden, M. (1999). Arachidonic acid is preferentially metabolized by cyclooxygenase-2 to prostacyclin and prostaglandin E2. J. Biol. Chem. 274, 11660-11666.
Burstein, S.H., Hull, K., Hunter, S.A., and Shilstone, J. (1989). Immunization against prostaglandins reduced Δ1-tetrohydrocannabinol-induced catalepsy in mice. Mol. Pharmacol. 35, 6-9.
Campbell, V.A., and Gowran, A. (2007). Alzheimer's disease: taking the edge off with cannabinoids? Br. J. Pharmacol. 152, 655-662.
Carlini, E.A. (2004). The good and the bad effects of (-) trans-delta-9-tetrahydrocannabinol (Δ9-THC) on humans. Toxicon 44, 461-467.
Centonze, D., Finazzi-Agro, A., Bernardi, G., and Maccarrone, M. (2007). The endocannabinoid system in targeting inflammatory neurodegenerative diseases. Trends in Pharmacol. Sci. 28, 180-187.
Chen C., Magee, J.C., and Bazan, N.G. (2002). Cyclooxygenase-2 regulates prostaglandin E2 signaling in hippocampal long-term synaptic plasticity. J. Neurophysiol. 87, 2851-2857.
Chen, C., Hardy, M., Zhang, J., LaHoste, G.J., and Bazan, N.G. (2006). Altered NMDA receptor trafficking contributes to sleep deprivation-induced hippocampal synaptic and cognitive impairments. Biochem. Biophys. Res. Commun. 340, 435-440.
Chen, X., Zhang, J., and Chen, C. (2011). Endocannabinoid 2-arachidonoylglycerol protects neurons against β-amyloid insults. Neurosci. 178, 159-168.
Chen, R., Zhang, J., Wu, Y., Wang, D., Feng, G., Tang, Y.P., Teng, Z., and Chen, C. (2012). Monoacylglycerol lipase is a therapeutic target for Alzheimer's disease. Cell Reports 2, 1329-1339.
Chevaleyre, V., Takahashi, K.A., and Castillo, P.E. (2006). Endocannabinoid-Mediated Synaptic Plasticity in the CNS. Ann. Rev. Neurosci 29, 37-76.
Cowley, T.R., Fahey, B., and O'Mara, S.M. (2008). COX-2, but not COX-1, activity is necessary for the induction of perforant path long-term potentiation and spatial learning in vivo. Eur. J. Neurosci. 27, 2999-3008.
Dave, K.A., Platel, J.C., Huang, F., and Tian, D., Stamboulian-Platel, S., Bordey, A. (2010) Prostaglandin E2 induces glutamate release from subventricular zone astrocytes. Neuron Glia Biol. 6, 201-207.
Delaney, A.J., Crane, J.W., and Sah, P. (2007). Noradrenaling modulates transmission at a central synapse by a presynaptic mechanism. Neuron 56, 880-892.
Du, H., Chen, X., Zhang, J., and Chen, C. (2011). Inhibition of COX-2 expression by endocannabinoid 2-arachidonoylglycerol is mediated by PPAR-□. Br. J. Pharmacol. 163, 1533-1549.
Egashira, N., Koushi, E., Mishima, K., Iwasaki, K., Oishi, R., and Fujiwara, M. (2007). 2,5-Dimethoxy-4-iodoamphetamine (DOI) inhibits Delta9-tetrahydrocannabinol-induced catalepsy-like immobilization in mice. J. Pharmacol. Sci. 105, 361-366.
Fairbairn, J.W., and Pickens, J.T. (1979). The oral activity of Δ'-tetrahydrocannabinol and its dependence on prostaglandin E2. Br. J. Pharmacol. 67, 379-385.
Fairbairn, J.W., and Pickens, JT. (1980). The effect of conditions influencing endogenous prostaglandins on the activity of delta'-tetrahydrocannabinol in mice. Br. J. Pharmacol. 69,491-493.
Fan, N., Yang, H., Zhang, J., and Chen, C. (2010). Reduced expression of glutamate receptors and phosphorylation of CREB are responsible for in vivo Δ9-THC exposure-impaired hippocampal synaptic plasticity. J. Neurochem. 112, 691-702.
Ferraro, L., Tomasini, M.C., Gessa, G.L., Bebe, B.W., Tanganelli, S., and Antonelli, T. (2001). The cannabinoid receptor agonist WIN 55,212-2 regulates glutamate transmission in rat cerebral cortex: an in vivo and in vitro study. Cereb. Cortex 11, 728-733.
Gaoni, Y., and Mechoulam, R. (1964). Isolation, structure and partial synthesis of an active constituent of hashish. J. Am. Chem. Soc. 86, 1646-1647.
Goubaeva, F., Ghosh, M., Malik, S., Yang, J., Hinkle, P.M., Griendling, K.K., Neubig R.R., and Smrcka, A.V. (2003). Stimulation of cellular signaling and G protein subunit dissociation by G protein betagamma subunit-binding peptides. J. Biol. Chem. 278, 19634-19641.
Gowran, A., Noonan, J., Campbell, V.A. (2011). The multiplicity of action of cannabinoids: implications for treating neurodegeneration. CNS Neurosci. Ther. 17, 637-644.
Guo, J., and Ikeda, S.R. (2004). Endocannabinoids modulate N-type calcium channels and G-protein-coupled inwardly rectifying potassium channels via CB1 cannabinoid receptors heterologously expressed in mammalian neurons. Mol Pharmacol. 65, 665-674.
Han, J., Kesner, P., Metna-Laurent, M., Duan, T., Xu, L., Georges, F., Koehl, M., Abrous, D.N., Mendizabal-Zubiaga, J., Grandes, P., et al. (2012). Acute cannabinoids impair working memory through astroglial CB1 receptor modulation of hippocampal LTD. Cell 148, 1039-1050.
Hoffman, A.F., Oz. M., Yang, R., Lichtman, A.H., and Lupica, C.R. (2007). Opposing actions of chronic Delta9-tetrahydrocannabinol and cannabinoid antagonists on hippocampal long-term potentiation. Learn. Mem. 14, 63-74.
Howlett, A.C. (1998). The CB1 cannabinoid receptor in the brain. Neurobiol. Dis. 5, 405-416.
Kano, M., Ohno-Shosaku, T., Hashimotodani, Y., Uchigashima, M., and Watanabe, M. (2009). Endocannabinoid-mediated control of synaptic transmission. Physiol. Rev. 89, 309-380.
Li, S., Jin, M., Koeglsperger, T., Shepardson, N.E., Shankar, G.M., Selkoe, D.J. (2011). Soluble Aβ oligomers inhibit long-term potentiation through a mechanism involving excessive activation of extrasynaptic NR2B-containing NMDA receptors. J. Neurosci. 31, 6627-6638.

(56) References Cited

OTHER PUBLICATIONS

Lichtman, A.H., and Martin, B.R. (1996). Delta 9-tetrahydrocannabinol impairs spatial memory through a cannabinoid receptor mechanism. Psychopharm. (Berl) 126,125-131.

Long, J.Z., Nomura, D.K., Vann, R.E., Walentiny, D.M., Booker, L., Jin, X., Burston, J.J., Sim-Selley, L.J., Lichtman, A.H., Wiley, J.L., et al. (2009). Dual blockade of FAAH and MAGL identifies behavioral processes regulated by endocannabinoid crosstalk in vivo. Proc. Natl. Acad. Sci. USA 106, 20270-20275.

Lovinger, D.M. (2008). Presynaptic modulation by endocannabinoids. Handb. Exp. Pharmacol. 184,435-477.

Marchalanta, Y., Brothersa, H.M., and Wenka, G.L. (2008). Inflammation and aging: can endocannabinoids help? Biomed. Pharmacother. 62, 212-217.

Marsicano, G., Goodenough, S., Monory, K., Hermann, H., Eder, M., Cannich, A., Azad, S.C., Cascio, M.G., Gutiérrez, S.O., van der Stelt, M., et al.. (2003). CB1 cannabinoid receptors and on-demand defense against excitotoxicity. Science 302: 84-88.

Mato, S., Chevaleyre, V., Robbe, D., Pazos, A., Castillo, P.E., and Manzoni, O.J. (2004). A single in-vivo exposure to delta 9THC blocks endocannabinoid-mediated synaptic plasticity. Nat. Neurosci. 7, 585-586.

Mato, S., Robbe, D., Puente, N., Grandes, P., and Manzoni, O.J. (2005). Presynaptic homeostatic plasticity rescues long-term depression after chronic Delta 9-tetrahydrocannabinol exposure. J. Neurosci. 25, 11619-11627.

Messinis, L., Kyprianidou, A., Malefaki, S., and Papathanasopoulos, P. (2006). Neuropsychological deficits in long-term frequent cannabis users. Neurol. 66, 737-739.

Monory, K., Blaudzun, H., Massa, F., Kaiser, N., Lemberger, T., Schütz, G., Wotjak, C.T., Lutz, B., and Marsicano, G. (2007). Genetic dissection of behavioural and autonomic effects of Delta (9)-tetrahydrocannabinol in mice. PLoS Biol. 5:e269.

Navarrete, M., and Araque, A. (2008). Endocannabinoids mediate neuron-astrocyte communication. Neuron 57, 883-893.

Panikashvili, D., Simeonidou, C., Ben-Shabat, S., Hanus, L., Breuer, A., Mechoulam, R. and Shohami, E. (2001). An endogenous cannabinoid (2-AG) is neuroprotective after brain injury. Nature 413, 527-531.

Perez-Reyes, M., Burstein, S.H., White, W.R., McDonald, S.A., and Hicks, R.E. (1991). Antagonism of marijuana effects by indomethacin in human. Life Sci. 48, 507-515.

Pertwee, R.G., Howlett, A.C., Abood, M.E., Alexander, S.P., Di Marzo, V., Elphick, M.R., Greasley, P.J., Hansen, H.S., Kunos, G., Mackie, K., et al. (2010). International Union of Basic and Clinical Pharmacology. LXXIX. Cannabinoid receptors and their ligands: beyond $CB_1$ and $CB_2$. Pharmacol. Rev. 62:588-631.

Pope, H.G., Gruber, A.J., Hudson, J.I., Huestis, M.A., and Yurgelun-Todd, D. (2001). Neuropsychological performance in long-term cannabis users. Arch. Gen. Psychiatry 58, 909-915.

Puighermanal, E., Marsicano, G., Busquets-Garcia, A., Lutz, B., Maldonado, R., and Ozaita, A. (2009). Cannabinoid modulation of hippocampal long-term memory is mediated by mTOR signaling. Nat. Neurosci. 12, 1152-1158.

Robson, P. (2001). Therapeutic aspects of cannabis and cannabinoids. Br. J. Psychiatry 178, 107-115.

Rubino, T., Realini, N., Braida, D., Guidi, S., Capurro, V., Viganò, D., Guidali, C., Pinter, M., Sala, M., Bartesaghi, R., et al. (2009). Changes in hippocampal morphology and neuroplasticity induced by adolescent THC treatment are associated with cognitive impairment in adulthood. Hippocampus 19, 763-772.

Russo, E. B. (2007). History of Cannabis and Its Preparations in Saga, Science, and Sobriquet. Chem. Biodiv. 4, 1614-1648.

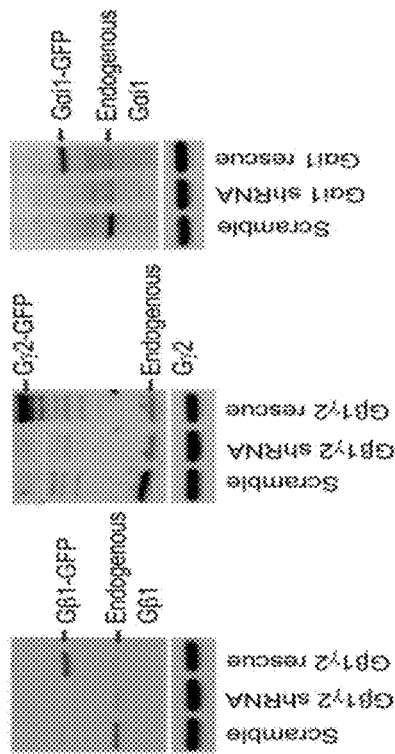
*Fig. 9C*
*Fig. 9D*
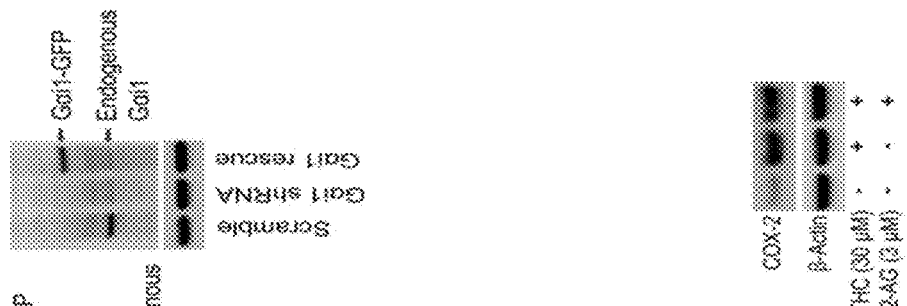
*Fig. 9E*
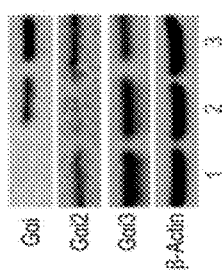
*Fig. 9F*
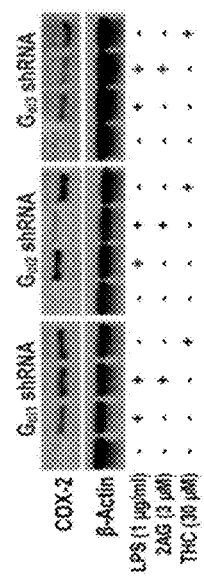
*Fig. 9G*
*Fig. 9I*
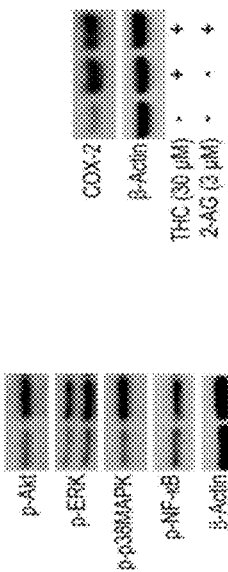
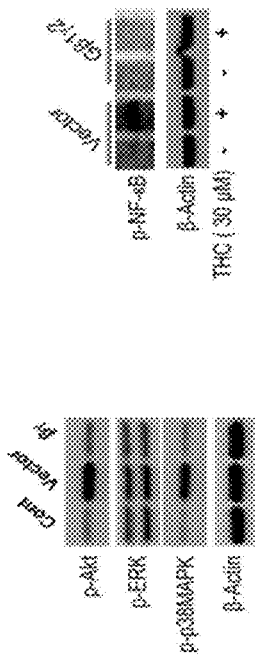
*Fig. 9H*

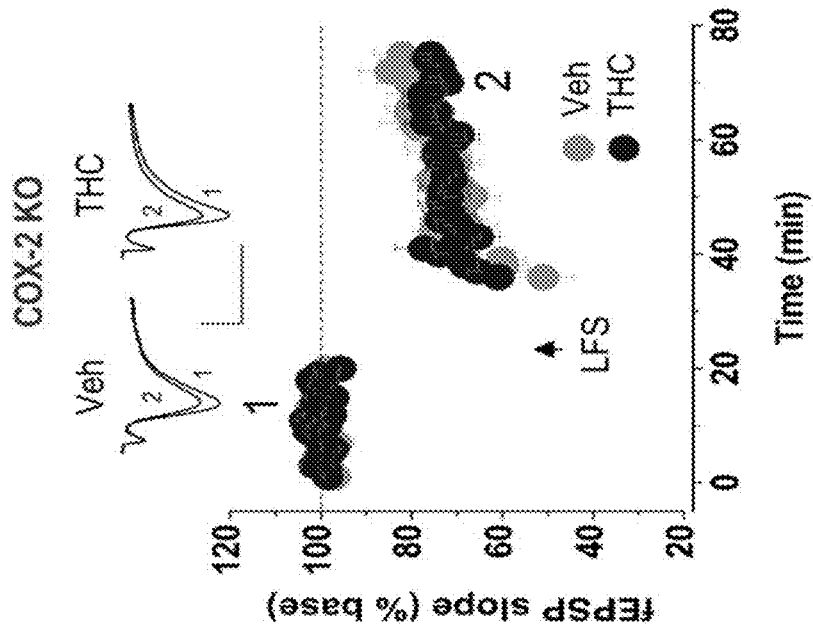
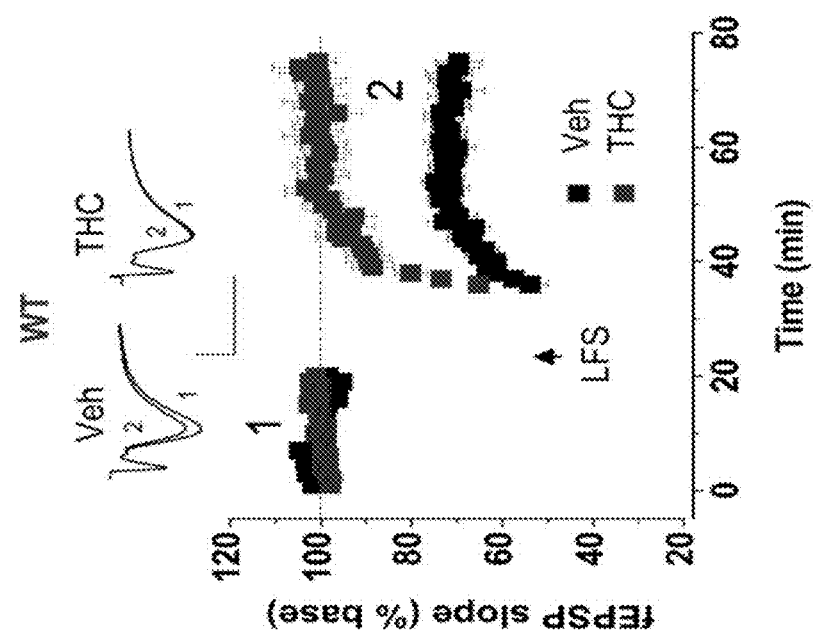
Fig. 11A
Fig. 11B

COMPOSITIONS, METHODS OF USE, AND METHODS OF TREATMENT

CLAIM OF PRIORITY TO RELATED APPLICATION

This application is a Divisional of U.S. patent application entitled "COMPOSITIONS, METHODS OF USE, AND METHODS OF TREATMENT" filed on Apr. 29, 2016 and assigned Ser. No. 15/033,141, which claimed the benefit of PCT/US2014/063118, filed Oct. 30, 2014, which claimed the benefit of U.S. provisional application entitled "COCKTAIL INTERVENTION TO TREAT HUMAN DISEASES AND DISORDERS" having Ser. No. 61/897,344, filed on Oct. 30, 2013, both of which are herein incorporated by reference in their entireties.

FEDERAL SPONSORSHIP

This invention was made with Government support under Contract/Grant No. R01 NS054886, awarded by the National Institutes of Health. The Government has certain rights in the invention.

SEQUENCE LISTING

This application contains a sequence listing filed in electronic form as an ASCII.txt file entitled 02102645.txt, created on Oct. 29, 2010, and having a size of 6,208 bytes. The content of the sequence listing is incorporated herein in its entirety.

BACKGROUND

Marijuana has been used for thousands of years to treat chronic pain, multiple sclerosis, cancer, seizure disorders, nausea, anorexia, inflammatory and neurodegenerative diseases. However, the undesirable neuropsychological and cognitive side effects greatly limit the medical use of marijuana. However, there are no currently FDA-approved effective medications for prevention and treatment of these *cannabis*-related disorders. Thus, there is a need to develop a treatment for preventing the negative effects of *cannabis*-related disorders.

SUMMARY

Embodiments of the present disclosure provide for compositions including compositions, pharmaceutical compositions, methods of treating a disease or condition, methods of treatment using compositions or pharmaceutical compositions, and the like.

In an embodiment, the composition can include a COX-2 inhibitor and a cannabinoid. In an embodiment, the COX-2 inhibitor can include: celecoxib, rofecoxib, meloxicam, piroxicam, deracoxib, parecoxib, valdecoxib, etoricoxib, a chromene derivative, a chroman derivative, N-(2-cyclohexyloxynitrophenyl)methane sulfonamide, COX189, ABT963, JTE-522, rofecoxib, valdecoxib, parecoxib, aspirin, acetaminophen, ibuprofen, flurbiprofen, ketoprofen, naproxen, oxaprozin, etodolac, indomethacin, ketorolac, lornoxicam, nabumetone, and diclofenac, as well as pharmaceutically acceptable salts of each, pharmaceutically acceptable derivatives of each, prodrugs of each, or mixtures thereof. In an embodiment, the cannabinoid is selected from the group consisting of: dronabinol, nabilone, cannabinol (CBD), tetrahydrocannabinol (THC), dimethyl heptylpentyl cannabidiol (DMHP-CBD), as well as pharmaceutically acceptable salts of each, pharmaceutically acceptable derivatives of each, prodrugs of each, or mixtures thereof.

In an embodiment, the pharmaceutical composition can include a therapeutically effective amount of a COX-2 inhibitor, or a pharmaceutically acceptable salt of the COX-2 inhibitor, a therapeutically effective amount of a cannabinoid, or a pharmaceutically acceptable salt of the cannabinoid, and a pharmaceutically acceptable carrier, to treat disease or condition. In an embodiment, the cannabinoid is formulated in a delayed-release cannabinoid formulation. In an embodiment, the disease and condition can include: Alzheimer's disease, Parkinson's disease, multiple sclerosis, epilepsy, traumatic brain injury, brain ischemia (stroke), arthritis, cancer, asthma, bronchitis asthma, bronchitis, inflammatory bowel disease, Crohn's disease, gastritis, irritable bowel syndrome, ulcerative colitis, migraine headaches, periarteritis *nodosa*, thyroiditis, aplastic anemia, Hodgkin's disease, sclerodma, rheumatic fever, type II diabetes, myasthenia gravis, amyotrophic lateral sclerosis, sacoidosis, nephrotic syndrome, Behchet's syndrome, polymyositis, gingivitis, peridontal disease, fibromyalgia, atopic dermatitis, insulitis, nausea, anorexia, pain, and post-traumatic stress disorder.

In an embodiment, the method of treating a disease or condition can include: administering to a subject in need thereof, a therapeutically effective amount of a COX-2 inhibitor, or a pharmaceutically acceptable salt of the COX-2 inhibitor, and a therapeutically effective amount of a cannabinoid, or a pharmaceutically acceptable salt of the cannabinoid, to treat the disease or condition.

Other compositions, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure.

FIGS. 1A-B illustrate that. $\Delta^9$-THC induces a dose- and time-dependent increase in hippocampal COX-2 expression (n=5). FIG. 1C illustrates that $\Delta^9$-THC increases synthesis of $PGE_2$ and the increase is blocked by Celebrex (Celeb) or genetic inhibition of COX-2 (COX-2 knockout). $PGE_2$ was detected 4 hrs after $\Delta^9$-THC injection (10 mg/kg). Celebrex (10 mg/kg) was injected 30 min prior to $\Delta^9$-THC injection (n=10/group). FIG. 1D illustrates that COX-2 is persistently elevated in animals that received repeated injections of $\Delta^9$-THC (10 mg/kg, i.p.) once a day for 7 consecutive days. COX-2 was analyzed 24 hrs after secession of the last injection (n=3). FIG. 1E illustrates that the COX-2 induction by $\Delta^9$-THC (10 mg/kg) is blocked by Rimonabant (RIM, 5 mg/kg). Hippocampal COX-2 was detected 4 hr after $\Delta^9$-THC injection (n=3). RIM was injected 30 min prior to $\Delta^9$-THC injection. FIG. 1F illustrates that the $\Delta^9$-THC fails to increase COX-2 in CB1R knockout mice (n=3). FIG. 1G illustrates that $\Delta^9$-THC increases COX-2 both in neurons and astroglial cells in culture and the increase is blocked by RIM. COX-2 was assayed 12 hr after treatments (n=6). All the data are presented as mean±SEM, *P<0.05, **P<0.01 compared with the vehicle controls, #P<0.05, ##P<0.01 compared with the vehicle controls, #P<0.05, ##P<0.01 compared with $\Delta^9$-THC (one-way ANOVA, Fisher's PLSD).

FIG. 2A illustrates an overexpression or knockdown of β1 and γ2 subunits eliminates $\Delta^9$-THC-increased COX-2 mRNA detected by qPCR in NG108-15 cells. Error bars represent ±SEM, **P<0.01 compared with the vehicle control (ANOVA, Fisher's PLSD, n=6). NG108-15 cells were transfected with pcDNA3.1 plasmids encoding $G\beta_1$ and $G\gamma_2$ subunits, or the pLL3.7 vector expressing Gβ1 and Gγ2 shRNA, or the vector expressing shRNA-resistant Gβ1γ2 in the absence and presence of $\Delta^9$-THC. FIG. 2B illustrates the disruption of Gβγ subunits blocks $\Delta^9$-THC-elevated COX-2, but does not prevent suppression of COX-2 by 2-AG in response to LPS stimulus in mixed culture of hippocampal neurons and astroglial cells (~10%). The culture was treated with a membrane permeable Gβγ-binding peptide mSIRK or a single point mutated (Leu 9 to Ala) Gβγ-binding peptide mSIRK ($L^{9A}$-mSIRK) in the absence and presence of $\Delta^9$-THC, LPS, PTX, 2-AG. FIG. 2C illustrates the silencing the Gαi1 subunit blocks 2-AG-suppressed COX-2, but does not affect the elevation of COX-2 by $\Delta^9$-THC in mixed culture of neurons and astroglial cells treated with the lentiviral vector expressing Gαi1 shRNA or shRNA-resistant Gαi1. FIG. 2D illustrates that $\Delta^9$-THC induces phosphorylation of Akt, ERK and p38MAPK and the phosphorylation is inhibited by knockdown of Gβγ2 and the inhibition is rescued by expressing shRNA-resistant Gβ1γ2. FIG. 2E, left, illustrates that $\Delta^9$-THC induces phosphorylation of NF-κB and the effect is blocked by Gβ1γ2 shRNA in NG108-15 cells. Middle: Binding of NF-κB p65 in the promoter region of the COX-2 gene (ptgs2) by chromatin immunoprecipitation (ChIP) analysis. FIG. 2E, right, illustrates that $\Delta^9$-THC-induced NF-κB phosphorylation and COX-2 expression are blocked by IKKβ inhibition in mixed culture of neurons and astroglial cells.

FIG. 3A, top, illustrates the representative fEPSPs recorded at hippocampal CA3-CA1 synapses from WT animals repeatedly injected with vehicle, $\Delta^9$-THC (10 mg/kg), NS398 (10 mg/kg), or $\Delta^9$-THC+NS398 once daily for 7 consecutive days. LTP was measured 24 hr after cessation of the last injection. FIG. 3A, left, illustrates the time courses of changes in fEPSP slope under different treatment. FIG. 3A, right, illustrates the mean values of the potentiation of fEPSPs averaged from 56 to 60 min following TBS (n=6 to 8 slices/5-6 animals). FIG. 3B, top, illustrates the representative fEPSPs recorded from COX-2 knockout (KO) mice injected with vehicle, or $\Delta^9$-THC (10 mg/kg) once daily for 7 consecutive days. FIG. 3B, left, illustrates the time courses of changes in fEPSP slope induced by $\Delta^9$-THC. FIG. 3B, right, illustrates the mean values of the potentiation of fEPSPs averaged from 56 to 60 min following TBS (n=8-12 slices/6-8 animals). Error bars represent ±SEM, **P<0.01 compared with vehicle controls; ##P<0.01 compared with $\Delta^9$-THC (ANOVA with Bonferronni post-hoc test). Scale bars in A1 and B1: 0.3 mV/10 msec.

FIG. 4A illustrates the impaired fear memory is attenuated by COX-2 inhibition. 24 hrs after a footshock conditioning, animals were administered with $\Delta^9$-THC (10 mg/kg) or NS398 (10 mg/kg) once a day for 7 days. Freezing behavior was recorded 24 hrs after the cessation of the last injections. FIG. 4B illustrates that COX-2 KO and WT mice received training in the Morris water maze for 5 days without any treatments (naïve). Starting at day 6, WT animals received vehicle, $\Delta^9$-THC (10 mg/kg), NS398 (10 mg/kg), $\Delta^9$-THC+NS398, once a day for 7 days. COX-2 KO mice received vehicle or $\Delta^9$-THC (10 mg/kg) for 7 days. Tests were performed 30 min following the injections. FIG. 4C illustrates that the probe trial test, which was conducted 24 hrs after the cessation of the last $\Delta^9$-THC injection. FIG. 4C, left, illustrates that the number of times crossed the target zone. FIG. 4C, middle, illustrates that the amount of time stayed in the target quadrant, and FIG. 4C, right, illustrates the swim speed in different treatments in probe trial tests. Error bars represent ±SEM, **P<0.01 compared with the vehicle control (n=9-12 animals/group, two-way ANOVA, Bonferronni post-hoc test).

FIG. 5A illustrates that the two-photon imaging of dendritic spines in CA1 hippocampal pyramidal neurons expressing GFP of transgenic mice. FIG. 5A, top left, is a representative image of a CA1 pyramidal neurons. Scale bar: 20 μm. FIG. 5A, top right, illustrates a representative images of dendritic spine segments from animals received different treatments. Scale bars: 3 μm. FIG. 5A, low left, illustrates the spine density in wild-type animals, and FIG. 5A, low right, illustrates that in COX-2 knockout (KO) mice (n=5 animals/group). FIG. 5B illustrates the expression of PSD-95 and synaptophysin (Syn) in animals treated with $\Delta^9$-THC or NS398 for 7 days (n=3 animals). FIG. 5C illustrates the immunostaining analysis of synaptic and extrasynaptic glutamate receptor subunits. FIG. 5C, left, illustrates a schematic of a hippocampal section. The red dash-line box marks the sampling field of immunostaining analysis. Scale bar: 200 μm. FIG. 5C, right, illustrates representative GluA1, GluN2A, GluN2B, and Syn immunoreactivities. Scale bar: 5 μm. FIG. 5D, left, illustrates the enlarged immunosignals of GluA1, GluN2A, GluN2B, Syn, and their overlay. Scale bars: 1.5 μm. FIG. 5D, right, illustrates quantification of synaptic (colocalized with Syn) and extrasynaptic (non-colocalized) GluA1, GluN2A, and GluN2B (n=5 animals/group). Error bars represent ±SEM, **P<0.01 compared with the vehicle control; #P<0.05, ##P<0.01 compared with $\Delta^9$-THC (ANOVA with Fisher's PLSD or Bonferronni post-hoc tests).

FIG. 6A illustrates an immunoblot analysis of hippocampal expression of GluR1, NR2A and NR2B subunits in WT and COX-2 KO mice treated with vehicle or $\Delta^9$-THC for 7 days (n=3). FIG. 6B illustrate the surface expression of GluR1, NR2A, and NR2B in WT and COX-2 KO mice treated with vehicle or $\Delta^9$-THC for 7 days (n=4). FIG. 6C illustrates the phosphorylation of hippocampal CREB in WT and KO mice treated with vehicle or $\Delta^9$-THC for 7 days (n=3). Error bars represent ±SEM, *P<0.05, **P<0.01 compared with the vehicle control (ANOVA with Fisher's PLSD).

FIG. 7A illustrates that $\Delta^9$-THC significantly reduces Aβ plaques detected using anti-4G8 antibody in 4-month-old 5XFAD APP transgenic (TG) mice in the absence and presence of COX-2 inhibition. TG mice received $\Delta^9$-THC (3 mg/kg) or Celebrex (1 mg/kg) once daily for 4 weeks starting at 3 months of age. FIG. 7B illustrates that $\Delta^9$-THC significantly reduces degenerated neurons detected by Fluoro-Jade C (FJC) staining in 6-month-old TG mice treated with/out Celebrex. TG mice received $\Delta^9$-THC (3 mg/kg) or Celebrex (1 mg/kg) once daily for 4 weeks starting at 5 months of age. FIG. 7C illustrates that $\Delta^9$-THC increases expression of neprilysin (NEP), but not β-site amyloid precursor protein cleaving enzyme 1 (BACE1) in TG mice. Error bars represent ±SEM, **$P<0.01$ compared with the vehicle control (n=3 to 5 animals/group; One-way ANOVA, Bonferronni post-hoc tests). Scale bars in A and B: 400 μm.

FIGS. 9A to 9H illustrate that COX-2 induction by $\Delta^9$-THC is mediated via Gβγ subunits, Related to FIG. 2. FIGS. 9A-B illustrate the overexpression and knockdown of Gβ1γ2 in NG108-15 cells. Expression Gβ1 and Gγ2 was detected using qPCR analysis (Error bars represent ±SEM, n=3 to 6). FIG. 9C illustrates the expression of Gαi1, Gαi2, and Gαi3 in mixed neuronal and astroglial cell culture treated with lentivirus expressing individual Gαi1 (1), Gαi2 (2), and Gαi3 (3) shRNAs. FIG. 9D illustrates the silencing the Gαi1 shRNA blocks 2-AG-induced suppression of COX-2 induced by LPS, while expression of Gαi2 or Gαi3 shRNA fails to blocks the COX-2 suppressive effect by 2-AG. Expression of Gαi1, Gαi2, or Gαi3 did not affect the increase in COX-2 by $\Delta^9$-THC in mixed culture of hippocampal neurons and astroglial cells. FIG. 9E, left, illustrates the immunoblot analysis of Gβ1, middle: Gγ2 levels in NG108-15 cells, and FIG. 9E, right, illustrates Gαi1 in mixed culture of hippocampal neurons and astroglial cells transduced with vectors or lentivirus expressing scramble, G131-, Gγ2-, and Gαi1-shRNA, and shRNA-resistant Gβ1, Gγ2, and Gαi1 (Feng et al., 2010). FIG. 9F illustrates that $\Delta^9$-THC (30 μM)-induced phosphorylation of Akt, ERK and p38MAPK is inhibited by overexpression of Gβ1γ2 in NG108-15 cells. FIG. 9G illustrates that the overexpression of Gβ1γ2 blocks $\Delta^9$-THC-induced NF-kB phosphorylation. FIG. 9H illustrates that the $\Delta^9$-THC (10 mg/kg) induces phosphorylation of Akt, ERK and p38MAPK in hippocampal tissue. FIG. 9I illustrates that 2-AG does not inhibit $\Delta^9$-THC-induced increase in COX-2 expression in mixed culture of neurons and astroglial cells.

FIG. 10C illustrates that repeated exposures to LPS reduce hippocampal LTP. Mice were injected with vehicle, LPS (3 mg/kg) or LPS+NS398 (10 mg/kg) once a day for 7 consecutive days. LTP was measured 24 hrs after cessation of the last injection. $P<0.01$ compared with vehicle controls. Scale bars: 0.3 mV/10 msec. Error bars represent ±SEM.

FIG. 11A illustrates that a single exposure to $\Delta^9$-THC impairs hippocampal LTD, Related to FIG. 3. LTD at CA3-CA1 synapses was induced by low-frequency stimulation (LFS, 900 stimuli at 1 Hz for 15 min). Wild-type (WT) mice (at ages of P12 to P17) received a single injection of $\Delta^9$-THC (10 mg/kg, i.p.). LTD was recorded 24 hrs after $\Delta^9$-THC injection. FIG. 11B illustrates that the LTD is normal in COX-2 knockout mice (KO) that received a single injection of $\Delta^9$-THC (10 mg/kg). Scale bars: 0.3 mV/10 msec.

FIG. 12A illustrates that catalepsy duration in WT or COX-2 KO mice injected with $\Delta^9$-THC (10 mg/kg), Celebrex (10 mg/kg), and $\Delta^9$-THC+Celebrex. Celebrex were injected 30 min prior to $\Delta^9$-THC injection. FIG. 12B illustrates that ambulation (number of entries into the center area) in WT or COX-2 KO mice that received the treatments as described in (A). **$P<0.01$ compared with the vehicle control (Error bars represent ±SEM, n=8 to 12, ANOVA, Bonferronni post-hoc test).

DISCUSSION

Figure 1A:
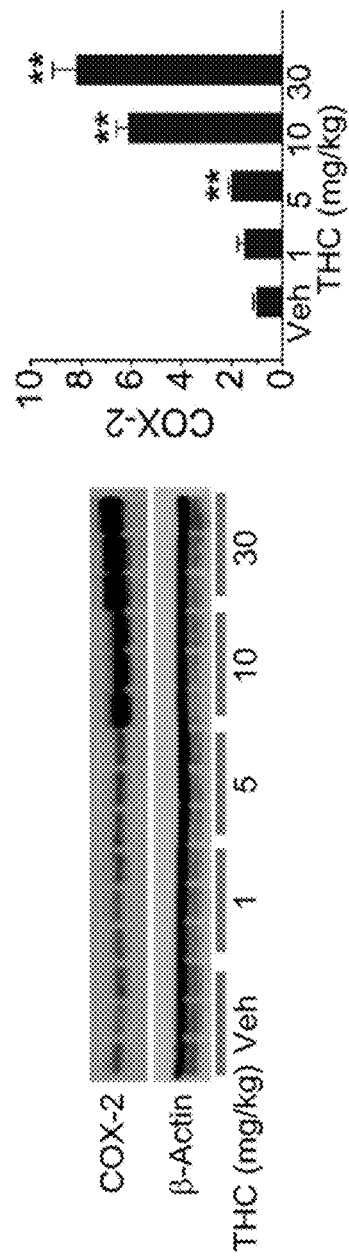
FIGS. 1A to 1G illustrate $\Delta^9$-THC in vivo exposure induces CB1R-dependent activation and elevation of COX-2 expression in the hippocampus.
Figure 1B:
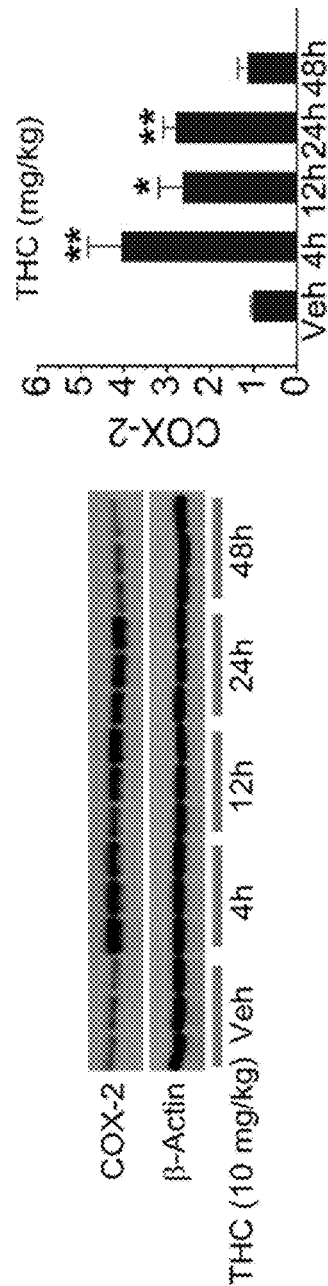

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of organic chemistry, biochemistry, microbiology, molecular biology, pharmacology, medicine, and the like, which are within the skill of the art. Such techniques are explained fully in the literature.

Prior to describing the various embodiments, the following definitions are provided and should be used unless otherwise indicated.

Definitions

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

The terms "sufficient" and "effective", as used interchangeably herein, refer to an amount (e.g. mass, volume, dosage, concentration, and/or time period) needed to achieve one or more desired result(s). In an embodiment, an effective amount of a cannabinoid refers to an amount needed to achieve one or more therapeutic effects. In an embodiment, an effective amount refers to an amount needed of a COX-2 inhibitor to substantially reduce or eliminate the negative side effects of a cannabinoid.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" or a "pharmaceutical formulation" is meant to encompass a composition or pharmaceutical composition suitable for administration to a subject, such as a mammal, especially a human and that refers to the combination of an active agent(s) (e.g., COX-2 inhibitor, cannabinoid), or ingredient with a pharmaceutically acceptable carrier or excipient, making the composition suitable for diagnostic, therapeutic, or preventive use in vitro, in vivo, or ex vivo. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease or condition being treated, and/or that amount that will prevent, to some extent, one or more of the symptoms of the condition or disease that the subject being treated has or is at risk of developing. In an embodiment, a therapeutically effective amount of a cannabinoid refers to an amount needed to achieve one or more therapeutic effects. In an embodiment, therapeutically effective amount refers to an amount needed of a COX-2 inhibitor to substantially reduce or eliminate the negative side effects of a cannabinoid.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure into a subject. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition (e.g. inflammation), a disease or a disorder with a composition to affect the condition (e.g., inflammation), disease or disorder by improving or altering it. The improvement or alteration may include an improvement in symptoms or an alteration in the physiologic pathways associated with the condition (e.g., inflammation), disease, or disorder. "Treatment," as used herein, covers one or more treatments of the disease or condition in a subject (e.g., a mammal, typically a human or non-human animal of veterinary interest), and includes: (a) reducing the risk of occurrence in a subject determined to be predisposed to the condition or disease but not yet diagnosed with it (b) impeding the development of the condition or disease, and/or (c) relieving the condition or disease, e.g., causing regression of the condition or disease and/or relieving one or more condition or disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition (e.g., condition or disease), a disease, or a symptom thereof and/or may be therapeutic in terms of a partial or complete cure for a condition (e.g., condition or disease), a disease, and/or adverse effect attributable to the disease.

As used herein, "therapeutic" refers to curing or treating a symptom of a disease or condition.

As used herein, the term "subject," or "patient," includes humans and mammals (e.g., mice, rats, pigs, cats, dogs, and horses), and non-mammals (e.g., ayes such as chickens etc.). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

As used herein, the term "COX-2 inhibitor" refers to a compound that is capable of inhibiting the activity or expression of COX-2 enzymes or is capable of inhibiting or reducing the severity, including pain and swelling, of a severe inflammatory response. In an embodiment, the COX-2 inhibitor can be a specific (e.g., Celebrex®) or a non-specific COX-2 inhibitor (e.g., aspirin).

As used herein, COX-2 inhibitors can include celecoxib (Celebrex®), rofecoxib (Vioxx®), meloxicam, piroxicam, deracoxib, parecoxib, valdecoxib, etoricoxib, a chromene derivative, a chroman derivative, N-(2-cyclohexyloxynitrophenyl)methane sulfonamide, COX189, ABT963, JTE-522, rofecoxib, valdecoxib, and parecoxib, as well as pharmaceutically acceptable salts, pharmaceutically acceptable derivatives, prodrugs, or mixtures thereof. In an embodiment, the COX-2 inhibitor can include an NSAID such as aspirin, acetaminophen, ibuprofen, flurbiprofen, ketoprofen, naproxen, oxaprozin, etodolac, indomethacin, ketorolac, lornoxicam, nabumetone, or diclofenac.

In an embodiment, the COX-2 inhibitors can include the compounds that are described in U.S. Pat. Nos. 6,310,079; 6,306,890 and 6,303,628 (bicydiccarbonyl indoles); U.S. Pat. No. 6,300,363 (indole compounds); U.S. Pat. Nos. 6,297,282 and 6,004,948 (substituted derivatives of benzosulphonamides); U.S. Pat. Nos. 6,239,173, 6,169,188, 6,133,292; 6,020,343; 6,071,954; 5,981,576 ((methylsulfonyl)phenyl furanones); U.S. Pat. No. 6,083,969 (diarylcycloalkano and cycloalkeno pyrazoles); U.S. Pat. No. 6,222,048 (diaryl-2-(5H)-furanones; U.S. Pat. No. 6,077,869 (aryl phenylhydrazines); U.S. Pat. Nos. 6,071,936 and 6,001,843 (substituted pyridines); U.S. Pat. No. 6,307,047 (pyridazinone compounds); U.S. Pat. No. 6,140,515 (3-aryl-4-aryloxyfuran-5-ones); U.S. Pat. Nos. 6,204,387 and 6,127,545 (diaryl pyridines); U.S. Pat. No. 6,057,319 (3,4-diaryl-2-hydroxy-2,5-dihydrofurans; U.S. Pat. No. 6,046,236 (carbocyclic sulfonamides); and U.S. Pat. Nos. 6,002,014; 5,994,381; and 5,945,539 (oxazole derivatives).

As used herein, a "cannabinoid" is a chemical compound (e.g., cannabinol (CBD), tetrahydrocannabinol (THC) or cannabidiol) that is found in the plant species *Cannabis saliva* (marijuana), and metabolites and synthetic analogues thereof. In an embodiment, the cannabinoids can include, but are not limited to, tetrahydrocannabinol, $\Delta^9$-tetrahydrocannabinol(THC), $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-1, AMG-3, AM41, 1, AM708, AM836, AM855, AM919, AM926, AM938, cannabidiol (CBD), cannabidiol propyl analogue (CBDV), cannabinol (CBN), cannabichromene, cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, 0-1 184 and mixtures thereof. In an embodiment, the cannabinoids can include, but are not limited to, dronabinol (Marino 1® or Namisol®) and nabilone (Cesamet®).

Discussion:

Embodiments of the present disclosure provide for compositions, pharmaceutical compositions, methods of treating a disease or condition, methods of treatment using compositions or pharmaceutical compositions, and the like. An embodiment of the present disclosure can be used to treat a condition or disease related to or the result of inflammation, in particular neuroinflammation. Additional details are described below and in the Examples.

A major problem with cannabinoid medicine has been the undesirable neuropsychological and cognitive side-effects of the cannabinoid (e.g., Δ9-tetrahydrocannabinol (Δ9-THC), the active ingredient in marinol), particularly for long-term treatment. However, the molecular mechanism underlying Δ9-THC-induced untoward effects has been discovered, which is related to the induction of cyclooxygenase-2 (COX-2), an inducible enzyme that synthesizes prostaglandins. In addition, it has been shown that pharmacological inhibition or genetic deletion of COX-2 prevents Δ9-THC exposure-induced impairments in hippocampal long-term synaptic plasticity and cognitive function. Ablation of COX-2 also attenuates or diminishes Δ9-THC-induced cataleptic and locomotor depressive effects. This means that Δ9-THC may display its beneficial properties with fewer undesirable side effects when its COX-2 induction effect is concurrently inhibited. In this regard, treatment using a cannabinoid and a COX-2 inhibitor in combination can reduce or eliminate the negative side-effects of the cannabinoid while retaining the beneficial effects of the cannabinoid. In particular, a combinatorial treatment of Δ9-THC and celecoxib, an FDA-approved selective COX-2 inhibitor, can reduce accumulation of Aβ plaques, neuroinflammation, and neurodegeneration and improve synaptic and cognitive function in a subject. Additional details are provided in the Example.

An embodiment of the present disclosure includes a composition or a pharmaceutical composition including a COX-2 inhibitor and a cannabinoid. In an embodiment, the COX-2 inhibitor can include any of those described herein, in particular, celecoxib (Celebrex®) and rofecoxib (Vioxx®). In an embodiment, the cannabinoid can include any of those described herein, in particular, CBD, THC, cannabidiol, dronabinol (Marino 1® or Namisol®), or nabilone (Cesamet®). In an embodiment, the cannabinoid can be a delayed-release (e.g., about 15 minutes or more) formulation of cannabinoid, so that the COX-2 inhibitor can enter the system of the subject to prevent or substantially prevent the negative side effects of the cannabinoid once the cannabinoid enters the system.

In an embodiment, the pharmaceutical composition includes a therapeutically effective amount of the COX-2 inhibitor (or a pharmaceutically acceptable salt of the COX-2 inhibitor), a therapeutically effective amount of the cannabinoid (or a pharmaceutically acceptable salt of the COX-2 inhibitor) and a pharmaceutically acceptable carrier, to treat the disease or condition. In an embodiment, the COX-2 inhibitor can include any of those described herein, in particular, those described herein or pharmaceutically acceptable salts thereof, as well as prodrugs thereof. In an embodiment, the cannabinoid can include any of those described herein, in particular, those described herein or pharmaceutically acceptable salts thereof, as well as prodrugs thereof. In an embodiment of the pharmaceutical composition, the cannabinoid can be a delayed-release formulation of cannabinoid.

In an embodiment, a first pharmaceutical composition includes a therapeutically effective amount of the COX-2 inhibitor (or a pharmaceutically acceptable salt, or prodrug of the COX-2 inhibitor), and a pharmaceutically acceptable carrier, to treat the disease or condition. In an embodiment, a second pharmaceutical composition includes a therapeutically effective amount of the cannabinoid (or a pharmaceutically acceptable salt or prodrug of the COX-2 inhibitor) and a pharmaceutically acceptable carrier, to treat the disease or condition. In an embodiment of the second pharmaceutical composition, the cannabinoid can be a delayed-release formulation of cannabinoid. In an embodiment, the first pharmaceutical composition and the second pharmaceutical composition can be co-administered or administered in a manner that achieves the desired goals. In an embodiment, at least for the first administration of the pharmaceutical compositions, the first pharmaceutical composition is administered prior to (e.g. about 15 or about 30 minutes or more) administration of the second pharmaceutical composition so that COX-2 inhibitor has the opportunity to be in the subjects system and prevent or substantially prevent the negative side effects of the cannabinoid once the cannabinoid enters the system.

In an embodiment, the disease or condition can include those directly related to, indirectly related to, or a result of inflammation, in particular, neuroinflammation. In an embodiment, the disease or condition can include one or more of the following: Alzheimer's disease, Parkinson's disease, multiple sclerosis, epilepsy, traumatic brain injury, brain ischemia (stroke), arthritis, cancer, asthma, bronchitis asthma, bronchitis, inflammatory bowel disease, Crohn's disease, gastritis, irritable bowel syndrome, ulcerative colitis, migraine headaches, periarteritis *nodosa*, thyroiditis, aplastic anemia, Hodgkin's disease, sclerodma, rheumatic fever, type II diabetes, myasthenia gravis, amyotrophic lateral sclerosis, sacoidosis, nephrotic syndrome, Behchet's syndrome, polymyositis, gingivitis, peridontal disease, fibromyalgia, atopic dermatitis, insulitis, nausea, anorexia, pain, post-traumatic stress disorder, and the like. In particular, the disease or condition can be Alzheimer's disease, Parkinson's disease, multiple sclerosis, epilepsy, traumatic brain injury, brain ischemia (stroke), cancer, arthritis, nausea, anorexia, pain, or post-traumatic stress disorder.

In an embodiment, the method of treatment of the disease or condition such as one directly or indirectly caused by inflammation includes administering to a subject in need thereof, a therapeutically effective amount of a COX-2 inhibitor, or a pharmaceutically acceptable salt of the COX-2 inhibitor, and a therapeutically effective amount of a cannabinoid, or a pharmaceutically acceptable salt of the cannabinoid, to treat the disease or condition.

As mentioned herein, the COX-2 inhibitor is used to substantially reduce or eliminate the negative effects of the cannabinoid, so the COX-2 inhibitor should be effectively within the system of the subject prior to the cannabinoid negative sides effects taking place or substantially limiting the extent and/or duration of the side effects and be in the system until the cannabinoid is out of the system. In this regard, the cannabinoid can be formulated in a delayed-release cannabinoid formulation. Also, the COX-2 inhibitor can be formulated in a sustained-release COX-2 formulation so that the COX-2 inhibitor stays in the system for the same period of the cannabinoid.

In an embodiment, the COX-2 inhibitor can be administered prior to the administration of the pharmaceutical composition including the cannabinoid or the pharmaceutical composition including both the COX-2 inhibitor and the cannabinoid. In this way, the COX-2 inhibitor can reduce the negative side effects of the cannabinoid. In particular, the COX-2 inhibitor and the cannabinoid can be administered separately, at least for the first dose of the COX-2 inhibitor. For example, the subject can be administered a first pharmaceutical composition that includes a therapeutically effective amount of a COX-2 inhibitor (or a pharmaceutically acceptable salt of the COX-2 inhibitor) and a pharmaceutically acceptable carrier. Then after a sufficient amount of time (e.g., about 15 minutes or more), the subject is administered a second pharmaceutical composition that includes a therapeutically effective amount of a cannabinoid (or a pharmaceutically acceptable salt of the cannabinoid), and a pharmaceutically acceptable carrier. In an embodiment, after the first administration of the first pharmaceutical composition, a third pharmaceutical composition (instead of the second composition) including both the COX-2 inhibitor and the cannabinoid can be administered. The dosage amount of the COX-2 inhibitor should be adjusted accordingly based on the method of treatment. For example, the cannabinoid may take longer to clear the system of the subject, so after the last dose of the cannabinoid is administered, a final dose or two of a COX-2 inhibitor can be administered to ensure that the negative side effects of the cannabinoid are not experienced.

It should be noted that the therapeutically effective amount to result in uptake of the cannabinoid and/or the COX-2 inhibitor into the subject can depend upon a variety of factors, including for example, the age, body weight, general health, sex, and diet of the subject; the time of administration; the route of administration; the rate of excretion of the specific compound(s) employed; the duration of the treatment; the existence of other drugs used in combination or coincidental with the specific composition employed; and like factors well known in the medical arts. As mentioned above, cannabinoids stay in the system for long periods of time, so this should be taken into account when developing a dosing regimen.

The present disclosure also provides packaged composition(s) or pharmaceutical composition(s) comprising a pharmaceutically acceptable carrier and the COX-2 inhibitor and the cannabinoid, in one or two compositions or pharmaceutical compositions for use in treating the disease or condition. Other packaged compositions or pharmaceutical compositions provided by the present disclosure further include indicia including at least one of: instructions for using the composition to treat the disease or condition, in particular, instructions relating to having the COX-2 inhibitor in the subjects system to substantially reduce or eliminate the negative side effects of the cannabinoid prior to the cannabinoid side effects occurring (e.g., through the use of one or more compositions or pharmaceutical compositions, delayed-release cannabinoid formulation, or the like). The kit can further include appropriate buffers and reagents known in the art for administering various combinations of the components listed above to the host.

Pharmaceutical Formulations and Routes of Administration

Embodiments of the present disclosure include a composition or pharmaceutical composition as identified herein (e.g., including one or both of a COX-2 inhibitor and a cannabinoid) and can be formulated with one or more pharmaceutically acceptable excipients, diluents, carriers and/or adjuvants. In addition, embodiments of the present disclosure include a composition or pharmaceutical composition formulated with one or more pharmaceutically acceptable auxiliary substances. In particular the composition or pharmaceutical composition can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the composition or pharmaceutical composition can be administered to the subject using any means capable of resulting in the desired effect. Thus, the composition or pharmaceutical composition can be incorporated into a variety of formulations for therapeutic administration. For example, the composition or pharmaceutical composition can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the composition or pharmaceutical composition may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the composition or pharmaceutical composition can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the composition or pharmaceutical composition can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the composition or pharmaceutical composition can be utilized in aerosol formulation to be administered via inhalation. Embodiments of the composition or pharmaceutical composition can be formulated into pressurized acceptable propellants such as dichlorodifluoromethane, propane, nitrogen and the like.

Furthermore, embodiments of the composition or pharmaceutical composition can be made into suppositories by mixing with a variety of bases such as emulsifying bases or water-soluble bases. Embodiments of the composition or pharmaceutical composition can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the composition or pharmaceutical composition in a composition as a solution in sterile water, normal saline or another pharmaceutically acceptable carrier.

Embodiments of the composition or pharmaceutical composition can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the composition or pharmaceutical composition can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the composition or pharmaceutical composition can be accomplished using any of a variety of refillable, pump systems. Pumps provide consistent, controlled release over time. In some embodiments, the composition or pharmaceutical composition can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent(s) (e.g., the COX-2 inhibitor and/or cannabinoid) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the composition or pharmaceutical composition are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the composition or pharmaceutical composition adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the composition or pharmaceutical composition may be administered using intravenous infusion, an implantable osmotic pump, a transdermal patch, liposomes, or other modes of administration. In one embodiment, a pump may be used (Sefton (1987). *CRC Crit. Ref Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). Science 249:1527-1533.

In another embodiment, the compositions of the present disclosure (as well as combination compositions separately or together) include those formed by impregnation of the composition or pharmaceutical composition described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

In another embodiment, the compositions or pharmaceutical compositions of the present disclosure (as well as combination compositions separately or together), in particular cannabinoids, can be part of a delayed-release formulation such as a delayed-release cannabinoid formulation. Delayed-release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Delayed-release formulations can be created by coating a solid dosage (e.g., cannabinoid) form with a polymer film, which is insoluble in the acidic environment of the stomach, and soluble in the neutral environment of the small intestine.

pH dependent polymers are frequently used to delay release, for example following ingestion, until the composition has passed through the low pH of the stomach and entered into the higher pH of the small intestine. Representative pH dependent polymer include, but not limited to, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid The delayed release dosage units can be prepared, for example, by coating a drug (e.g., cannabinoid) or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Dosages

Embodiments of the composition or pharmaceutical composition can be administered to a subject in one or more doses. Those of skill will readily appreciate that dose levels can vary as a function of the specific the composition or pharmaceutical composition administered, the severity of the symptoms and the susceptibility of the subject to side effects. Preferred dosages for a given compound are readily determinable by those of skill in the art by a variety of means.

In an embodiment, multiple doses of the composition or pharmaceutical composition are administered. The frequency of administration of the composition or pharmaceutical composition can vary depending on any of a variety of factors, e.g., severity of the symptoms, and the like. For example, in an embodiment, the composition or pharmaceutical composition can be administered once per month, twice per month, three times per month, every other week (qow), once per week (qw), twice per week (biw), three times per week (tiw), four times per week, five times per week, six times per week, every other day (qod), daily (qd), twice a day (qid), three times a day (tid), or four times a day. As discussed above, in an embodiment, the composition or pharmaceutical composition is administered 1 to 4 times a day over a 1 to 10 day time period.

The duration of administration of the composition or pharmaceutical composition analogue, e.g., the period of time over which the composition or pharmaceutical composition is administered, can vary, depending on any of a variety of factors, e.g., patient response, etc. For example, the composition or pharmaceutical composition in combination or separately, can be administered over a period of time of about one day to one week, about one day to two weeks.

The amount of the COX-2 inhibitor and cannabinoid in compositions and pharmaceutical compositions of the present disclosure that can be effective in treating the condition or disease can be determined by standard clinical techniques. In addition, in vitro or in vivo assays can optionally be employed to help identify optimal dosage ranges. The precise dose to be employed can also depend on the route of administration, and can be decided according to the judgment of the practitioner and each patient's circumstances. In general, suitable dosage ranges for oral administration can generally be about 0.001 to 400 milligrams of the components, independently, of the present disclosure or a pharmaceutically acceptable salt thereof per kilogram body weight per day. In an embodiment of the disclosure, the oral dose can be about 0.01 to about 100 milligrams per kilogram body weight per day, about 0.1 to about 75 milligrams per kilogram body weight per day, about 0.1 to about 15 milligrams per kilogram body weight per day, about 0.1 to about 10 milligrams per kilogram body weight per day, about 0.1 to about 5 milligrams per kilogram body weight per day, or about 0.1 to 2 milligrams per kilogram body weight per day. The dosage amounts described herein can refer to each of the COX-2 inhibitor and cannabinoid independently.

In an embodiment, COX-2 inhibitor dosage forms can be a daily dosage amount of about 1 mg to 1000 mg, about 1 mg to 100 mg, about 1 mg to 150 mg, 1 mg to 200 mg, I mg to about 250 mg, 1 mg to 300 mg, about 1 mg to 500 mg, or about 1 mg to 700 mg. In a particular embodiment, a unit dosage of the COX-2 inhibitor for oral administration to a mammal of about 50 to 70 kg may contain about 1 and 1000 mg, e.g. about 1-300 mg, preferably 10-100 mg of the active ingredient.

In an embodiment, the dose of the cannabinoid received by the subject can be about 0.01 to 50 milligrams per kilogram body weight per day, about 0.1 to 20 milligrams per kilogram body weight per day, about 0.1 to 10 milligrams per kilogram body weight per day, about 0.1 to 5 milligrams per kilogram body weight per day., or about 0.1 to 2.5 milligrams per kilogram body weight per day.

Routes of Administration

Embodiments of the present disclosure provide methods and compositions for the administration of the active agent(s) (e.g., a COX-2 inhibitor and/or cannabinoid) to a subject (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., a COX-2 inhibitor and/or cannabinoid) can be administered in a single dose or in multiple doses.

Embodiments of the composition or pharmaceutical composition can be administered to a subject using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the COX-2 inhibitor and/or cannabinoid. Where systemic delivery is desired, administration typically involves invasive or systemically absorbed topical or mucosal administration of pharmaceutical preparations.

In an embodiment, the composition or pharmaceutical composition can also be delivered to the subject by enteral administration. Enteral routes of administration include, but are not limited to, oral and rectal (e.g., using a suppository) delivery.

Methods of administration of the composition or pharmaceutical composition through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Marijuana has been used for thousands of years as a treatment for medical conditions. However, untoward side effects limit its medical value. Here we show that synaptic and cognitive impairments following repeated exposure to Δ⁹-tetrahydrocannabinol (Δ⁹-THC) are associated with the induction of cyclooxygenase-2 (COX-2), an inducible enzyme that converts arachidonic acid to prostanoids, in the brain. COX-2 induction by Δ⁹-THC is mediated via CB1 receptor-coupled G-protein βγ subunits. Pharmacological or genetic inhibition of COX-2 blocks down-regulation and internalization of glutamate receptor subunits and alterations of the dendritic spine density of hippocampal neurons induced by repeated Δ⁹-THC exposures. Ablation of COX-2 also eliminates Δ⁹-THC-impaired hippocampal long-term synaptic plasticity, spatial, and fear memories. Importantly, the beneficial effects of decreasing β-amyloid plaques and neurodegeneration by Δ⁹-THC in Alzheimer's disease animals are retained in the presence of COX-2 inhibition. These results suggest that the applicability of medical marijuana would be broadened by concurrent inhibition of COX-2.

Introduction:

Marijuana has been used for thousands of years to treat chronic pain, multiple sclerosis, cancer, seizure disorders, nausea, anorexia, inflammatory and neurodegenerative diseases (Robson et al, 2001; Russo, 2007). However, the undesirable neuropsychological and cognitive side effects greatly limit the medical use of marijuana (Carlini, 2004). The major intoxicating effects of *cannabis* are the impairments in synaptic and cognitive function (Pope et al., 2001; Solowij et al., 2002; Messinis et al., 2006). These untoward effects are also the primary consequences of *cannabis* abuse. However, there are no currently FDA-approved effective medications for prevention and treatment of these *cannabis*-related disorders.

As it is clear now, Δ⁹-tetrahydrocannabinol (Δ⁹-THC) is the major psychoactive ingredient of marijuana (Gaoni and Mechoulam, 1964) and its effects are largely mediated through cannabinoid receptors (CB1R or CB2R), which are pertussis toxin (PTX) sensitive G protein-coupled receptors (Howlett, 1998; Pertwee et al., 2010). Previous studies demonstrate that deficits in long-term synaptic plasticity, learning and memory by Δ⁹-THC exposure are primarily mediated through CB expressed in the brain (Lichtman and Martin, 1996; Hoffman et al., 2007; Puighermanal et al., 2009; Fan et al., 2010; Han et al., 2012). However, the molecular mechanisms underlying the synaptic and cognitive deficits elicited by repeated Δ⁹-THC exposure are largely unknown.

In the present Example, we unexpectedly observed that Δ⁹-THC increases expression and activity of cyclooxygenase-2 (COX-2), an inducible enzyme that converts arachidonic acid to prostanoids, both in vitro and in vivo via a CB1R-dependent mechanism. This action is opposite to the observations where the endogenous cannabinoid 2-arachidonylglycerol (2-AG) induces a CB1R-dependent suppression of COX-2 activity and expression in response to proinflammatory and excitotoxic insults (Zhang and Chen, 2008). The differential modulation of COX-2 by the exogenous cannabinoid Δ⁹-THC and endogenous cannabinoid 2-AG appears to result from intrinsic properties of the CB1R-coupled G-protein. The COX-2 induction by Δ⁹-THC is mediated via Gβγ subunits, while COX-2 suppression by 2-AG is mediated through the Gαi subunit. Interestingly, the impairments in hippocampal long-term synaptic plasticity, spatial, and fear memories induced by repeated Δ⁹-THC exposure can be occluded or attenuated by pharmacological or genetic inhibition of COX-2. Finally, the beneficial effects of reducing Aβ and neurodegeneration by Δ⁹-THC are retained in the presence of COX-2 inhibition. Our results reveal a previously unknown signaling pathway that is linked to synaptic and cognitive deficits induced by Δ⁹-THC exposure, suggesting that Δ⁹-THC would display its beneficial properties with fewer undesirable side effects when its COX-2 induction effect is inhibited, which may form a novel therapeutic intervention for medical treatments.

Figure 1C:
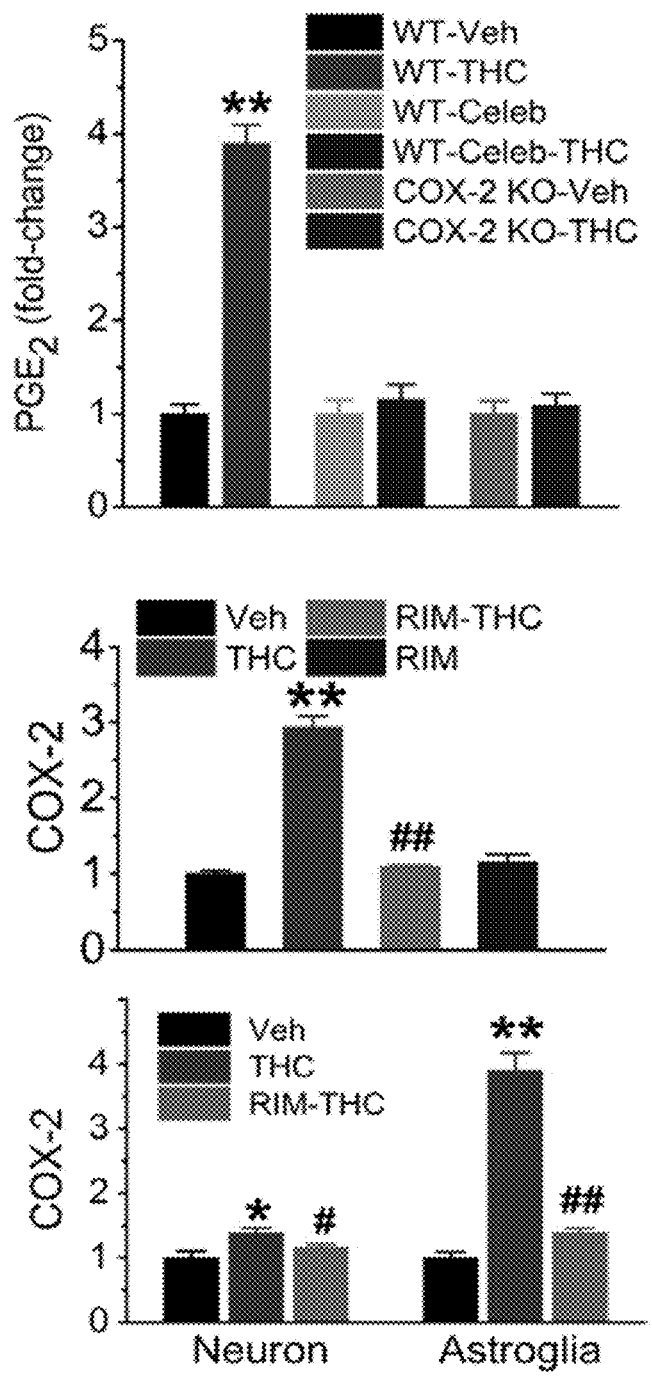
Figure 1D:
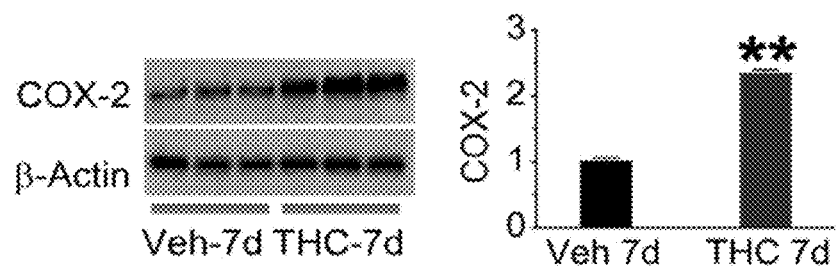
Figure 1E:
Figure 1F:
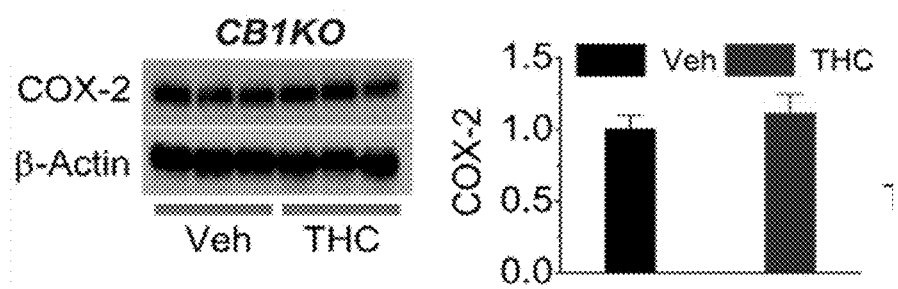
Figure 1G:
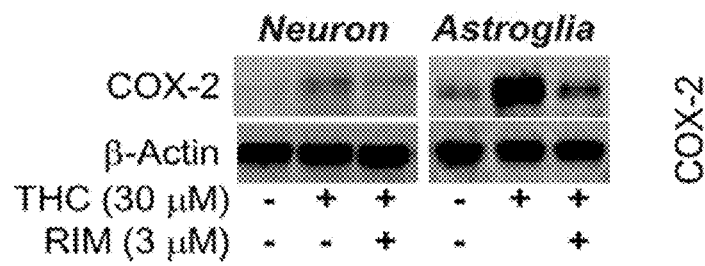
Figure 2A:
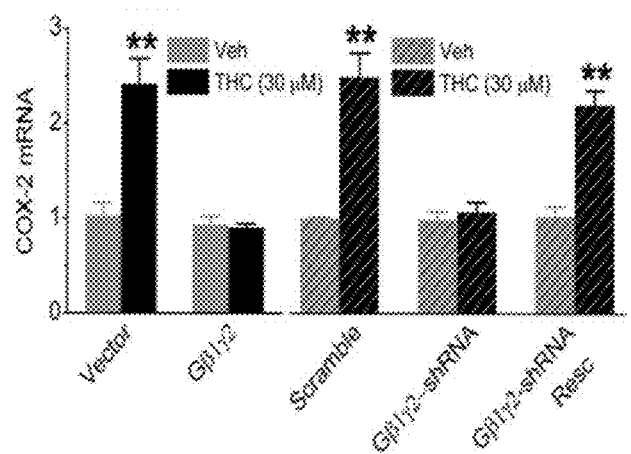
FIGS. 2A to 2E illustrate Gβγ subunits mediate $\Delta^9$-THC-elevated COX-2 expression.
Figure 2B:
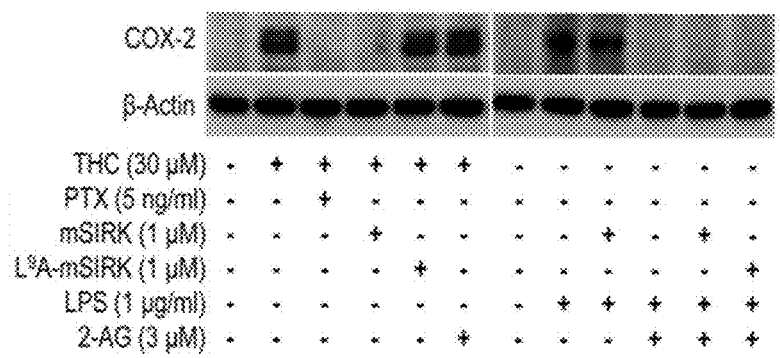
Figure 2C:
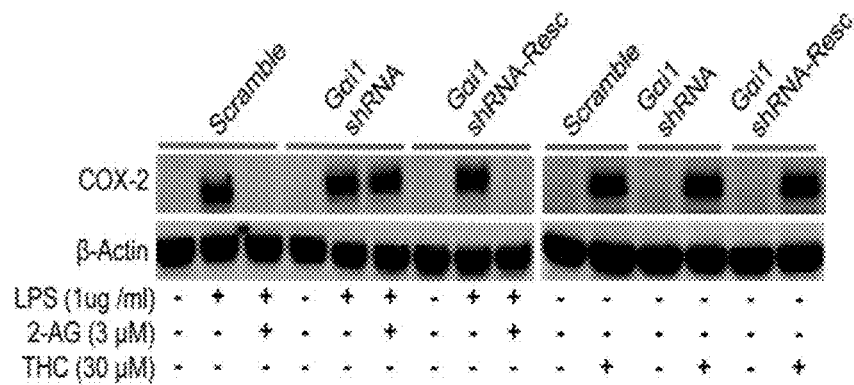
Figure 8A:
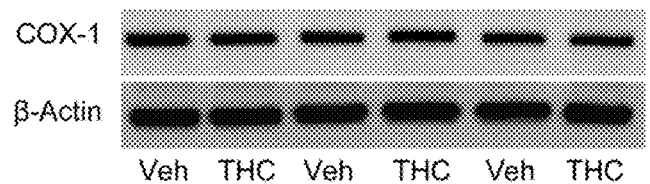
FIG. 8A illustrates that $\Delta^9$-THC does not increase in COX-1 expression in the hippocampus, Related to FIG. 1. COX-1 protein was detected 4 hrs after $\Delta^9$-THC injection (10 mg/kg, n=3).
Figure 8B:
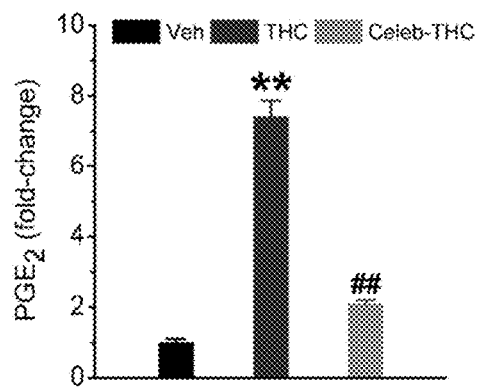
FIG. 8B illustrates that $\Delta^9$-THC increase hippocampal PGE2 synthesis and the increase is blocked by Celebrex (Celeb, 10 mg/kg, n=10 animals/group)). PGE2 was detected 30 min after injection of $\Delta^9$-THC.
Figure 8C:
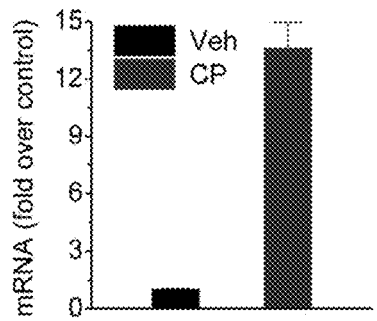
FIGS. 8C-E illustrate that the synthetic cannabinoid CP55,940 (CP) increases COX-2 expression and PGE2 synthesis. COX-2 expression and PGE2 were detected 4 hrs after CP (10 mg/kg). NS398 (10 mg/kg) was administered 30 min prior to injection of CP. Hippocampal COX-2 mRNA was detected using the qPCR analysis. Increase in PGE2 by CP is inhibited by NS398 (n=5 to 7/group). All the data are presented as mean±SEM, **$P<0.01$ compared with the vehicle control, ##$P<0.01$ compared with $\Delta^9$-THC or CP (one-way ANOVA with Fisher's PLSD).
Figure 8D:
Figure 8E:
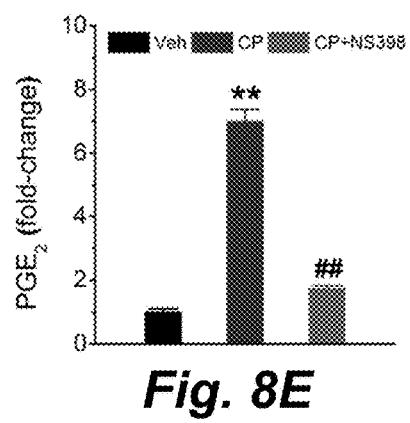
Figure 9A:
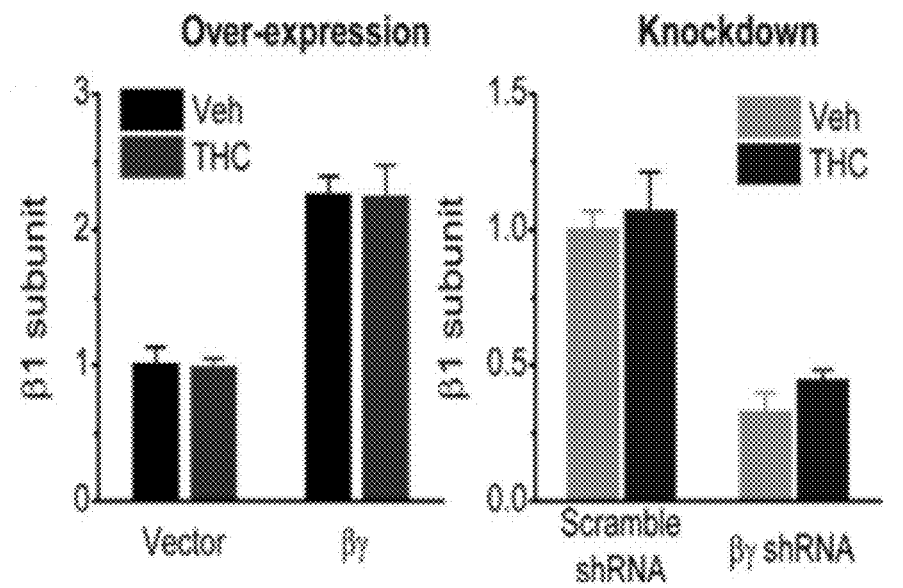
Figure 9B:
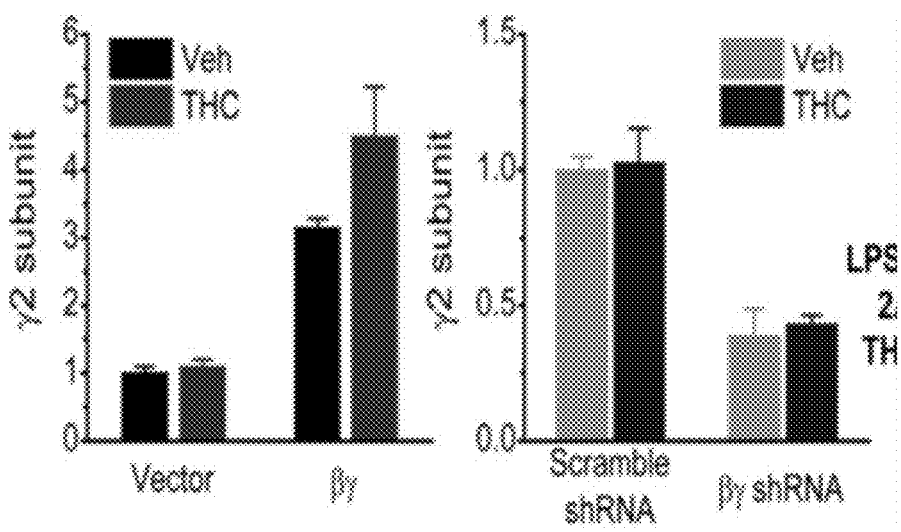
Figures 14, 15:
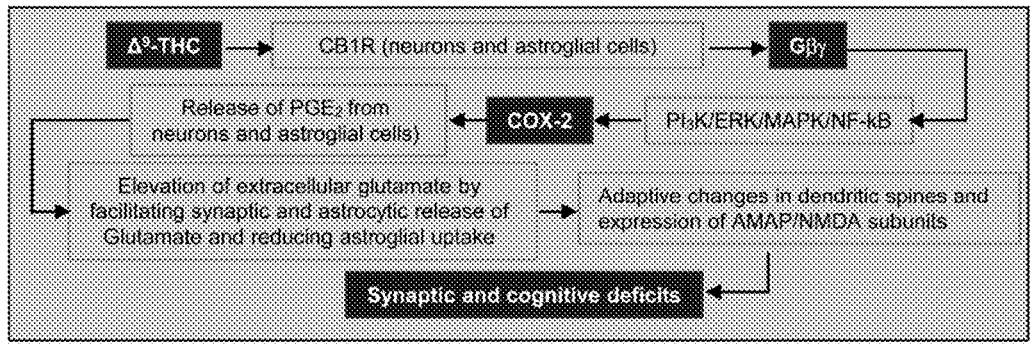
FIG. 14 illustrates a hypothetical signaling pathways involved in $\Delta^9$-THC-induced synaptic and cognitive deficits. (Related to FIGS. 1 to 7)
FIG. 15 illustrates Table S1.

Results:

Δ⁹-THC Induces Dose- and Time-Dependent Increase in COX-2 Expression:

Identification of CBRs led to discovery of several endogenous cannabinoids, including anandamide (AEA) and 2-arachidonylglycerol (2-AG), which are the most studied endocannabinoids involved in a variety of physiological, pharmacological, and pathological processes (Kano et al., 2009; Pertwee et al., 2010). 2-AG, the most abundant endocannabinoid, plays significant roles in synaptic modification, resolution of neuroinflammation, and neuronal survival (Alger, 2009; Chevaleyre et al., 2006; Lovinger, 2008; Panikashvili, et al., 2001; Zhang and Chen, 2008). In particular, its anti-inflammatory and neuroprotective effects in response to proinflammatory and neurotoxic insults appear to be through limiting COX-2 signaling (Chen et al., 2011, Du et al., 2011; Zhang and Chen, 2008). Since acute inhibition of COX-2 by selective COX-2 inhibitors has been shown to decrease hippocampal long-term potentiation (LTP) and impairs memory consolidation (Chen et al., 2002; Teather et al., 2002; Cowley et al., 2008). We thus wondered whether impairments of synaptic plasticity and memory by marijuana result from a COX-2 suppressive effect. To assess this, we first analyzed hippocampal expression and activity of COX-2 in mice that received Δ⁹-THC. Unexpectedly, in vivo exposure to Δ⁹-THC produced a dose- and time-dependent induction of COX-2 in the brain, rather than suppression (FIGS. 1A & B), while expression of COX-1 was unaffected by Δ⁹-THC (supplementary Fig. S1A). The increase in COX-2 expression induced by Δ⁹-THC was accompanied by elevated production of prostaglandin $E_2$ ($PGE_2$), which could be inhibited by the selective COX-2 inhibitor Celebrex or genetic inhibition of COX-2 (FIG. 1C, FIG. 8B). To confirm the ability of exogenous cannabinoids to induce COX-2, we assessed COX-2 expression and $PGE_2$ production in animals injected with the synthetic cannabinoid CP55,940 (CP). As expected, CP produced more pronounced effects on COX-2 expression and $PGE_2$ synthesis (FIG. 8C-E). The increase in $PGE_2$ could be blocked by NS398, another selective COX-2 inhibitor. In addition, we observed that COX-2 expression was steadily elevated in animals injected with Δ⁹-THC once daily for 7 consecutive days although the magnitude of increase in COX-2 was not as intensified as that of a single injection (FIG. 1D). This indicates that expression of COX-2 is persistently elevated upon repeated exposure to Δ⁹-THC FIG. 14). COX-2 induction by Δ⁹-THC is CB1R-dependent:

Since undesirable side effects elicited by cannabinoids are primarily mediated by CB1R (Lichtman and Martin, 1996; Hoffman et al., 2007; Han et al., 2012), we wondered whether COX-2 induction by Δ⁹-THC is mediated via CB1R. As shown in FIGS. 1E & F, Δ⁹-THC-induced increase in COX-2 in the hippocampus was blocked either by Rimonabant (RIM), a selective CB antagonist, or by genetic deletion of CB1R. To determine whether the increase in COX-2 by Δ⁹-THC occurs in neurons or astroglial cells, we made different conditions in cultures as described previously (Zhang and Chen, 2008). We found that while Δ⁹-THC induced a CB1R-dependent increase in COX-2 expression both in neuronal and astroglial cell-enriched cultures, the increased was more pronounced in astroglial cell-enriched cultures than in neuronal culture (FIG. 1G). Our data provide convincing evidence that COX-2 induction by $\Delta^9$-THC both in vivo and in vitro is mediated via CB1R. COX-2 induction by $\Delta^9$-THC is via CB1R-coupled G protein βγ subunits:

Since the suppression of COX-2 by 2-AG in response to proinflammatory stimuli occurs via a CB1R-dependent mechanism (Zhang and Chen, 2008), we questioned why the exogenous cannabinoid $\Delta^9$-THC increases COX-2 and the endogenous cannabinoid 2-AG suppresses COX-2 acting through the same CB1R-dependent mechanism, and speculated that CB1R may not be the key molecule responsible for differential regulation of COX-2 expression upon exposure to cannabinoids. CB1R is coupled to a PTX-sensitive Gi/o protein, and activation of CB1R releases Gβγ subunits from the GTP-bound Gαi subunit (Howlett, 1998; Pertwee et al., 2010). Earlier studies show that activation of CB1R is capable of inducing Gβγ-mediated response (Guo and Ikeda, 2004; Wilson et al., 2001; Yao et al., 2003). We hypothesized that Gβγ and Gαi may differentially mediate COX-2 induction or suppression by exogenous $\Delta^9$-THC or endogenous 2-AG. To test this prediction, we first over-expressed Gβγ subunits by transfection with plasmids carrying β1 and γ2 subunits in NG108-15 cells, which express native CB1R (FIGS. 9A & B). While $\Delta^9$-THC still increased expression of COX-2 mRNA in culture transfected with the control vector, it did not increase COX-2 in culture overexpressing β1 and γ2 subunits (FIG. 2A1). In subsequent experiments, β1 and γ2 subunits were silenced by shRNA. Knockdown of β1γ2 by shRNA suppressing endogenous β1γ2 also blocked COX-2 induction by $\Delta^9$-THC in NG108-15 cells, and the blockade was rescued by concurrently expressing shRNA-resistant β1γ2 (FIG. 2A2, FIG. 9E). This indicates that COX-2 induction by $\Delta^9$-THC is likely mediated through Gβγ. To further confirm that Gβγ mediate COX-2 induction by $\Delta^9$-THC, we treated mixed culture of hippocampal neurons and astroglial cells (~5-10%) with a membrane-permeable Gβγ-binding peptide mSIRK to disrupt the function of Gβγ (Delaney et al., 2007; Goubaeva et al., 2003). As a negative control, we used a variant mSIRK with a point mutation of Leu$^9$ to Ala (L$^9$A-mSIRK). As shown in FIG. 2B, disruption of Gβγ activity by mSIRK also blocked COX-2 induction by $\Delta^9$-THC, while it failed to block the suppression of COX-2 by 2-AG in response to LPS, a commonly used COX-2 inducer (Zhang and Chen, 2008). PTX treatment also blocked $\Delta^9$-THC-induced increase in COX-2. Interestingly, application of 2-AG failed to suppress $\Delta^9$-THC-induced increase in COX-2 (FIG. 2B, FIG. 9I). To test the prediction that Gαi mediates COX-2 suppressive effect by 2-AG, we silenced Gαi using a lentiviral vector in mixed culture of neurons and astroglial cells (FIG. 9C). As illustrated in FIG. 2C and FIG. 9D, silencing Gαi1, but not Gαi2 or Gαi3, blocked the suppression of COX-2 by 2-AG in response to the LPS stimulus, and this blocking effect was rescued by concurrently expressing shRNA-resistant Gαi1 (FIG. 2C, FIG. 9E). Knockdown of Gαi1, Gαi2 or Gαi3 did not block COX-2 induction by $\Delta^9$-THC (FIG. 2C and FIG. 9D). These results indicate that COX-2 induction by $\Delta^9$-THC is likely mediated via Gβγ, while COX-2 suppression by 2-AG is likely mediated through Gαi1 (FIG. 14).

Figure 2D:
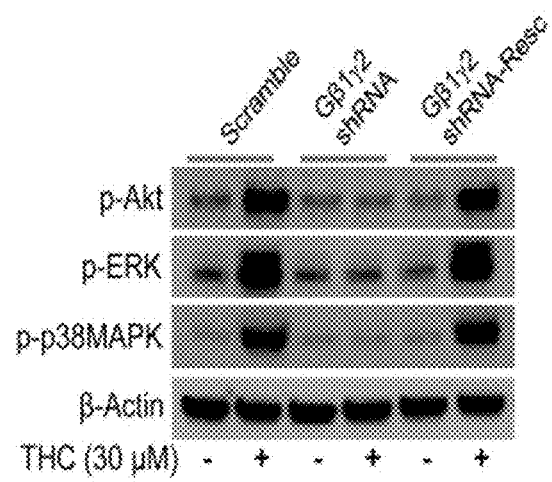
Figure 2D:
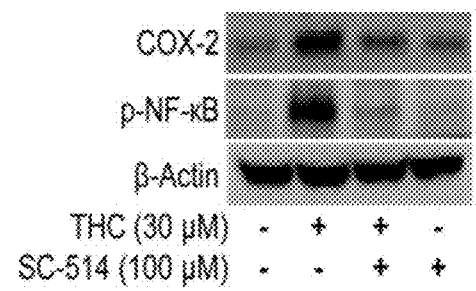
Figure 2E:
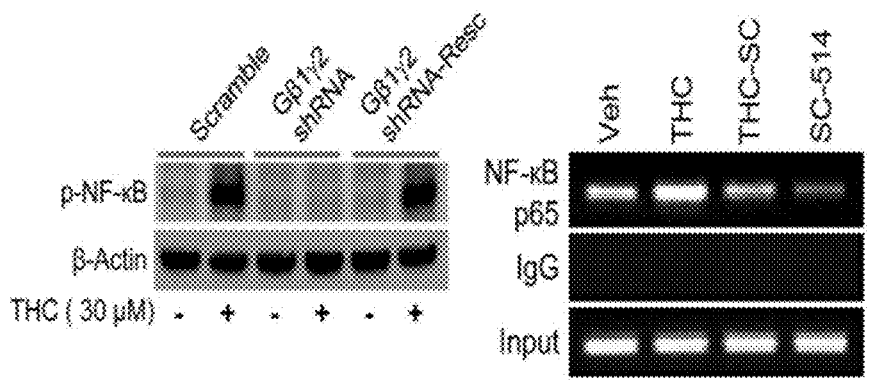
Figure 3A:
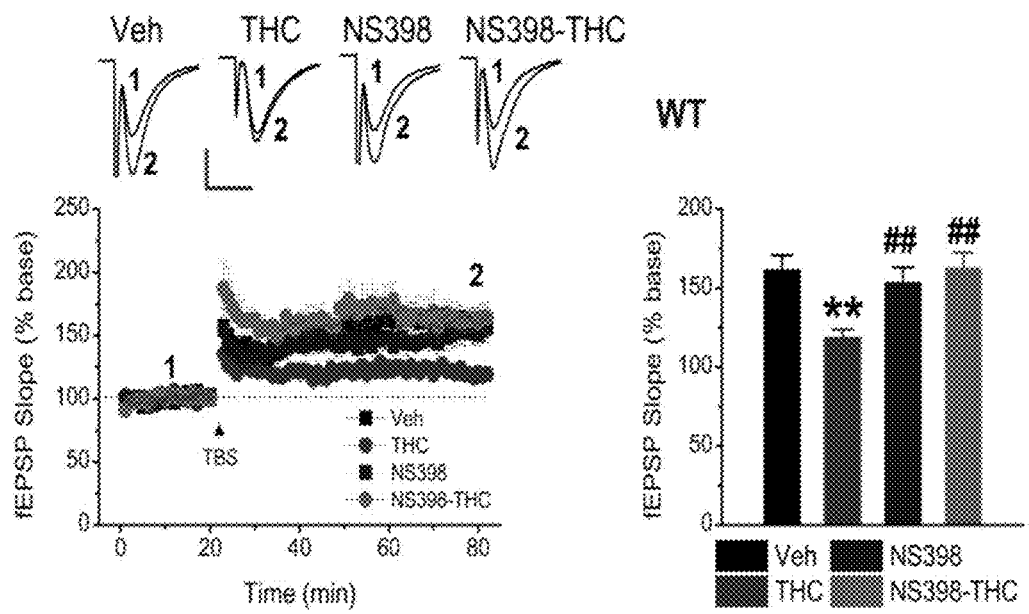
FIGS. 3A and 3B illustrate that inhibition of COX-2 eliminates deficits in long-term potentiation (LTP) by repeated $\Delta^9$-THC exposure.
Figure 3B:
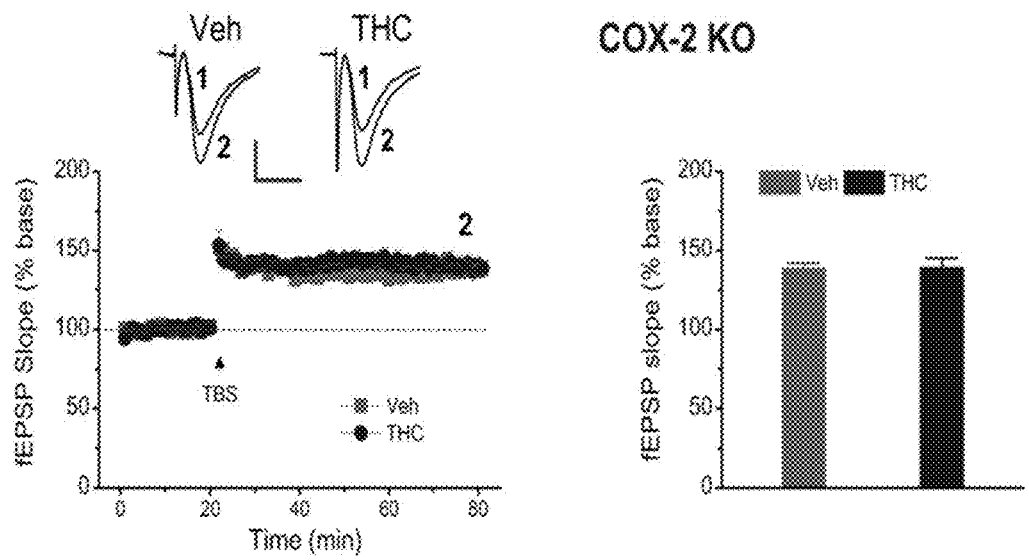

Akt, ERK, p38MAPK and NF-κB are Downstream Signaling of Gβγ:

To determine downstream signaling pathways of Gβγ, we detected phosphorylation of Akt, ERK, and p38MAPK by overexpression or knockdown of Gβγ in the presence and absence of $\Delta^9$-THC. As shown in FIG. 2D and FIG. 9F, $\Delta^9$-THC induced phosphorylation of these signaling molecules and the phosphorylation was inhibited by knockdown or over-expression of Gβ1γ2. Inhibition of phosphorylation of these mediators by shRNA was rescued by concurrently expressing shRNA-resistant Gβ1γ2 (FIG. 2D). These data indicate that COX-2 induction by $\Delta^9$-THC is likely through signaling of these downstream molecules of Gβγ. To further characterize this signaling pathway that regulates COX-2 expression by $\Delta^9$-THC, we targeted NF-κB, which is a transcription factor regulating expression of genes including the COX-2 gene (ptgs2). We observed that $\Delta^9$-THC induced NF-κB phosphorylation in NG-108-15 cells and this phosphorylation was inhibited by overexpression or knockdown of Gβγ, and rescued by concurrently expressing shRNA-resistant Gβ1γ2 (FIG. 2E1, FIG. 9G). To determine regulation of COX-2 transcription by NF-κB, we performed a chromatin immunoprecipitation (CHIP) analysis in mixed culture of neurons and astroglial cells. As shown in FIG. 2E2, a binding activity of NF-κB p65 was detected in the promoter positions (-419 to -428 bp) of ptgs2, and this interaction was enhanced by $\Delta^9$-THC and inhibited by SC-514, a specific IKKβ inhibitor that inhibits p65-associated transcriptional activation of the NF-κB pathway. To further confirm the involvement of NF-κB in $\Delta^9$-THC-induced increase in COX-2, COX-2 expression and NF-κB phosphorylation by $\Delta^9$-THC were determined in the absence and presence of SC-514. Inhibition of IKKβ blocked $\Delta^9$-THC-induced COX-2 and NF-κB phosphorylation (FIG. 2E3). Phosphorylation of Akt, ERK, p38MAPK and NF-κB was confirmed in the hippocampus of animals that received $\Delta^9$-THC (FIG. 9H).

Figure 10A:
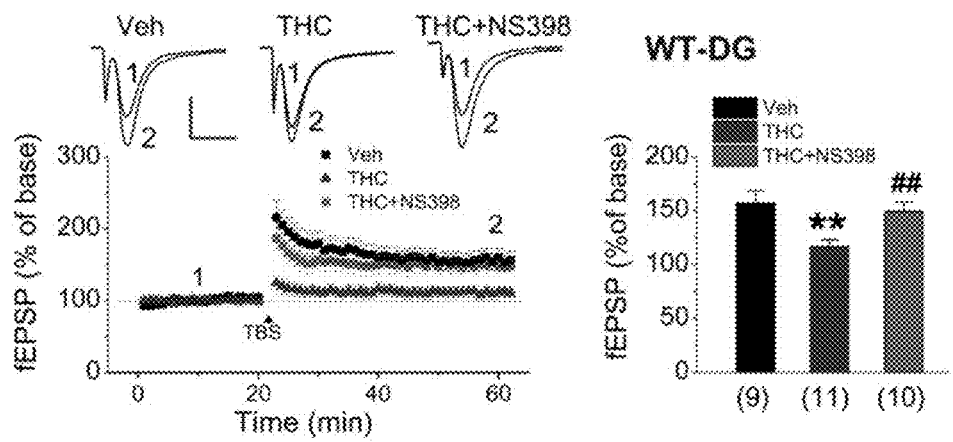
FIGS. 10A to 10C illustrate pharmacological or genetic inhibition of COX-2 prevents LTP reduction by repeated exposures to $\Delta^9$-THC, Related to FIG. 3. $\Delta^9$-THC (10 mg/kg) was injected (i.p.) once a day for 7 days. NS398 (10 mg/kg) was injected 30 min before $\Delta^9$-THC injection. Perforant LTP in WT, FIG. 10A, and COX-2 KO, FIG. 10B, mice was determined 24 hrs after cessation of the last injection. $P<0.01$ compared with the vehicle control, ##$P<0.01$ compared with $\Delta^9$-THC. (ANOVA with Bonferronni post-hoc test; n=9 to 13 slices/6 to 9 mice).
Figure 10B:
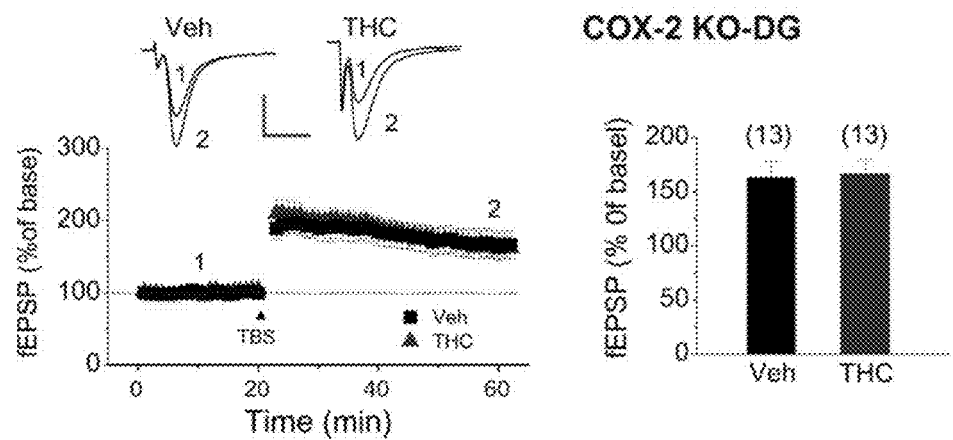
Figure 10C:
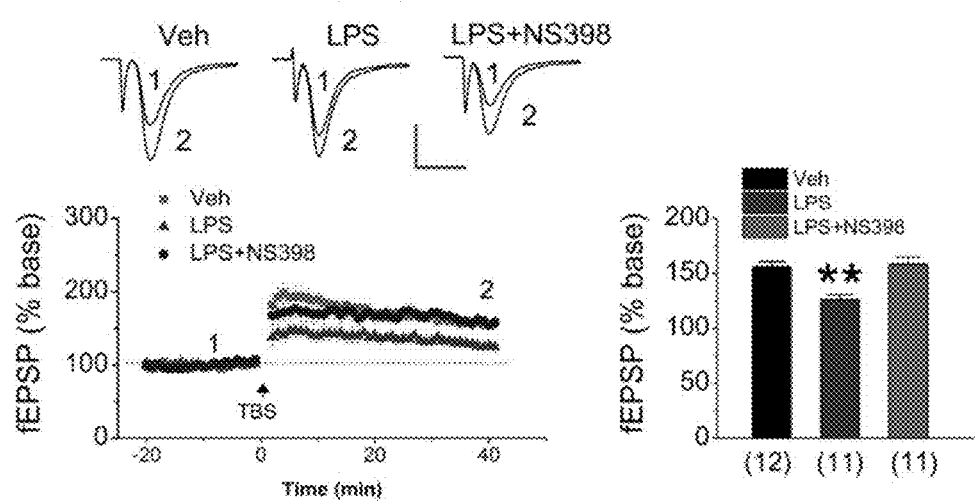

Inhibition of COX-2 Eliminates Impairments in Hippocampal Long-Term Synaptic Plasticity:

If sustained elevation of COX-2 expression and activity following repeated $\Delta^9$-THC exposure contribute to impairments in long-term synaptic plasticity and cognitive function, then inhibition of COX-2 should be able to eliminate or attenuate the impairments. To test this hypothesis, we recorded hippocampal LTP in mice receiving daily injections of $\Delta^9$-THC (10 mg/kg, the dosage used by other studies, Fan et al., 2010; Hoffman et al., 2007; Puighermanal et al., 2009; Tonini et al., 2006), NS398, $\Delta^9$-THC+NS398 or vehicle for 7 consecutive days. We found that COX inhibition by NS398 rescued decreased hippocampal LTP induced by repeated in vivo exposure to $\Delta^9$-THC for 7 days both at CA3-CA1 synapses (FIG. 3A) and perforant path synapses in the dentate gyrus (FIG. 10A). Similarly, genetic inhibition of COX-2 also prevented LTP deterioration induced by $\Delta^9$-THC at both CA3-CA1 synapses (FIG. 3B) and the perforant path (FIG. 10B). To verify whether persistent over-expression of COX-2 impairs LTP, we recorded LTP in animals repeatedly treated with LPS, which increases COX-2. As we expected, repeated injection of LPS significantly reduced 1 LTP, and this decrease was prevented by inhibition of COX-2 (FIG. 10C). These data suggest that persistent elevation of COX-2 in the brain will be detrimental to integrity of synaptic structure and plasticity. Since a single dose of $\Delta^9$-THC produced an increase in COX-2 expression, we wondered whether this increase alters synaptic function. To this end, we recorded long-term depression (LTD) induced by low-frequency stimulation (LFS) at hippocampal CA3-CA1 synapses, and found that LTD is impaired by a single $\Delta^9$-THC exposure. However, LTD is normal in COX-2 knockout animals that received a single injection of $\Delta^9$-THC (FIG. 11). This information suggests that a single $\Delta^9$-THC exposure induces a COX-2-associated impairment in LTD (Mato et al., 2004; 2005).

Figure 4A:
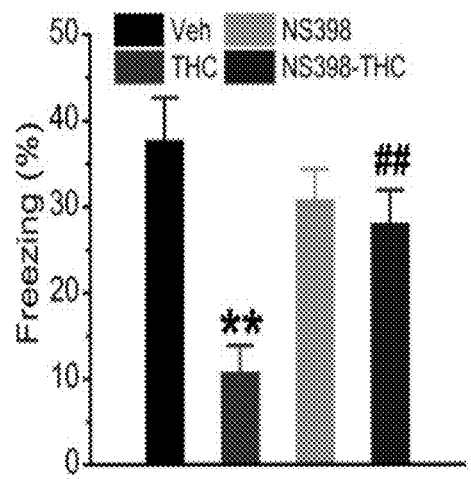
FIGS. 4A to 4C illustrate the impaired spatial and fear memories by repeated $\Delta^9$-THC exposure are occluded by COX-2 inhibition.
Figure 4B:
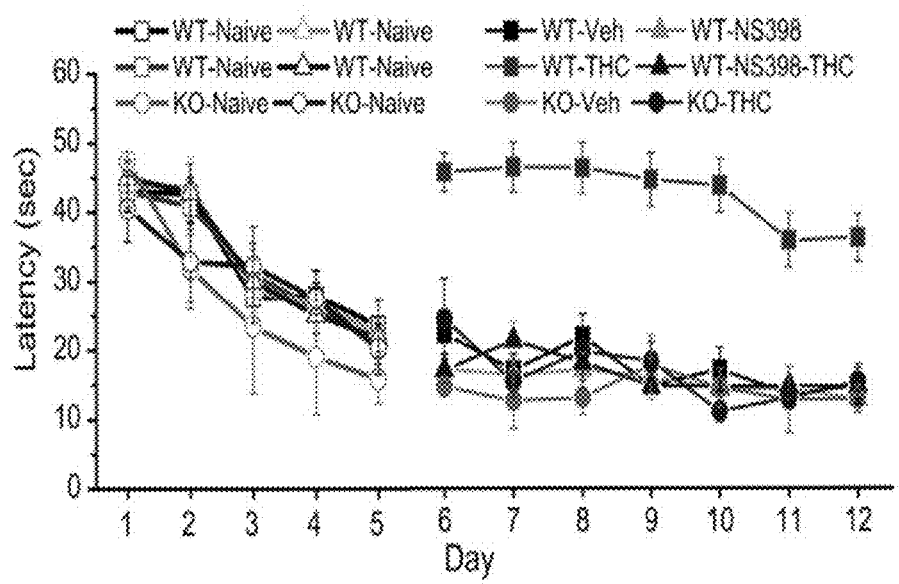
Figure 4C:
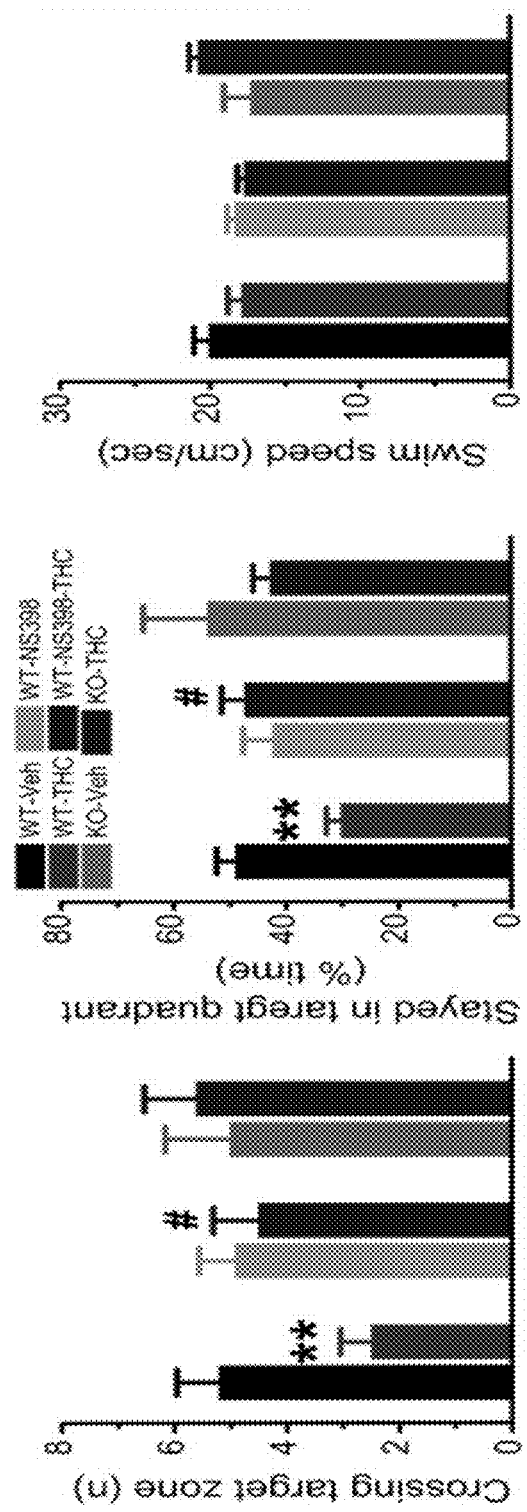

Impairments in Spatial and Fear Memory by $\Delta^9$-THC is Occluded by COX-2 Inhibition:

Administration of marijuana or $\Delta^9$-THC impairs learning and memory. If this impairment is associated with COX-2 induction, then inhibition of COX-2 would prevent or attenuate the deficits. To test this prediction, we determined the effect of COX-2 inhibition on spatial memory using the Morris water maze test in mice that received repeated $\Delta^9$-THC exposure in WT and COX-2 KO mice. As shown in FIGS. 4B & C, pharmacological or genetic inhibition of COX-2 prevented $\Delta^9$-THC-impaired spatial memory and memory retention. To further determine the role of COX-2 in $\Delta^9$-THC-impaired memory, hippocampus-dependent contextual memory was determined using the fear conditioning protocol (Chen et al., 2006). As seen in FIG. 4A, repeated $\Delta^9$-THC exposure impaired fear memory, and this impairment was attenuated by COX-2 inhibition. These results suggest that COX-2 plays a critical role in synaptic and cognitive function deterioration consequent to repeated in vivo $\Delta^9$-THC exposure (FIG. 14).

Figure 12B:
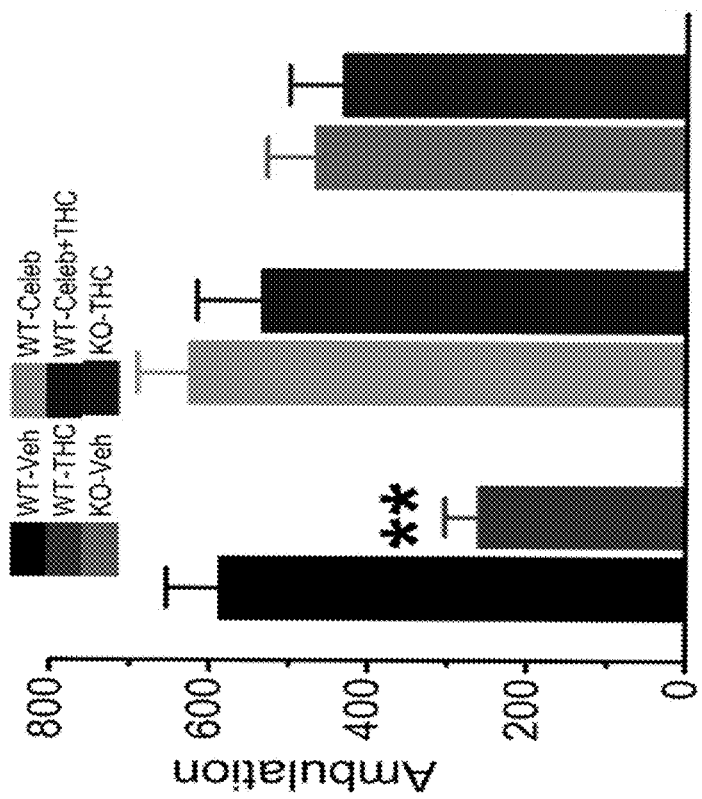
FIGS. 12A and 12B illustrate that $\Delta^9$-THC-induced cataleptic effect and locomotor depression are diminished by inhibition of COX-2, Related to FIG. 4.
Figure 12A:
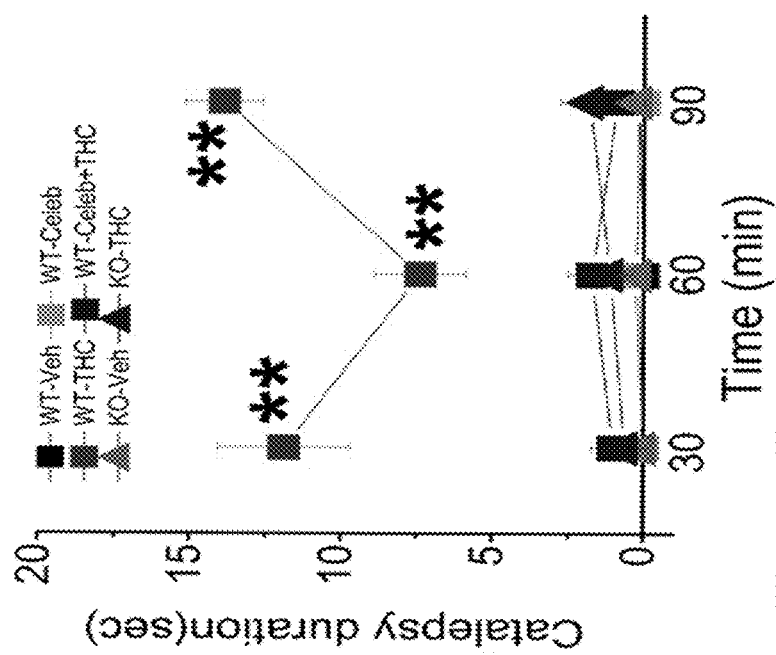

Cataleptic effect and hypomotility are behavioral response upon administering $\Delta^9$-THC (Burstein et al., 1989; Long et al., 2009). We observed that the cataleptic and locomotor depressive effects of $\Delta^9$-THC were attenuated or prevented by pharmacological or genetic inhibition of COX-2 (FIG. 12). This means that *cannabis*-elicited catalepsy and locomotor depression are associated with the COX-2 induction.

Figure 5A:
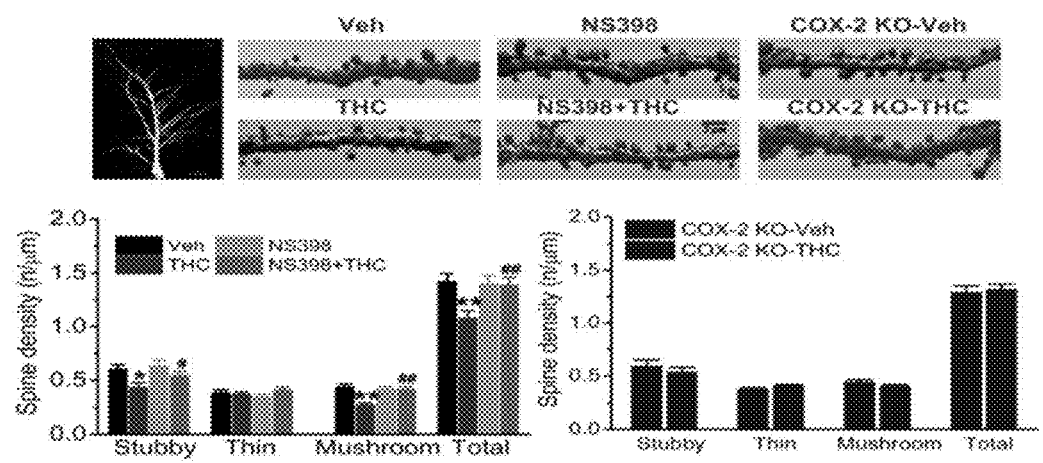
FIGS. 5A to 5D illustrate that decreases in dendritic spine density and glutamate receptor expression by $\Delta^9$-THC are prevented by inhibition of COX-2.
Figure 5B:
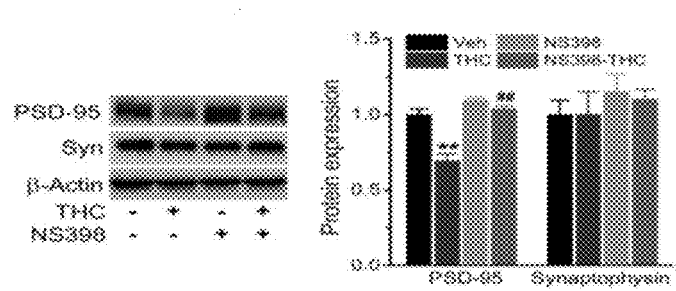
Figure 5C:
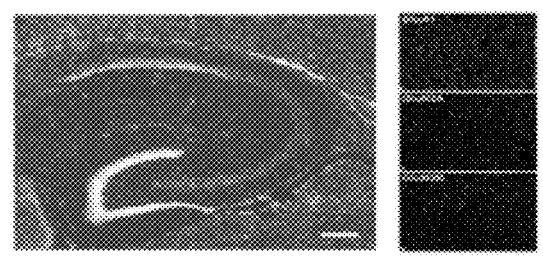
Figure 5D:
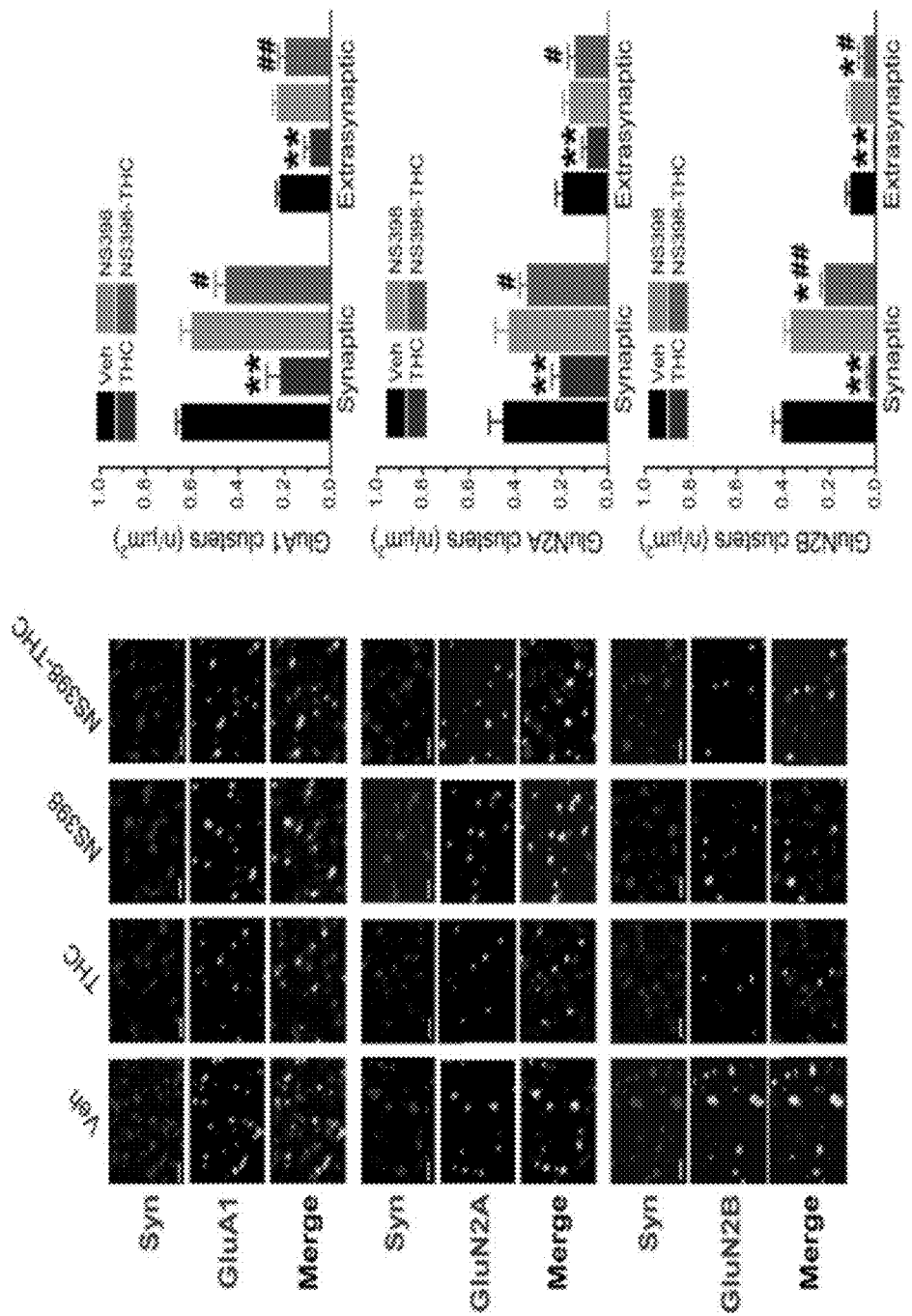
Figure 6A:
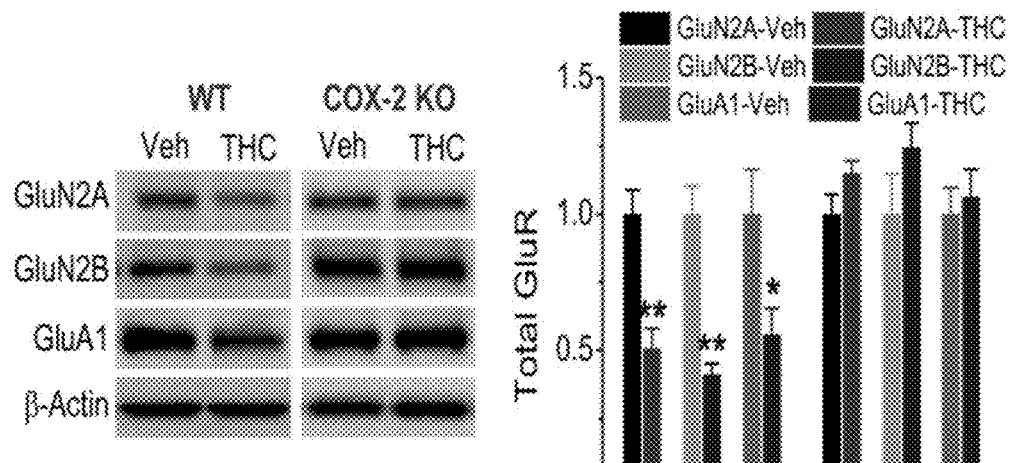
FIG. 6A to 6C illustrate a reduced expression of glutamate receptor subunits and phosphorylation of CREB by $\Delta^9$-THC is rescued by COX-2 inhibition.
Figure 6B:
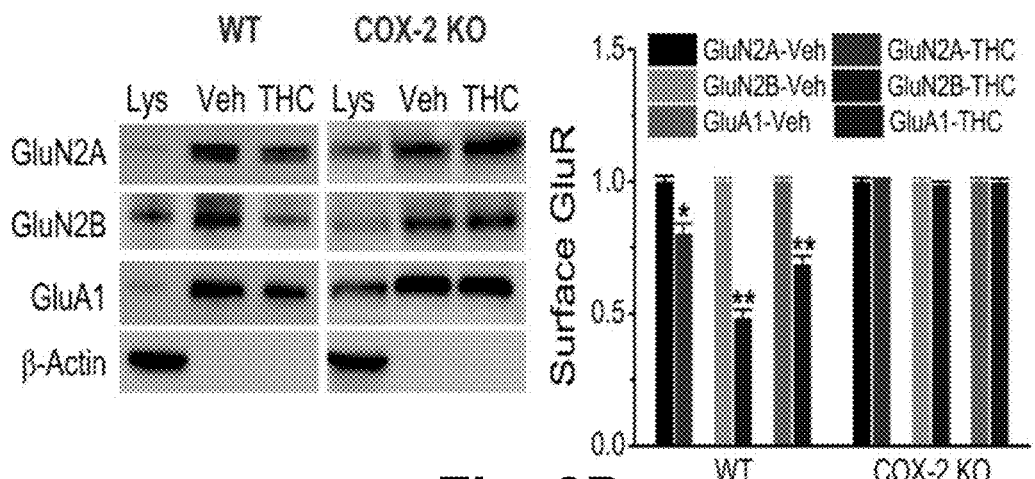
Figure 6C:
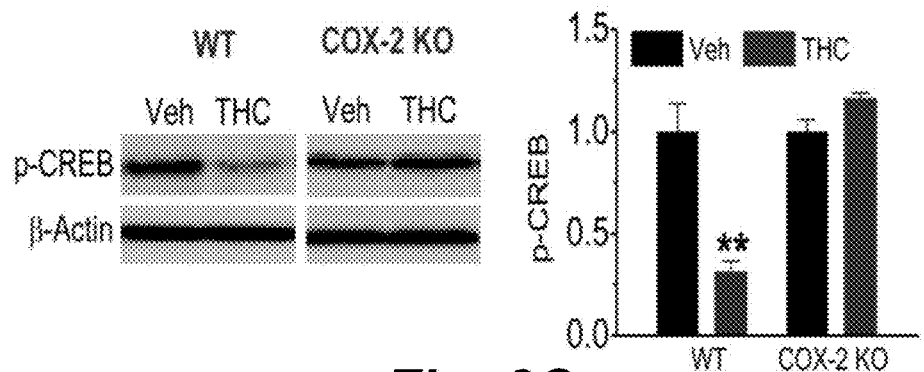
Figure 13A:
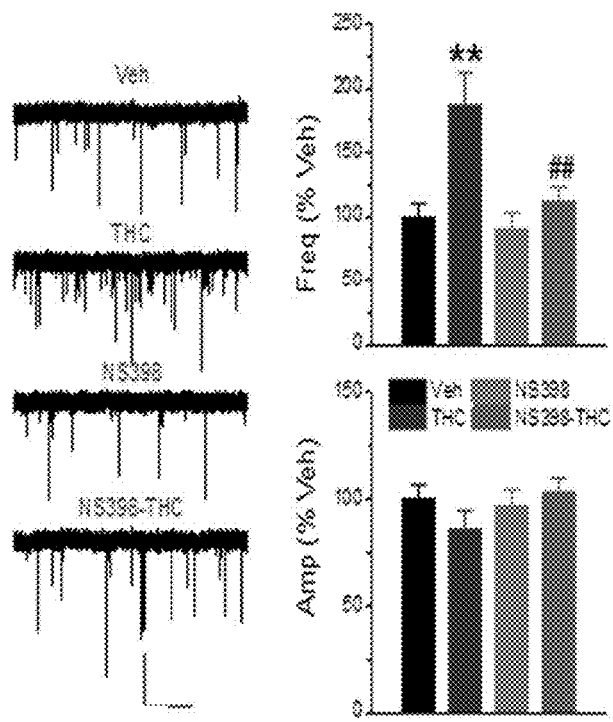
FIG. 13A illustrates that the $\Delta^9$-THC-enhanced synaptic release of glutamate is blocked by inhibition of COX-2, Related to FIGS. 5 & 6. Hippocampal neurons in culture were treated with vehicle, $\Delta^9$-THC (3 μM), NS398 (10 μM), and $\Delta^9$-THC+NS398. Miniature spontaneous EPSCs (mEPSCs) were recorded 24 hrs after treatments. Bicuculline (10 μM) and TTX (0.5 μM) were included in the external solution. Frequency and amplitude of mEPSCs were analyzed the MiniAnalysis program. Error bars present+SEM, $P<0.01$ compared with the vehicle control, ##$P<0.01$ compared with $\Delta^9$-THC (n=29 to 43 recordings, ANOVA, Bonferronni post-hoc test).
Figure 13B:
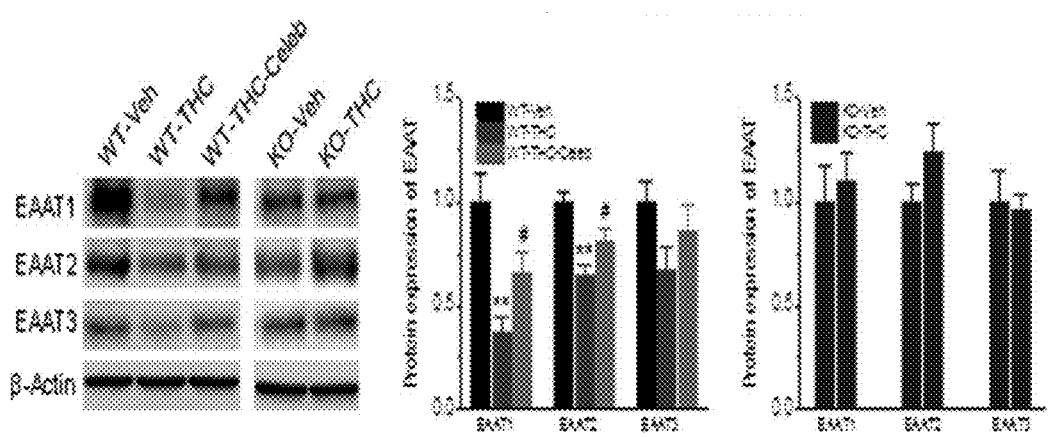
FIG. 13B illustrates that the reduced expression of glutamate transporters by $\Delta^9$-THC is blocked by COX-2 inhibition, Related to FIGS. 5 & 6. Hippocampal expression of glutamate transporters EAAT1, EAAT2, and EAAT3 in WT and COX-2 KO mice that received $\Delta^9$-THC (10 mg/kg) and $\Delta^9$-THC+Celebrex (10 mg/kg) once a day for 7 days. Immunoblot analysis was performed 24 hrs after cessation of the last injection. Error bars represent+SEM, $P<0.01$ compared with the vehicle control and #$P<0.05$ compared with A9-THC (ANOVA with Fisher's PLSD, n=3).

Functional Synaptic Integrity in $\Delta^9$-THC-Treated Animals is Maintained by COX-2 Inhibition:

Impaired long-term synaptic plasticity and memory induced by $\Delta^9$-THC are largely associated with altered expression and function of glutamate receptors (Fan et al., 2010; Han et al., 2012). Recent evidence shows that adolescent chronic treatment with $\Delta^9$-THC results in reduced density of dendritic spines and lowered length and number of dendrites in the hippocampus (Rubino et al., 2009). We used Thy1-GFP expressing transgenic mice to detect morphology of dendritic spines (Chen et al., 2012). As seen in FIGS. 5A & B, repeated $\Delta^9$-THC exposure significantly reduced density of dendritic spines of CA1 pyramidal neurons, especially mushroom spines where AMPA and NMDA receptors are expressed. We found that the reduction in spines was prevented by pharmacological or genetic inhibition of COX-2. (We should mention it here that the comparatively low number of mushroom-type spines in FIGS. 5A & B may be due to the scoring criteria). Meanwhile, $\Delta^9$-THC-reduced expression of PSD-95, an important postsynaptic marker, was rescued by COX-2 inhibition (FIG. 5C). However, $\Delta^9$-THC did not alter expression of synaptophysin (Syn), a presynaptic marker. This information indicates that increased COX-2 by repeated $\Delta^9$-THC exposure decreases dendritic spines and postsynaptic density. We show previously that repeated $\Delta^9$-THC exposure for 7 days induces CB1R-dependent decreases in functional and surface expression of AMPA and NMDA receptor subunits (Fan et al., 2010). We speculated that reduced expression of glutamate receptor subunits in the hippocampus of animals that received repeated in vivo $\Delta^9$-THC exposure are likely regulated by a homeostatic mechanism. $\Delta^9$-THC increased synthesis of COX-2 and its reaction product $PGE_2$, which stimulates glutamate released from presynaptic nerve terminals and astroglial cells, resulting in an extracellular accumulation of glutamate (FIG. 13A). The increased extracellular glutamate may also result from the reduced uptake of glutamate by glutamate transporters since expression of these transporters was down-regulated by repeated exposure to $\Delta^9$-THC (FIG. 13B). To this end, we used immunostaining to determine expressions of synaptic and extrasynaptic GluA1, GluN2A, GluN2B in the hippocampal CA1 area. As shown in FIG. 5D, hippocampal expressions of both synaptic and extrasynaptic GluA1, GluN2A, GluN2B were significantly reduced by repeated $\Delta^9$-THC exposure and the reduction was attenuated or prevented by COX-2 inhibition. This was consistent with the observations where total and surface expressions of GluA1, GluN2A, GluN2B detected by immunoblot in WT mice were significantly decreased following exposure to $\Delta^9$-THC for 7 days, but the decreases were not seen in COX-2 knockout mice (FIG. 6). These results indicate that reduced expression of glutamate receptor subunits and density of dendritic spines are associated with the COX-2 induction effect of $\Delta^9$-THC (FIG. 14).

Figure 7A:
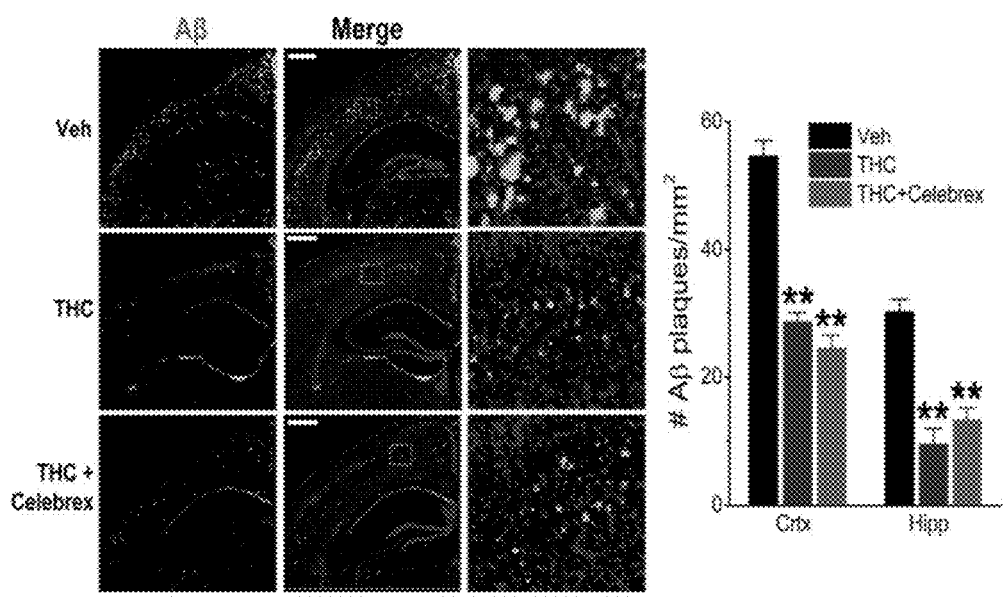
FIG. 7A to 7C illustrates the beneficial effects of reducing Aβ and neurodegeneration by $\Delta^9$-THC are preserved in the presence of COX-2 inhibition.
Figure 7B:
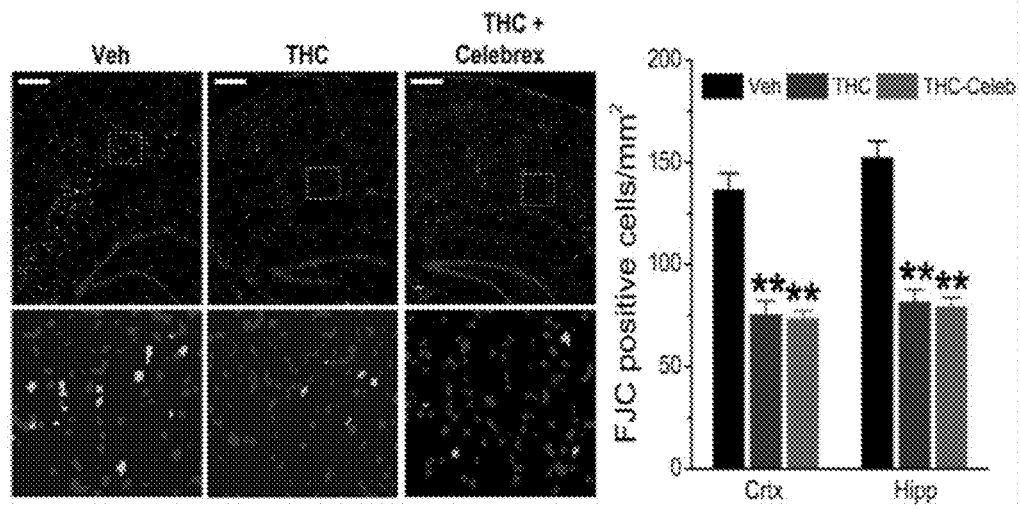
Figure 7C:
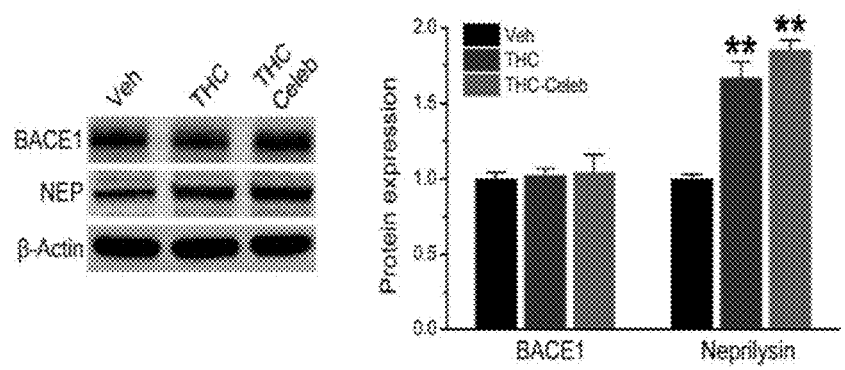

The Beneficial Effects of Decreasing Aβ and Neurodegeneration by $\Delta^9$-THC are Preserved in the Presence of COX-2 Inhibition:

An issue is whether COX-2 inhibition would eliminate the beneficial effects of marijuana. To answer this question, we used 5XFAD APP transgenic mice, an animal model of Alzheimer's disease (AD) as described previously (Chen et al., 2012), to determine whether $\Delta^9$-THC is capable of reducing Aβ and neurodegeneration and whether these effects are retained when COX-2 is inhibited. As shown FIGS. 7A & B, treatment of $\Delta^9$-THC once daily for four weeks significantly reduced the numbers of Aβ plaques and degenerated neurons in the absence and presence of Celebrex in AD animals. This information indicates that the beneficial effects of $\Delta^9$-THC are preserved while COX-2 is inhibited. Meanwhile, we revealed that the reduction of Aβ by $\Delta^9$-THC is not through inhibiting expression of β-site amyloid precursor protein cleaving enzyme 1 (BACE1), an enzyme responsible for synthesis of Aβ, but likely through elevating neprilysin, an important endopeptidase that degrades Aβ (FIG. 7C).

Discussion:

The results presented here demonstrate that impaired synaptic and cognitive function induced by repeated $\Delta^9$-THC exposure is associated with a previously unrevealed CB1R-Gβγ-Akt-ERK/MAPK-NF-κB-COX-2 signaling pathway. It has been long known that use of marijuana induces neuropsychiatric and cognitive deficits, which greatly limit medical use of marijuana. Synaptic and memory impairments are also the consequence of *cannabis* abuse. However, the molecular mechanisms underlying undesirable effects by *cannabis* are largely unknown. We discovered in this study that pharmacological or genetic inhibition of COX-2 eliminates or attenuates synaptic and memory impairments elicited by repeated $\Delta^9$-THC exposure, suggesting that these major adverse effects of *cannabis* on synaptic and cognitive function can be eliminated by COX-2 inhibition, which would broaden the use of medical marijuana.

CB1R is the primary target of cannabinoid exposures causing synaptic and memory impairments (Lichtman and Martin, 1996; Hoffman et al., 2007; Puighermanal et al., 2009; Fan et al., 2010; Han et al., 2012). Previous studies show that the endocannabinoid 2-AG suppresses COX-2 via a CB1R-dependent mechanism in response to proinflammatory and excitotoxic insults (Zhang and Chen, 2008). Surprisingly, we found in the present study that the exogenous cannabinoid $\Delta^9$-THC increases COX-2 activity and expression, which are also mediated via CB1R. We demonstrate that COX-2 induction by $\Delta^9$-THC is mediated via Gβγ subunits, while COX-2 suppression by 2-AG is mediated via the Gαi1 subunit, suggesting that activation of the same CB1 receptor may induce opposite biological effects. Indeed, previous studies showed that endogenous cannabinoids and exogenous $\Delta^9$-THC exhibit different behavioral responses via CB1R (Long et al., 2009). However, it is still not clear how activation of CB1R and its coupled Gi/o by the endogenous cannabinoid 2-AG results in Gαi-mediated suppression of COX-2 in response to proinflammatory insults but by the exogenous cannabinoid $\Delta^9$-THC leads to Gβγ-mediated induction of COX-2. Activation of CB1R/Gi/o either by 2-AG or $\Delta^9$-THC should induce both Gαi- and Gβγ-mediated effector responses through different downstream signaling events. For example, inhibition of N-type calcium channel currents by 2-AG appears to be mediated via Gβγ (Guo and Ikeda, 2004), suggesting that 2-AG is also capable of triggering Gβγ-mediated responses in addition to Gαi-mediated responses. In the case of COX-2 induction, the Gβγ-mediated COX-2 induction by $\Delta^9$-THC may be predominant, which may mask Gαi-mediated COX-2 suppression. In addition, our results showing that the beneficial effects of $\Delta^9$-THC are retained in the presence of COX-2 inhibition further suggest that activation of CB1R by $\Delta^9$-THC may have both Gαi- and Gβγ-mediated effector responses. It is likely that COX-2 induction by $\Delta^9$-THC may be just one of several Gβγ-mediated effects, and we cannot exclude the possibility that other biological effects are mediated via Gβγ. The divergent roles of G-protein subunits in mediating endogenous and exogenous cannabinoids may be a consequence the intrinsic mechanisms of CB1R/G-protein coupling, such as the agonist binding sites in the receptor, the efficacy of binding, or different conformational changes in the receptor/G-protein upon binding with different agonists.

Synaptic and cognitive impairments by $\Delta^9$-THC are apparently associated with alterations in glutamatergic synaptic transmission and functional expression of glutamate receptor subunits (Fan et al., 2010; Han et al., 2012; Monory et al., 2007; Tonini et al., 2006). It has been demonstrated that cannabinoid exposure leads to down-regulation, internalization, and endocytosis of glutamate receptor subunits (Fan et al., 2010; Han et al., 2012; Suarez et al., 2003). In this study, we also demonstrate that density of dendritic spines in hippocampal neurons is reduced in animals that received $\Delta^9$-THC for seven days. The reduced expressions of synaptic and extrasynaptic of glutamate receptor subunits as well as PSD-95 by $\Delta^9$-THC are likely associated with elevated extracellular glutamate levels. Indeed, it has been shown that cannabinoids elevate extracellular glutamate levels, which may result from increased synaptic and astrocytic release of glutamate or reduced uptake of glutamate by glutamate transporters (Fan et al., 2010; Ferraro et al., 2001; Han et al., 2012; Navarrete et al., 2008; Tomasini et al., 2002; Suarez et al., 2004; Tonini et al., 2006). We detected that expression of glutamate transporters is significantly decreased in $\Delta^9$-THC exposed animals, and this decrease is attenuated by COX-2 inhibition (FIG. 13). These previous studies together with our results suggest that accumulation of glutamate in the extracellular apartment by repeated $\Delta^9$-THC exposure contributes to reductions in total and surface expression of the glutamate receptors and the density of dendritic spines.

Earlier studies showed that the levels of the eicosanoid $PGE_2$ in circulation and the brain are elevated in humans and animals exposed to marijuana or $\Delta^9$-THC and the elevation could be antagonized by indomethacin, an NSAID (Burstein et al., 1989; Fairbairn and Pickens, 1979; 1980; Perez-Reyes et al., 1991). NSAIDs are non-selective inhibitors for both COX-1 and COX-2. This suggests that COX-1 and/or COX-2 may be involved in marijuana- or $\Delta^9$-THC-induced increase in $PGE_2$. While both COX-1 and COX-2 are capable of converting arachidonic acid (AA) into five primary prostanoids and prostaglandins ($PGD_2$, $PGE_2$, $PGF_2\alpha$, $PGI_2$, and $TXA_2$), they exhibit preferences in synthesizing these substances. It is evident that $PGE_2$ is primarily derived from the COX-2 pathway (Brock et al., 1999; Sang et al., 2005). Since COX-1 expression is not affected by $\Delta^9$-THC (FIG. 8) and COX-2 is expressed both in constitutive and inducible forms in the brain, it is likely that COX-2 is responsible for the marijuana- or Δ9-THC-induced elevation of $PGE_2$. Our data showing that $\Delta^9$-THC increases $PGE_2$ in the brain and this increase is blocked by COX-2 inhibition support this speculation. Interestingly, $\Delta^9$-THC-induced cataleptic response can be eliminated by NSAIDs and mimicked by direct administration of $PGE_2$ (Burstein et al., 1989; Fairbairn and Pickens, 1979). We also provide convincing evidence that pharmacological or genetic inhibition of COX-2 prevents or attenuates cataleptic and locomotor depressive responses by Δ9-THC. Importantly, synaptic and cognitive deficits following repeated $\Delta^9$-THC exposure are eliminated or attenuated by COX-2 inhibition.

The elevated levels of extracellular glutamate by $\Delta^9$-THC result likely from induction of COX-2, which makes $PGE_2$. It has been shown that $PGE_2$ stimulates or facilitates both synaptic and astrocytic release of glutamate (Bezzi et al., 1998; Chen et al., 2002; Dave et al., 2010; Sang et al., 2005; Sanzgiri et al., 1999). In fact, COX-2 and $PGE_2$ signaling have been shown to regulate glutamatergic synaptic transmission and plasticity via EP2 or EP3 receptors (Akaneya and Tsumoto, 2006; Chen et al., 2002; Cowley et al., 2008; Sang et al., 2005). It is possible that $\Delta^9$-THC exposure stimulates COX-2 expression and activity through CB1R-coupled Gβγ subunits and downstream Akt-ERK/MAPK-NF-κB signaling pathway, resulting in increase of COX-2 transcription, expression, and activity, which in turn enhance the release of $PGE_2$ from neurons and astroglial cells. Our results show that $\Delta^9$-THC-induced COX-2 expression in astroglial cells is more pronounced than that in neurons. A recent study also shows that CB1R expressed in astroglial cells is responsible for LTD and working memory impairment in animals exposed to cannabinoids (Han et al., 2012). This suggests that glutamate released from astroglial cells triggered by COX-2-derived $PGE_2$ and reduced uptake of glutamate by glutamate transporters in astrocytes resulting from repeated $\Delta^9$-THC exposure may play an important role in extracellular glutamate accumulation. Sustained elevation and accumulation of extracellular glutamate upon repeated exposure to $\Delta^9$-THC induce downregulation and internalization of glutamate receptor subunits and reduction in the density of dendritic spines in hippocampal neurons, leading to the deficits in long-term synaptic plasticity and cognitive function (FIG. 14).

It has been well recognized that cannabinoids possess antioxidant, anti-inflammatory, and neuroprotective properties (Bahr et al., 2006; Campbell and Gowran, 2007; Centonze et al., 2007; Chen et al., 2011; Du et al., 2011; Gowran et al., 2011; Marchalanta et al., 2008; Marsicano et al., 2003; Zhang and Chen, 2008). Also *cannabis* has been used for thousands of years as medical treatments. However, neuropsychiatric and cognitive side effects limit medical use of marijuana, especially for a long-term treatment. The results presented here suggest that the unwanted side effects of *cannabis* could be eliminated or reduced, while retaining its beneficial effects, by administering a COX-2 inhibitor or NSAID along with $\Delta^9$-THC for treatments of intractable medical conditions such as Alzheimer's disease (AD). In the present study, we did observe that brain Aβ and neurodegeneration in 5XFAD transgenic mice are significantly reduced by $\Delta^9$-THC and these beneficial effects are preserved in the presence of COX-2 inhibition. We also discovered that $\Delta^9$-THC significantly elevates expression of neprilysin, an important endopeptidase for Aβ degradation. This suggests that $\Delta^9$-THC is capable of reducing Aβ and neurodegeneration in an animal model of AD and that the Aβ reducing effect is likely through elevating expression of neprilysin. This suggests that $\Delta^9$-THC (brand name: Marinol) may have therapeutic potential for prevention and treatment of Alzheimer's disease if its undesirable side effects (e.g., synaptic and cognitive impairments) can be eliminated by COX-2 inhibition. In particular, there are no effective medications currently available for preventing and treating AD or halting disease progression. Our results also suggest that selective COX-2 inhibitors or NSAIDs may be useful for treating the neuropsychological and cognitive side effects of *cannabis* abuse.

Experimental Procedures

Animals:

C57BL/6, CB1 knockout, Thy1-EGFP transgenic, COX-2 knockout and 5XFAD APP transgenic mice were used in the present study.

Cell Culture:

Relative pure hippocampal neurons (astroglial cells<2%), mixed neurons and astroglial cells (astroglial cells ~10%), and astroglial cell-enriched (astroglial cells>95%), and NG108-15 cell cultures were made as described previously (Sang et al, 2005; Zhang and Chen, 2008).

Electrophysiological Recordings:

Hippocampal LTP both at CA3-CA1 and perforant path synapses were recorded in acutely hippocampal slices and induced by a theta-burst stimulation (TBS) as described previously (Hoffman et al., 2007).

Immunoblots:

Western blot assay was conducted using specific antibodies (Table S1) to determine expressions of COX-2, glutamate receptor subunits, PSD-95, G-protein subunits, phosphoproteins, BACE1 and neprilysin in hippocampal tissue and/or in cultured cells as described previously (Chen et al., 2012). Surface biotinylation assays were performed to determine surface expression of glutamate receptor subunits in hippocampal slices as described previously (Fan et al., 2010).

Transfection of Plasmid and Lentiviral Vectors:

NG108-15 cells were used for transfection of the pcDNA3.1 plasmid encoding Gβ1 and Gγ2 subunits or the pLL3.7 vector expressing scramble, Gβ1 and Gγ2 shRNA, and shRNA-resistant Gβ1γ2. Mixed culture of neurons and astroglial cells were used for transfection of the pLL3.7 lentiviral vector expressing scramble, Gαi1 shRNA, and shRNA-resistant Gαi1.

qRT-PCR.

The iScript cDNA synthesis kit (BioRad) was used for the reverse transcription reaction. Real-time RT-PCR specific primers for COX-2, β1, γ2, and GAPDH were synthesized by IDT (Coralville, Iowa). Samples were compared using the relative CT method as described previously (Zhang & Chen, 2008).

CHIP Analysis:

Chromatin Immunoprecipitation (ChIP) analysis was performed to determine the binding activity of NF-κB in the promoter of the COX-2 gene.

PGE$_2$ Assay:

PGE$_2$ in hippocampal tissue was detected using PGE$_2$ enzyme immunoassay kit (Cayman Chemical, Ann Arbor, Mich.) according to the procedure described by the manufacturer (Zhang and Chen, 2008).

Immunostaining and Histochemistry:

Aβ plaques, degenerated neurons, and glutamate receptor subunits in cryostat sectioning brain slices were performed as described previously (Chen et al., 2012; Li et al., 2011).

Two-Photon Imaging:

Morphology of dendritic spines in hippocampal CA1 pyramidal neurons was determined in GFP-expressing transgenic mice using a two-photon laser scanning microscope as described previously (Chen et al., 2012). Shape, size, and density of spines were measured from the three-dimensional reconstructions using NeuronStudio Version 0.9.92.

Behavioral Tests:

The classic Morris water maze and fear conditioning tests were performed to determine spatial and fear memory as described previously (Chen et al., 2012). The 'open field' test was conducted to detect the locomotor activity and the bar test was used to detect catalepsy (Egashira et al., 2007).

REFERENCES FOR EXAMPLE 1

Alger, B. E. (2009). Endocannabinoid signaling in neural plasticity. Curr Top Behav Neurosci 1, 141-172.

Akaneya Y, Tsumoto T. (2006). Bidirectional trafficking of prostaglandin E2 receptors involved in long-term potentiation in visual cortex. J. Neurosci. 26, 10209-10221.

Bahr, B. A., Karanian, D. A., Makanji, S. S., and Makriyannis, A. (2006). Targeting the endocannabinoid system in treating brain disorders. Expert Opin Investig Drugs. 15, 351-365.

Bezzi, P., Carmignoto, G., Pasti, L., Vesce, S., Rossi, D., Rizzini, B. L., Pozzan, T., and Volterra, A. (1998). Prostaglandins stimulate calcium-dependent glutamate release in astrocytes. Nature 391, 281-285.

Brock, T. G., McNish, R. W., and Peters-Golden, M. (1999). Arachidonic acid is preferentially metabolized by cyclooxygenase-2 to prostacyclin and prostaglandin E2. J. Biol. Chem. 274, 11660-11666.

Burstein, S. H., Hull, K., Hunter, S. A., and Shilstone, J. (1989). Immunization against prostaglandins reduced Δ1-tetrahydrocannabinol-induced catalepsy in mice. Mol. Pharmacol. 35, 6-9.

Campbell, V. A., and Gowran, A. (2007). Alzheimer's disease: taking the edge off with cannabinoids? Br. J. Pharmacol. 152, 655-662.

Carlini, E. A. (2004). The good and the bad effects of (−) trans-delta-9-tetrahydrocannabinol ($\Delta^9$-THC) on humans. Toxicon 44, 461-467.

Centonze, D., Finazzi-Agro, A., Bernardi, G., and Maccarrone, M. (2007). The endocannabinoid system in targeting inflammatory neurodegenerative diseases. Trends in Pharmacol. Sci. 28, 180-187.

Chen, C., Magee, J. C., and Bazan, N. G. (2002). Cyclooxygenase-2 regulates prostaglandin E$_2$ signaling in hippocampal long-term synaptic plasticity. J. Neurophysiol. 87, 2851-2857.

Chen, C., Hardy, M., Zhang, J., LaHoste, G. J., and Bazan, N. G. (2006). Altered NMDA receptor trafficking contributes to sleep deprivation-induced hippocampal synaptic and cognitive impairments. Biochem. Biophys. Res. Commun. 340, 435-440.

Chen, X., Zhang, J., and Chen, C. (2011). Endocannabinoid 2-arachidonoylglycerol protects neurons against β-amyloid insults. Neurosci. 178, 159-168.

Chen, R., Zhang, J., Wu, Y., Wang, D., Feng, G., Tang, Y. P., Teng, Z., and Chen, C. (2012). Monoacylglycerol lipase is a therapeutic target for Alzheimer's disease. Cell Reports 2, 1329-1339.

Chevaleyre, V., Takahashi, K. A., and Castillo, P. E. (2006). Endocannabinoid-Mediated Synaptic Plasticity in the CNS. Ann. Rev. Neurosci 29, 37-76.

Cowley, T. R., Fahey, B., and O'Mara, S. M. (2008). COX-2, but not COX-1, activity is necessary for the induction of perforant path long-term potentiation and spatial learning in vivo. Eur. J. Neurosci. 27, 2999-3008.

Dave, K. A., Platel, J. C., Huang, F., and Tian, D., Stamboulian-Platel, S., Bordey, A. (2010) Prostaglandin E2 induces glutamate release from subventricular zone astrocytes. Neuron Glia Biol. 6, 201-207.

Delaney, A. J., Crane, J. W., and Sah, P. (2007). Noradrenaling modulates transmission at a central synapse by a presynaptic mechanism. Neuron 56, 880-892.

Du, H., Chen, X., Zhang, J., and Chen, C. (2011) Inhibition of COX-2 expression by endocannabinoid 2-arachidonoylglycerol is mediated by PPAR-γ. Br. J. Pharmacol. 163, 1533-1549.

Egashira, N., Koushi, E., Mishima, K., Iwasaki, K., Oishi, R., and Fujiwara, M. (2007). 2,5-Dimethoxy-4-iodoamphetamine (DOI) inhibits Delta9-tetrahydrocannabinol-induced catalepsy-like immobilization in mice. J. Pharmacol. Sci. 105, 361-366.

Fairbairn, J. W., and Pickens, J. T. (1979). The oral activity of A'-tetrahydrocannabinol and its dependence on prostaglandin $E_2$. Br. J. Pharmacol. 67, 379-385.

Fairbairn, J. W., and Pickens, J T. (1980). The effect of conditions influencing endogenous prostaglandins on the activity of delta'-tetrahydrocannabinol in mice. Br. J. Pharmacol. 69, 491-493.

Fan, N., Yang, H., Zhang, J., and Chen, C. (2010). Reduced expression of glutamate receptors and phosphorylation of CREB are responsible for in vivo $\Delta^9$-THC exposure-impaired hippocampal synaptic plasticity. J. Neurochem. 112, 691-702.

Ferraro, L., Tomasini, M. C., Gessa, G. L., Bebe, B. W., Tanganelli, S., and Antonelli, T. (2001). The cannabinoid receptor agonist WIN 55, 212-2 regulates glutamate transmission in rat cerebral cortex: an in vivo and in vitro study. Cereb. Cortex 11, 728-733.

Gaoni, Y., and Mechoulam, R. (1964). Isolation, structure and partial synthesis of an active constituent of hashish. J. Am. Chem. Soc. 86, 1646-1647.

Goubaeva, F., Ghosh, M., Malik, S., Yang, J., Hinkle, P. M., Griendling, K. K., Neubig R. R., and Smrcka, A. V. (2003). Stimulation of cellular signaling and G protein subunit dissociation by G protein betagamma subunit-binding peptides. J. Biol. Chem. 278, 19634-19641.

Gowran, A., Noonan, J., Campbell, V. A. (2011). The multiplicity of action of cannabinoids: implications for treating neurodegeneration. CNS Neurosci. Ther. 17, 637-644.

Guo, J., and Ikeda, S. R. (2004). Endocannabinoids modulate N-type calcium channels and G-protein-coupled inwardly rectifying potassium channels via CB1 cannabinoid receptors heterologously expressed in mammalian neurons. Mol Pharmacol. 65, 665-674.

Han, J., Kesner, P., Metna-Laurent, M., Duan, T., Xu, L., Georges, F., Koehl, M., Abrous, D. N., Mendizabal-Zubiaga, J., Grandes, P., et al. (2012). Acute cannabinoids impair working memory through astroglial CB1 receptor modulation of hippocampal LTD. Cell 148, 1039-1050.

Hoffman, A. F., Oz. M., Yang, R., Lichtman, A. H., and Lupica, C. R. (2007). Opposing actions of chronic Delta$^9$-tetrahydrocannabinol and cannabinoid antagonists on hippocampal long-term potentiation. Learn. Mem. 14, 63-74.

Howlett, A. C. (1998). The CB1 cannabinoid receptor in the brain. Neurobiol. Dis. 5, 405-416.

Kano, M., Ohno-Shosaku, T., Hashimotodani, Y., Uchigashima, M., and Watanabe, M. (2009). Endocannabinoid-mediated control of synaptic transmission. Physiol. Rev. 89, 309-380.

Li, S., Jin, M., Koeglsperger, T., Shepardson, N. E., Shankar, G. M., Selkoe, D. J. (2011). Soluble Aβ oligomers inhibit long-term potentiation through a mechanism involving excessive activation of extrasynaptic NR2B-containing NMDA receptors. J. Neurosci. 31, 6627-6638.

Lichtman, A. H., and Martin, B. R. (1996). Delta 9-tetrahydrocannabinol impairs spatial memory through a cannabinoid receptor mechanism. Psychopharm. (Berl) 126, 125-131.

Long, J. Z., Nomura, D. K., Vann, R. E., Walentiny, D. M., Booker, L., Jin, X., Burston, J. J., Sim-Selley, L. J., Lichtman, A. H., Wiley, J. L., et al. (2009). Dual blockade of FAAH and MAGL identifies behavioral processes regulated by endocannabinoid crosstalk in vivo. Proc. Natl. Acad. Sci. USA 106, 20270-20275.

Lovinger, D. M. (2008). Presynaptic modulation by endocannabinoids. Handb. Exp. Pharmacol. 184, 435-477.

Marchalanta, Y., Brothersa, H. M., and Wenka, G. L. (2008). Inflammation and aging: can endocannabinoids help? Biomed. Pharmacother. 62, 212-217.

Marsicano, G., Goodenough, S., Monory, K., Hermann, H., Eder, M., Cannich, A., Azad, S. C., Cascio, M. G., Gutierrez, S. O., van der Stelt, M., et al. (2003). CB1 cannabinoid receptors and on-demand defense against excitotoxicity. Science 302: 84-88.

Mato, S., Chevaleyre, V., Robbe, D., Pazos, A., Castillo, P. E., and Manzoni, O. J. (2004). A single in-vivo exposure to delta 9THC blocks endocannabinoid-mediated synaptic plasticity. Nat. Neurosci. 7, 585-586.

Mato, S., Robbe, D., Puente, N., Grandes, P., and Manzoni, O. J. (2005). Presynaptic homeostatic plasticity rescues long-term depression after chronic Delta 9-tetrahydrocannabinol exposure. J. Neurosci. 25, 11619-11627.

Messinis, L., Kyprianidou, A., Malefaki, S., and Papathanasopoulos, P. (2006). Neuropsychological deficits in long-term frequent *cannabis* users. Neurol. 66, 737-739.

Monory, K., Blaudzun, H., Massa, F., Kaiser, N., Lemberger, T., Schutz, G., Wotjak, C. T., Lutz, B., and Marsicano, G. (2007). Genetic dissection of behavioural and autonomic effects of Delta (9)-tetrahydrocannabinol in mice. PLoS Biol. 5:e269.

Navarrete, M., and Araque, A. (2008). Endocannabinoids mediate neuron-astrocyte communication. Neuron 57, 883-893.

Panikashvili, D., Simeonidou, C., Ben-Shabat, S., Hanus, L., Breuer, A., Mechoulam, R. and Shohami, E. (2001). An endogenous cannabinoid (2-AG) is neuroprotective after brain injury. Nature 413, 527-531.

Perez-Reyes, M., Burstein, S. H., White, W. R., McDonald, S. A., and Hicks, R. E. (1991). Antagonism of marijuana effects by indomethacin in human. Life Sci. 48, 507-515.

Pertwee, R. G., Howlett, A. C., Abood, M. E., Alexander, S. P., Di Marzo, V., Elphick, M. R., Greasley, P. J., Hansen, H. S., Kunos, G., Mackie, K., et al. (2010). International Union of Basic and Clinical Pharmacology. LXXIX. Cannabinoid receptors and their ligands: beyond $CB_1$ and $CB_2$. Pharmacol. Rev. 62:588-631.

Pope, H. G., Gruber, A. J., Hudson, J. I., Huestis, M. A., and Yurgelun-Todd, D. (2001). Neuropsychological performance in long-term *cannabis* users. Arch. Gen. Psychiatry 58, 909-915.

Puighermanal, E., Marsicano, G., Busquets-Garcia, A., Lutz, B., Maldonado, R., and Ozaita, A. (2009). Cannabinoid modulation of hippocampal long-term memory is mediated by mTOR signaling. Nat. Neurosci. 12, 1152-1158.

Robson, P. (2001). Therapeutic aspects of *cannabis* and cannabinoids. Br. J. Psychiatry 178, 107-115.

Rubino, T., Realini, N., Braida, D., Guidi, S., Capurro, V., Vigano, D., Guidali, C., Pinter, M., Sala, M., Bartesaghi, R., et al. (2009). Changes in hippocampal morphology and neuroplasticity induced by adolescent THC treatment are associated with cognitive impairment in adulthood. Hippocampus 19, 763-772.

Russo, E. B. (2007). History of *Cannabis* and Its Preparations in Saga, Science, and Sobriquet. Chem. Biodiv. 4, 1614-1648.

Sang, N., Zhang, J., Marcheselli, V., Bazan, N. G., and Chen, C. (2005). Postsynaptically synthesized prostaglandin E2 modulates hippocampal synaptic transmission via a presynaptic $PGE_2$ EP2 receptor. J. Neurosci. 25, 9858-9870.

Sanzgiri, R. P., Araque, A., Haydon, P. G. (1999). Prostaglandin E(2) stimulates glutamate receptor-dependent astrocyte neuromodulation in cultured hippocampal cells. J. Neurobiol. 41, 221-229.

Solowij, N., Stephens, R. S., Roffman, R. A., Babor, T., Kadden, R., Miller, M., Christiansen, K., McRee, B., and Vendetti, J. (2002). Marijuana Treatment Project Research Group. Cognitive functioning of long-term heavy *cannabis* users seeking treatment. J. Am. Med. Assoc. 287, 1123-1131.

Suárez, I., Bodega, G., Fernandez-Ruiz, J., Ramos, J. A., Rubio, M., and Fernandez, B. (2003). Down-regulation of the AMPA glutamate receptor subunits GluR1 and GluR2/3 in the rat cerebellum following pre- and perinatal $\Delta^9$-tetrahydrocannabinol exposure. Cerebellum 2, 66-74.

Suárez, I., Bodega, G., Rubio, M., Fernandez-Ruiz, J. J., Ramos, J. A., and Fernandez, B. (2004). Prenatal cannabinoid exposure down-regulates glutamate transporter expressions (GLAST and EAAC1) in the rat cerebellum. Dev. Neurosci. 26, 45-53.

Teather, L. A., Packard, M. G., and Bazan, N. G. (2002). Post-training cyclooxygenase-2 (COX-2) inhibition impairs memory consolidation. Learn Mem. 9, 41-47.

Tomasini, M. C., Ferraro, L., Bebe, B. W., Tanganelli, S., Cassano, T., Cuomo, V., and Antonelli, T. (2002). $\Delta^9$-Tetrahydrocannabinol increases endogenous extracellular glutamate levels in primary cultures of rat cerebral cortex neurons: involvement of CB1 receptor. J. Neurosci. Res. 68, 449-453.

Tonini, R., Ciardo, S., Cerovic, M., Rubino, T., Parolaro, D., Mazzanti, M., and Zippel, R. (2006). ERK-dependent modulation of cerebellar synaptic plasticity after chronic Δ9-tetrahydrocannabinol exposure. J Neurosci. 26, 5810-5818.

Wilson, R. I., Kunos, G., Nicoll, R. A. (2001). Presynaptic specificity of endocannabinoid signaling in the hippocampus. Neuron 31, 453-462.

Yao, L., Fan, P., Jian, Z., Mailliard, W. S., Gordon, A. S., and Diamond, I. (2003). Addicitng drugs utilize a synergistic molecular mechanism in common requiring adenosine and Gi-βγ dimmers. Proc. Natl. Acad. Sci. USA 100, 14379:14384.

Zhang, J., and Chen, C. (2008). Endocannabinoid 2-arachidonoylglycerol protects neurons by limiting COX-2 elevation. J. Biol. Chem. 283, 22601-22611.

Additional Information for Example 1

Experimental Procedures

Animals:

C57BL/6 (Charles River, Wilmington, Mass.), CB1 knockout (KO) mice (cnr1$^{(-/-)}$, NIMH transgenic core, NIH, Bethesda, Md.), neuronal expressing EGFP transgenic mice (Thy1-EGFP)MJrs/J, Jackson Lab), and COX-2 knockout mice (B6; 1295-Ptgs2tm1Jed/J, Jackson Lab) at ages of 6 to 9 weeks were used in the present study. The care and use of the animals reported in this study were approved by the Institutional Animal Care and Use Committee of Louisiana State University Health Sciences Center. 5XFAD APP transgenic mice (Jackson Lab) were used at ages of 4 to 6 months (Chen et al., 2012; Oakley et al., 2006). For two-photon imaging, EGFP-expressing mice were used (B6, cg-Tg (Thy1-EGFP)MJrs/J, Jackson Lab). COX-2 KO mice were bred with EGFP-expressing mice to get COX-2 KO-GFP expressing transgenic mice (Chen et al., 2012). Age-matched littermates (either sex) were used in all the studies. The care and use of the animals reported in this study were approved by the Institutional Animal Care and Use Committee of Louisiana State University Health Sciences Center. Mice were intraperitoneally (i.p.) injected with vehicle, $\Delta^9$-THC, Rimonabant (RIM), Celebrex (Celeb), or NS398 (Cayman Chemical, MI). Animals received repeated administrations of $\Delta^9$-THC once a day for 7 consecutive days. $\Delta^9$-THC was prepared from a solution at concentration of 50 mg/5 ml in ethanol, and suspended in an equivalent volume of DMSO by evaporating ethanol under N2 gas and diluted to 2 mg/ml in Tween 80 (10%), DMSO (20%), and saline (70%) as described by (Fan et al., 2010; Hoffman et al., 2007). RIM, Celebrex or NS398 were administered 30 min before $\Delta^9$-THC injection.

Cell Culture:

Primary hippocampal neurons (astroglial cells<2%), mixed neurons and astroglial cells (astroglial cells ~10%), astroglial cell-enriched (astroglial cells>95%) and NG108-15 cells were cultured as described previously (Sang et al, 2005; Zhang and Chen, 2008). The extent of neurons and astroglial cells in culture were controlled by different treatments, which was estimated by using immunostaining with NeuN, a neuronal marker, glial fibrillary acidic protein (GFAP), an astrocytic marker, and OX-42, a microglial marker, in conjunction with DAPI staining.

Hippocampal Slice Preparation:

Hippocampal slices were prepared from mice as described previously (Chen et al., 2002; Chen et al., 2012; Fan et al., 2010). Briefly, after decapitation, brains were rapidly removed and placed in cold oxygenated (95% $O_2$, 5% $CO_2$) artificial cerebrospinal fluid (ACSF) containing: 125.0 NaCl, 2.5 KCl, 1.0 $MgCl_2$, 25.0 $NaHCO_3$, 1.25 $NaH_2PO_4$, 2.0 $CaCl_2$, 25.0 glucose, 3 pyruvic acid, and 1 ascorbic acid. Slices were cut at a thickness of 350-400 μm and transferred to a holding chamber in an incubator containing ACSF at 36° C. for 0.5 to 1 hour, and maintained in an incubator containing oxygenated ACSF at room temperature (~22-24° C.) for >1.5 h before recordings. Slices were then transferred to a recording chamber where they were continuously perfused with 95% $O_2$, 5% $CO_2$-saturated standard ACSF at ~32-34° C. Individual pyramidal and dentate granule neurons were viewed with an upright microscope (Olympus BX51WI) fitted with a 60× water-immersion objective and differential interference contrast (DIC) optics.

Electrophysiological Recordings:

Field EPSP (fEPSP) recordings both at CA3-CA1 and perforant path synapses in response to stimuli at a frequency of 0.05 Hz were made using an Axoclamp-2B patch-clamp amplifier (Molecular Devices, CA) in bridge mode. Recording pipettes were pulled from borosilicate glass with a micropipette puller (Sutter Instrument), filled with artificial ACSF (2-4 MΩ). Hippocampal LTP at CA3-CA1 and perforant path synapses was induced by a theta-burst stimulation (TBS), consisting of a series of 10 bursts of 5 stimuli at 100 Hz (200 ms interburst interval, which was repeated three time (Fan et al., 2010; Hoffman et al., 2007; Chen et al., 2012). The input-output function was tested before recording of LTP, and the baseline stimulation strength was set to provide fEPSP with an amplitude of ~30% from the subthreshold maximum derived from the input-output function. Hippocampal LTD was induced by low-frequency stimulation (900 stimuli at 1 Hz for 15 min) at CA3-CA1 synapses.

Surface Biotinylation Assay:

Surface biotinylation assays were performed in hippocampal slices as described previously (Chen et al., 2006; Fan et al., 2010). Briefly, hippocampal slices were cut at thickness of 400 μm using a vibratome from mice that received vehicle or $\Delta^9$-THC for 7 consecutive days, and then transferred to a six-well plate and incubated on ice for 1 h in carbogenated ACSF containing 500 μM Sulfo-NHS-SS-biotin (Thermo-Pierce, Rockford, Ill.). Collected tissue was then washed three times for 5 min with ice-cold ACSF containing 10 mM glycine, and was immediately homogenized in 800 μL ice-cold lysis buffer containing 20 mM Tris-HCl, pH 7.5, 1% Triton X-100, 50 mM NaCl, 1 mM EDTA, 0.1% sodium dodecyl sulfate, and a cocktail of protease inhibitors (Sigma, St. Louis, Mo.). After incubation on ice for 30 min, the homogenate was centrifuged at 18000 g at 4° C. for 10 min. Supernatants were collected. The biotinylated proteins from 300 μg of total protein in the lysate were precipitated with 60 μL of Ultra-link immobilized Streptavidin beads (Thermo-Pierce, Rockford, Ill.), diluted with the addition of 800 μL lysis buffer, on a rotator overnight at 4° C. Precipitates were collected by centrifuging at 3500 g for 1 min, washed by lysis buffer for three times, and then boiled for 5 min in 30 μL 2× sample buffer. 30 μg tissue lysates were used as controls for the total protein.

Western Blots:

Western blot assay was conducted to determine expression of COX-1, COX-2, glutamate receptor subunits (GluA1, GluN2A and GluN2B), PSD-95, G-protein subunits (Gβ1, Gγ2, Gαi1, Gαi2, Gαi3), phosphoproteins (Akt, ERK, p38MAPK, NF-κB), BACE1 and neprilysin in the hippocampal tissue from mice treated with vehicle or $\Delta^9$-THC or in cultures as described previously (Du et al., 2011; Fan et al., 2010; Zhang and Chen, 2008). Hippocampal tissue was extracted and immediately homogenized in RIPA lysis buffer and protease inhibitors, and incubated on ice for 30 min, then centrifuged for 10 min at 10,000 rpm at 4° C. Supernatants were fractionated on 4-15% SDS-PAGE gels (Bio-Rad) and transferred onto PVDF membranes (Bio-Rad). The membrane was incubated with specific antibodies (Table S1) at 4° C. overnight. The blots were washed and incubated with a secondary antibody (goat anti-rabbit 1:2,000, Life tech) at room temperature for 1 hr. Proteins were visualized by enhanced chemiluminescence (ECL, Amersham Biosciences, UK). The densities of specific bands were quantified by densitometry using FUJIFILM Multi Gauge software (version 3.0). Band densities were normalized to the total amount of protein loaded in each well as determined by mouse anti β-actin (1:4000, Sigma) as described previously (Du et al., 2011; Fan et al., Zhang and Chen, 2008; Chen et al., 2012).

Plasmid and Lentiviral Transfection, shRNA, and shRNA Knockdown Rescue:

NG108-15 cells were transfected with pcDNA3.1 plasmids encoding Gβ1 and Gγ2 subunits (provided by Dr. Xin-Yun Huang at Weill Medical College of Cornell University) or the pLL3.7 vector (expressing Gβ1 and Gγ2 shRNA as described previously, Sang et al., 2005). The cDNA3.1 plasmid carried with a GFP reporter gene was used as a negative control and to estimate the percentage of the transfection rate. COX-2 mRNA in NG105-15 cells was detected 6 hrs after treatment of $\Delta^9$-THC. To knockdown Gβ1 and Gγ2, the pLL3.7 vector (Addgene, Cambridge, Mass.) expressing scramble or Gβ1 and Gγ2 shRNA was used. Scramble oligos:

(SEQ ID No. 1)
5'AGCCTCGAGTACCTATACTAC3'

Gβ1 (NM_008142.4) shRNA oligos:

(SEQ ID No. 2)
5'CCACATTTACTGGACACACTG3', and Gγ2 (NM_010315.4) shRNA oligos:

(SEQ ID No. 3)
5'GCCAACATCGACAGGATAAAG3' were used for the shRNA experiment in NG108-15 cells. To determine the role of the Gαi subunit in mediating the 2-AG-produced COX-2 suppressive effect, the pLL3.7 lentiviral vector (Addgene) was used to insert shRNA-Gαi1, Gαi2 or Gαi3 driven by the U6 promoter and GFP reporter gene driven by the CMV promoter. shRNA oligos against Gαi1 (NM_010305.1), Gαi2 (NM_008138.4) or Gαi3 (NM_010306.2) were designed using the web-based software (ImgeneX) and submitted to BLAST-search. Scramble oligos:

5'AGACCAATACGTACAGACGGA3', shRNA-Gαi1
(SEQ ID No. 4):

5'GAGGAGTGTAAGCAGTACAAG3', shRNA-Gαi2
(SEQ ID No. 5):

5'AATGATCGACAAGAACCTGCG3', and shRNA-Gαi3
(SEQ ID No. 6):

5'CTAGCAGGCGTGATTAAACGT3' (SEQ ID No. 7).

To determine the off-target effects of shRNA knockdown, we used a knockdown rescue strategy to rescue Gαi1 and Gβ2 (Feng et al., 2010). The PCR-based mutagenesis method was used to generate shRNA-resistant cDNA constructs using the following primers with four point mutations in the shRNA targeting sequence without altering the encoded amino acids. The primers for the Gαi1 shRNA resistant construct:

5'GGGCTAGCGCCACCATGGGCTGCACATTGAGCGCTG3', (SEQ ID No. 8)

5'CTTATATTGTTTGCACTCCTCTTCCGAGTAGCCGGCTTCGTGG3', (SEQ ID No. 9)

5'GAGGAGTGCAAACAATATAAGGCAGTGGTCTACAGCAACACTA3', (SEQ ID No. 10)

and

5'GGGACCGGTGAAGAGACCACAGTCTTTTAG3'; (SEQ ID No. 11)

The primers for the Gβ2 shRNA resistant construct:

5'GGGCTAGCGCCACCATGAGTGAACTTGACCAGCTG3', (SEQ ID No. 12)

5'CAGTATGCCCGGTGAATGTGGTTGTCTGCTGGCCAGTCTCGA3', (SEQ ID No. 13)

5'CCACATTCACCGGGCATACTGGAGATGTCATGAGCCTGTCTC3', (SEQ ID No. 14)

and

5'GGGACCGGTGTTCCAGATCTTGAGGAAGCTG3'. (SEQ ID No. 15)

PCR products of Gαi1 and Gβ1 shRNA-resistant cDNAs were then cloned into the NheI-AgeI sites in the pLL3.7 shRNA vector. Gγ2 shRNA-resistant cDNA construct was created to rescue Gγ2 knockdown by annealing the following pair of primers into the NheI-AgeI sites in the pLL3.7 shRNA vector:

(SEQ ID No. 16)
5'CTAGCGCCACCATGGCCAGCAACAACACCGCCAGCATAGCACAAGCCAG

GAAGCTGGTAGAACAGCTGAAGATGGAAGCCAATATAGATAGAATAAAGGT

GTCCAAGGCAGCTGCTGACTTGATGGCCTACTGTGAGGCACATGCCAAGGA

AGACCCTCTGCTGACCCCAGTCCCAGCCTCAGAAAACCCCTTTCGGGAGAA

GAAGTTCTTCTGCGCCATCCTTA3' and (SEQ ID No. 17)
5'CCGGtAAGGATGGCGCAGAAGAACTTCTTCTCCCGAAAGGGGTTTTCTG

AGGCTGGGACTGGGGTCAGCAGAGGGTCTTCCTTGGCATGTGCCTCACAGT

AGGCCATCAAGTCAGCAGCTGCCTTGGACACCTTTATTCTATCTATATTGG

CTTCCATCTTCAGCTGTTCTACCAGCTTCCTGGCTTGTGCTATGCTGGCGG

TGTTGTTGCTGGCCATGGTGGCG3'.

All plasmids were sequenced to verify their construction. psPAX2 and PMD2.G vectors were used for viral envelope and production. pLL3.7 lentivirus (LV) were generated and packaged in 293T cells and titered ($1 \times 10^8$) by fluorescence-activated cell sorter (FACS) analysis using flow cytometry. Mixed culture of neurons and astroglial cells were treated with LV-shRNA-Gαi over night at DIV 8. Phospho-Akt, ERK44/42, p38MAPK, and NF-κB were detected 4 hrs and COX-2 protein was analyzed 16 hrs after application of LPS, 2-AG, or $\Delta^9$-THC at DIV 14.

Reverse Transcription and Real-Time PCR:

Total RNA was prepared from harvested tissue or cells with the RNeasy Mini Kit (Qiagen) and treated with RNase-free DNase (Qiagen) according to the manufacturer's instructions. The RNA concentration was measured by spectrophotometer (DU 640; BECKMAN). RNA integrity was verified by electrophoresis in a 1% agarose gel.

The iscript cDNA synthesis kit (BioRad) was used for the reverse transcription reaction. We used 1 μg total RNA, with 4 μl 5× iscript reaction mix and 1 μl iscript reverse transcriptase. The total volume was 20 μl. Samples were incubated for 5 min at 25° C. All samples were then heated to 42° C. for 30 min, and reactions were stopped by heating to 85° C. for 5 min. Real-time RT-PCR specific primers for the COX-2 receptor, β1, γ2, and GAPDH were selected using Beacon Designer Software (BioRad) and synthesized by IDT (Coralville, Iowa). They are listed as follows: Name: forward primer, reverse primer (amplicon size), genebank accession number: COX-2:

5'AAGCGAGGACCTGGGTTCAC3', (SEQ ID No. 18)

5'ACACCTCTCCACCAATGACCTG3' (SEQ ID No. 19)

(142 bp), BC052900; β1:

5'GACCTACTCCCATGACAACATT3', (SEQ ID No. 20)

5'TGAGTGCATCCCAGACATTAC3' (SEQ ID No. 21)

(116 bp), NM 008142.4; γ2:

5'AGCCAACATCGACAGGATAAA3', (SEQ ID No. 22)

5'TAAAGGATGGCGCAGAAGAA3' (SEQ ID No. 23)

(150 bp), NM_010315.4; GAPDH:

5'ACCACAGTCCATGCCATCAC3', (SEQ ID No. 24)

5'ACCTTGCCCACAGCCTTG3' (SEQ ID No. 25)

(134 bp), M32599. The PCR amplification of each product was further assessed using 10-fold dilutions of mouse brain cDNA library as a template and was found to be linear over five orders of magnitude and at greater than 95% efficiency.

All the PCR products were verified by sequencing. The reactions were set up in duplicate in total volumes of 25 µl containing 12.5 µl 2× iQSYBR green Supermix (BioRad) and 5 µl template (1:10 dilution from RT product) with a final concentration of 400 nM of the primer. The PCR cycle was as follows: 95° C./3 min, 45 cycles of 95° C./30 sec, 58° C./45 sec and 95° C./1 min, and the melt-curve analysis was performed at the end of each experiment to verify that a single product per primer pair was amplified. Furthermore, the sizes of the amplified DNA fragments were verified by gel electrophoresis on a 3% agarose gel. The amplification and analysis were performed using an iCycler iQ Multicolor Real-Time PCR Detection System (BioRad). Samples were compared using the relative CT method. The fold increase or decrease was determined relative to a vehicle-treated control after normalizing to a housekeeping gene using $2^{-\Delta\Delta CT}$, where $\Delta CT$ is (gene of interest CT)−(GAPDH CT), and $\Delta\Delta CT$ is ($\Delta CT$ treated)−($\Delta CT$ control), as described previously (Chen et al., 2006a; 2012; Sang et al., 2005; Zhang & Chen, 2008).

CHIP Analysis:

Chromatin Immunoprecipitation (ChIP) analysis was performed to determine the binding of NF-κB in the promoter of COX-2 gene (ptgs2) according to the manufacture's instruction (EMD Millipore). The potential NF-κB binding site(s) in the promoter region was identified using the TFSEARCH (http://www.cbrc.jp/research/db/TF-SEARCH.html). PCR amplification was performed with specific primers: forward primer:

(SEQ ID No. 26)
5'CTGTGTGCGTGCTCTGA3' and reverse primer:

(SEQ ID No. 27)
5'TCAAGAGTGTCACAGCTTCC3' to detect the interaction between p65 and the promoter region of ptgs2. $\Delta^9$-THC (30 µM) increased binding of p65 to the binding site at −419 to −428 of the ptgs2 promoter positions in mixed culture of neurons and astroglial cells and this increase was attenuated by SC-514 (100 µM), an IKKβ specific inhibitor.

PGE$_2$ Assay:

PGE$_2$ in hippocampal tissue from WT and COX-2 KO mice that received $\Delta^9$-THC, CP55,940, $\Delta^9$-THC+Celebrex, or CP55,940+NS398 was detected using PGE$_2$ enzyme immunoassay kit (Cayman Chemical, Ann Arbor, Mich.) according to the procedure described by the manufacturer (Zhang and Chen, 2008).

Immunohistochemistry:

Immunohistochemical analyses were performed to determine total Aβ in coronal brain sections as described previously (Chen et al., 2012). 5XFAD APP transgenic mice that vehicle, or $\Delta^9$-THC (3 mg/kg) or $\Delta^9$-THC+Celebrex (1 mg/kg) for 4 weeks at 4 to 6 months of age were anesthetized with ketamine/Xylazine (200/10 mg/kg) and subsequently transcardially perfused with PBS followed by 4% paraformaldehyde in phosphate buffer. The brains were quickly removed from the skulls and fixed in 4% paraformaldehyde overnight, and then transferred into the PBS containing 30% sucrose until sinking to the bottom of the small glass jars. Cryostat sectioning was made on a freezing Vibratome at 40 µm and series sections (10 to 12 slices) were collected in 0.1M phosphate buffer. Free floating sections were immunostained using the antibody specific for total Aβ followed by incubation with the corresponding fluorescent-labeled secondary antibody. 4'-6-Diamidino-2-phenylindole (DAPI), a fluorescent stain that binds strongly to DNA, was used it to detect cell nuclei in the sections. The sections were then mounted on slides for immunofluorescence detection using a Zeiss fluorescence microscope.

Expression of synaptic and extrasynaptic GluA1, GluN2A, and GluN2B was determined using immunostaining analysis as described previously with modifications (Clapp et al., 2010; Chen et al., 2012; Li et al., 2011; Sang et al., 2005). Cryostat sagittal sectioning was made in C57BL/6 mice that received vehicle, $\Delta^9$-THC, NS398 or NS398+$\Delta^9$-THC. Free floating sections were immunostained using specific antibodies GluA1 (1:500, Lifespan Bios), Glu2A (1:500, Lifespan Bios), GluN2B (1:200, Lifespan Bios), and synaptophysin (Syn, 1:100, EMD Millipore) followed by incubation with the corresponding fluorescent-labeled secondary antibody. Penetration of immunolabeling through the entire sampled 3 µm depth was examined. A Zeiss deconvolution microscope with a 63× oil-immersion objective (NA=1.4) was used and z-stack images were collected through 3 µm (0.5 µm steps) from evenly spaced sections. For each section, two to three z-stacks were collected from the target field. z-Stacks were deconvoluted and analyzed using the SlideBook 5.5 software (Intelligent Imaging Innovations, Inc. Denver, Colo.). The clusters detected with the subunit GluA1, GluN2A, or GluN2B immunoreactivity colocalized with Syn represent synaptic glutamate receptors, while noncolocalized with Syn represent extrasynaptic receptors.

Histochemistry:

Degenerated neurons were detected using Fluoro-Jade C (FJC), which is an anionic dye that specifically stains the soma and neurites of degenerating neurons and thus is unique as a neurodegenerative marker. Cryostat cut sections were incubated in the solution with FJC (0.0001% solution, EMD Millipore) and DAPI (0.5 µg/ml) for 10 min, followed by 3×1-min wash with distilled water. Slices were dried naturally at room temperature without light. The images were taken using a Zeiss deconvolution microscope with SlideBook 5.0 software as described previously (Chen et al., 2012).

Two-Photon Imaging:

Morphology of dendritic spines in hippocampal CA1 pyramidal neurons was determined in GFP-expressing transgenic mice treated with vehicle, $\Delta^9$-THC or NS398+$\Delta^9$-THC using a two-photon laser scanning microscope (Chameleon hands-free ultrafast Ti: sapphire laser with an Olympus scan head) with Olympus FLUOVIEW 300 software (Chen et al., 2012). Shape (thin, mushroom, or stubby), size, density, and volume of spines were measured from the three-dimensional reconstructions (Z stacks: 1µ step for the whole cell and 0.1µ step for a segment of dendrites) using AutoQuant X2 or 3D deconvolution plugin of Image J (http://bigwww.epfl.ch/algorithms/deconvolutionlab) and NeuronStudio (for 3D reconstruction of imaged dendritic spines, Version 0.9.92; http://research.mssm.edu/cnic/tools-ns.html, CNIC, Mount Sinai School of Medicine). Spine densities were estimated by counting the number of spines along 100 to 150 µm (CA1) segments of dendrites in hippocampal neurons. The following parameters were used in analyzing and quantifying spines using NeuronStudio: Voxel size was set as 0.029*0.029*0.3 µm. For neuritic tracing, attach ratio was set at 1.3 and discretization at 1.0. Minimal length was set as 3 um (Dumitriu et al., 2011; LaPlant et al., 2010). Dynamic and scattered sampling options were chosen. Erroneous detection is manually corrected. For spine detection and classification, spines with length 0.2-3 um and width below 3 um were detained. Spines with minimal head diameter of 0.35 um and head/neck ration 1.1 were classified as mushroom spines. Minimal length/head ratio 2.5 was for thin and non-thin spines classification. The other spines were defined as stubby. Voxel threshold were set at 160 voxels (~0.08 µm$^3$) for stubby spines and 80 voxels (~0.04 µm$^3$) for non-stubby spines, respectively. Very obviously erroneous detections were manually corrected and so spine detection and classification were nearly automatically carried out (Rodriguez et al., 2006).

Behavioral Tests:

The classic Morris water maze test was used to determine spatial memory as described previously (Chen et al., 2012). A circular water tank (diameter 120 cm and 75 cm in high) was filled with water and the water was made opaque with non-toxic white paint. A round platform (diameter 15 cm) was hidden 1 cm beneath the surface of the water at the center of a given quadrant of the water tank. COX-2 KO and WT mice received training in the Morris water maze for 5 days without any treatments (naïve). Animals that failed to find the platform hidden 1 cm beneath the surface of the water during the 5 days of training were excluded from the experiments. For each trial, the mouse was released from the wall of the tank and allowed to search, find, and stand on the platform for 10 seconds within the 60-second trial period. For each training session, the starting quadrant and sequence of the four quadrants from where the mouse was released into the water tank were randomly chosen so that it was different among the separate sessions for each animal and was different for individual animals. Starting at day 6, WT animals received vehicle, $\Delta^9$-THC (10 mg/kg), NS398 (10 mg/kg), $\Delta^9$-THC+NS398 once a day for 7 days. COX-2 KO mice received vehicle or $\Delta^9$-THC (10 mg/kg) for 7 days. NS398 was administered 30 min prior to $\Delta^9$-THC injection. Tests were performed 30 min following the injections. Training was carried out continuous 7 days (7 sessions) and each session consisted of 4 trials. A probe trail test was conducted 24 hrs after the cessation of the last $\Delta^9$-THC injection. During the probe test, the platform was removed from the pool, and the task performances were recorded for 60 seconds by a video-camera and the task performances, including swimming paths, speed, and time spent in each quadrant using an EthoVision video tracking system (Noldus). The time spent in each quadrant was analyzed.

Hippocampus-dependent contextual memory was determined using a fear-conditioning working-station (Coulbourn Instruments, Allentown, Pa.) and a one-trial protocol as describe previously (Chen et al., 2006a; 2006b). Mice were individually put into the shock chamber and allowed to freely explore the environment for 150 seconds. Immediately after this, a tone at 90 dB and 2,800 Hz (CS) was delivered for 30 seconds, and at the last 2 seconds a foot shock at 0.8 mA was delivered to the mice for 2 seconds (US). After the pairing of CS/US, mice were allowed to stay in the chamber for another 30 seconds and then returned to their home cages. Then the animals started receiving vehicle, $\Delta^9$-THC (10 mg/kg), NS398 (10 mg/kg), $\Delta^9$-THC+NS398 once a day for 7 days. Fear memory test was conducted 24 hours after the cessation of the last injections. For contextual conditioning, mice were individually put back into the chamber where they received the shock and the freezing response was recorded for 5 minutes with a sampling method at an interval of 5 seconds. The freezing behavioral response derived from the freezing scores was summed over the 5-min test period.

The 'open field' test was conducted using an automatic-recording open-field working station (MED Associates, Georgia, Vt.). During the test, mice were individually released into the center of the box immediately after injections of $\Delta^9$-THC, NS398, $\Delta^9$-THC+NS398, Celebrex or Celebrex+$\Delta^9$-THC. Celebrex and NS398 were injected 30 min prior to $\Delta^9$-THC injection and allowed to explore the field for 30 min and their behaviors were recorded by a photobeam-scanning system and a video camera simultaneously. Data were analyzed automatically by the computer-sampling system.

The cataleptic effect of $\Delta^9$-THC was detected using the bar test as described previously with modification (Egashira et al., 2007; Pertwee and Wickens, 1991). Briefly, the front paws of each mouse were placed on an elevated rod (0.5 cm in diameter and 3.5 cm from the bottom of the test box) and the duration of time that the mouse kept motionless was determined. The test was conducted 30, 60, and 90 min after $\Delta^9$-THC injection. Celebrex was injected 30 min prior to $\Delta^9$-THC injection.

Data Analysis:

Data are presented as mean±S.E.M. Unless stated otherwise, one- and two-way ANOVA followed by Fisher's PLSD or Bonferronni post-hoc tests were used for statistical comparison when appropriate. Differences were considered significant when $P<0.05$.

REFERENCES FOR ADDITIONAL INFORMATION FOR EXAMPLE 1

Clapp P, Gibson ES, Dell'acqua ML, Hoffman PL. (2010). Phosphorylation regulates removal of synaptic N-methyl-D-aspartate receptors after withdrawal from chronic ethanol exposure. J. Pharmacol. Exp. Ther. 332, 720-729.

Chen, C., Magee, J. C., and Bazan, N. G. (2002). Cyclooxygenase-2 regulates prostaglandin E$_2$ signaling in hippocampal long-term synaptic plasticity. J. Neurophysiol. 87, 2851-2857.

Chen, C., Hardy, M., Zhang, J., LaHoste, G. J. and Bazan, N. G. (2006a). Altered NMDA receptor trafficking contributes to sleep deprivation-induced hippocampal synaptic and cognitive impairments. Biochem. Biophys. Res. Comm. 340, 435-440.

Chen, Q., Nakajima, A., Meacham, C. & Tang, Y. P. (2006b). Elevated cholecystokininergic tone constitutes an important molecular/neuronal mechanism for the expression of anxiety in the mouse. Proc. Natl. Acad. Sci. U.S.A. 103, 3881-3886.

Chen, R., Zhang, J., Wu, Y., Wang, D., Feng, G., Tang, Y. P., Teng, Z., and Chen, C. (2012). Monoacylglycerol lipase is a therapeutic target for Alzheimer's disease. Cell Reports 2, 1329-1339.

Dumitriu D, Rodriguez A, Morrison J H. (2011). High-throughput, detailed, cell-specific neuroanatomy of dendritic spines using microinjection and confocal microscopy. Nat Protoc. 6, 1391-1411.

Egashira, N., Koushi, E., Mishima, K., Iwasaki, K., Oishi, R., Fujiwara, M. (2007). 2,5-Dimethoxy-4-iodoamphetamine (DOI) inhibits Delta9-tetrahydrocannabinol-induced catalepsy-like immobilization in mice. J. Pharmacol. Sci. 105, 361-366.

Fan, N., Yang, H., Zhang, J., and Chen, C. (2010). Reduced expression of glutamate receptors and phosphorylation of CREB are responsible for in vivo $\Delta^9$-THC exposure-impaired hippocampal synaptic plasticity. J. Neurochem. 112, 691-702.

Feng, Y., Nie, L., Thakur, M. D., Su, Q., Chi, Z., Zhao, Y., and Longmore, G. D. (2010). A multifunctional lentiviral-based gene knockdown with concurrent rescue that controls for off-target effects of RNAi. Genomics Proteomics Bioinformatics 8, 238-245.

Hoffman, A. F., Oz. M., Yang, R., Lichtman, A. H., and Lupica, C. R. (2007). Opposing actions of chronic Delta9-tetrahydrocannabinol and cannabinoid antagonists on hippocampal long-term potentiation. Learn. Mem. 14, 63-74.

Li, S., Jin, M., Koeglsperger, T., Shepardson, N. E., Shankar, G. M., Selkoe, D. J. (2011). Soluble Aβ oligomers inhibit long-term potentiation through a mechanism involving excessive activation of extrasynaptic NR2B-containing NMDA receptors. J. Neurosci. 31, 6627-6638.

LaPlant Q, Vialou V, Covington HE 3rd, Dumitriu D, Feng J, Warren B L, Maze I, Dietz D M, Watts E L, Iñiguez S D, Koo J W, Mouzon E, Renthal W, Hollis F, Wang H, Noonan M A, Ren Y, Eisch A J, Bolaños C A, Kabbaj M, Xiao G, Neve R L, Hurd Y L, Oosting R S, Fan G, Morrison J H, Nestler E J. (2010). Dnmt3a regulates emotional behavior and spine plasticity in the nucleus accumbens. Nat Neurosci. 13, 1137-1143.

Oakley, H., Cole, S. L., Logan, S., Maus, E., Shao, P., Craft, J., Guillozet-Bongaarts, A., Ohno, M., Disterhoft, J., Van Eldik, L., Berry, R., and Vassar, R. (2006). Intraneuronal β-amyloid aggregates, neurodegeneration, and neuron loss in transgenic mice with five familial Alzheimer's disease mutations: potential factors in amyloid plaque formation. J. Neurosci. 26, 10129-10140.

Pertwee, R. G. & Wickens, A. P. (1991). Enhancement by chlordiazepoxide of catalepsy induced in rats by intravenous or intrapallidal injections of enantiomeric cannabinoids. Neuropharmacol 30, 237-244.

Rodriguez, A., Ehlenberger, D. B., Hof, P. R., Wearne, S. L. (2006). Rayburst sampling, an algorithm for automated three-dimensional shape analysis fromlaser scanning microscopy images. Nat. Protoc. 1, 2152-2161.

Sang, N., Zhang, J., Marcheselli, V., Bazan, N. G., and Chen, C. (2005). Postsynaptically synthesized prostaglandin E2 modulates hippocampal synaptic transmission via a pre-synaptic PGE2 EP2 receptor. J. Neurosci. 25, 9858-9870.

Zhang, J., and Chen, C. (2008). Endocannabinoid 2-arachidonoylglycerol protects neurons by limiting COX-2 elevation. J. Biol. Chem. 283, 22601-22611.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A method of treating a disease or condition consisting of: administering to a subject in need thereof, a therapeutically effective amount of a COX-2 inhibitor, or a pharmaceutically acceptable salt of the COX-2 inhibitor, and a therapeutically effective amount of a cannabinoid, or a pharmaceutically acceptable salt of the cannabinoid, to treat the disease or condition.

2. The method of claim 1, wherein administering includes administering to the subject a pharmaceutical composition including both: a therapeutically effective amount of a COX-2 inhibitor, or a pharmaceutically acceptable salt of the COX-2 inhibitor; and a therapeutically effective amount a cannabinoid, or a pharmaceutically acceptable salt of the cannabinoid.

3. The method of claim 2, wherein the cannabinoid is formulated in a delayed-release cannabinoid formulation.

4. The method of claim 1, wherein the cannabinoid is administered about 15 minutes or more after the initial administration of the COX-2 inhibitor.

5. The method of claim 1, wherein administering includes:
   administering to the subject, a first pharmaceutical composition that includes a therapeutically effective amount of a COX-2 inhibitor, or a pharmaceutically acceptable salt of the COX-2 inhibitor and a pharmaceutically acceptable carrier, and
   administering to the subject a second pharmaceutical composition that includes a therapeutically effective amount of a cannabinoid, or a pharmaceutically acceptable salt of the cannabinoid, and a pharmaceutically acceptable carrier.

6. The method of claim 5, wherein the second pharmaceutical composition is delivered about 15 minutes after the first pharmaceutical composition.

7. The method of claim 1, wherein the COX-2 inhibitor is selected from the group consisting of: celecoxib, rofecoxib, meloxicam, piroxicam, deracoxib, parecoxib, valdecoxib, etoricoxib, a chromene derivative, a chroman derivative, N-(2-cyclohexyloxynitrophenyl)methane sulfonamide, COX189, ABT963, JTE-522, rofecoxib, valdecoxib, parecoxib, aspirin, acetaminophen, ibuprofen, flurbiprofen, ketoprofen, naproxen, oxaprozin, etodolac, indomethacin, ketorolac, lornoxicam, nabumetone, and diclofenac, as well as pharmaceutically acceptable salts of each, pharmaceutically acceptable derivatives of each, prodrugs of each.

8. The method of claim 1, wherein the cannabinoid is selected from the group consisting of: dronabinol, nabilone, cannabinol (CBN), tetrahydrocannabinol (THC), dimethyl heptylpentyl cannabidiol (DMHP-CBD), and a combination thereof.

9. The method of claim 1, wherein the COX-2 inhibitor is celecoxib or rofecoxib and the cannabinoid is dronabinol or nabilone.

10. The method of claim 1, wherein the disease or condition is selected from the group consisting of: Alzheimer's disease, Parkinson's disease, multiple sclerosis, epilepsy, traumatic brain injury, brain ischemia (stroke), arthritis, cancer, asthma, bronchitis asthma, bronchitis, inflammatory bowel disease, Crohn's disease, gastritis, irritable bowel syndrome, ulcerative colitis, migraine headaches, periarteritis *nodosa*, thyroiditis, aplastic anemia, Hodgkin's disease, sclerodma, rheumatic fever, type II diabetes, myasthenia gravis, amyotrophic lateral sclerosis, sacoidosis, nephrotic syndrome, Behchet's syndrome, polymyositis, gingivitis, peridontal disease, fibromyalgia, atopic dermatitis, insulitis, nausea, anorexia, pain, and post-traumatic stress disorder.

11. A method of reducing a side-effect of a cannabinoid administered to a patient, consisting of the step of administering to the patient receiving the cannabinoid a therapeutically effective amount of a COX-2 inhibitor or a pharmaceutically acceptable salt thereof.

12. The method of claim 11, wherein the COX-2 inhibitor or a pharmaceutically acceptable salt thereof and the cannabinoid or a pharmaceutically acceptable salt thereof are administered together in a single pharmaceutical composition.

13. The method of claim 11, wherein the cannabinoid is formulated in a delayed-release cannabinoid formulation.

14. The method of claim 11, wherein the cannabinoid is administered about 15 minutes or more after the initial administration of the COX-2 inhibitor.

15. The method of claim 11, wherein administering includes:
   administering to the subject, a first pharmaceutical composition that includes a therapeutically effective amount of a COX-2 inhibitor or a pharmaceutically acceptable salt thereof and a pharmaceutically acceptable carrier, and
   administering to the subject a second pharmaceutical composition that includes a therapeutically effective amount of a cannabinoid or a pharmaceutically acceptable salt thereof and a pharmaceutically acceptable carrier.

16. The method of claim 11, wherein the COX-2 inhibitor is selected from the group consisting of: celecoxib, rofecoxib, meloxicam, piroxicam, deracoxib, parecoxib, valdecoxib, etoricoxib, a chromene derivative, a chroman derivative, N-(2-cyclohexyloxynitrophenyl)methane sulfonamide, COX189, ABT963, JTE-522, rofecoxib, valdecoxib, parecoxib, aspirin, acetaminophen, ibuprofen, flurbiprofen, ketoprofen, naproxen, oxaprozin, etodolac, indomethacin, ketorolac, lornoxicam, nabumetone, and diclofenac, as well as pharmaceutically acceptable salts of each, pharmaceutically acceptable derivatives of each, prodrugs of each.

17. The method of claim 16, wherein the cannabinoid is selected from the group consisting of: dronabinol, nabilone, cannabinol (CBN), tetrahydrocannabinol (THC), dimethyl heptylpentyl cannabidiol (DMHP-CBD), and a combination thereof.

18. The method of claim 11, wherein the COX-2 inhibitor is celecoxib or rofecoxib and the cannabinoid is dronabinol or nabilone.

* * * * *

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Scramble oligo

<400> SEQUENCE: 1
agcctcgagt acctatacta c                                              21

<210> SEQ ID NO 2
<211> LENGTH: 21
<212> TYPE: DNA
<213> ORGANISM: Artificial Sequence
<220> FEATURE:
<223> OTHER INFORMATION: Gbeta1 shRNA (NM_008142.4)

<400> SEQUENCE: 2
ccacatttac tggacacact g                                              21

<210> SEQ ID NO 3
<211> LENGTH: 21
<212> TYPE: DNA
<213> ORGANISM: Artificial Sequence
<220> FEATURE:
<223> OTHER INFORMATION: Ggamma2 shRNA (NM_010315.4)

<400> SEQUENCE: 3

```
gccaacatcg acaggataaa g                                              21

<210> SEQ ID NO 4
<211> LENGTH: 20
<212> TYPE: DNA
<213> ORGANISM: Artificial Sequence
<220> FEATURE:
<223> OTHER INFORMATION: Galphai Scramble shRNA

<400> SEQUENCE: 4
gaccaatacg tacagacgga                                                20

<210> SEQ ID NO 5
<211> LENGTH: 21
<212> TYPE: DNA
<213> ORGANISM: Artificial Sequence
<220> FEATURE:
<223> OTHER INFORMATION: Galphai1 shRNA

<400> SEQUENCE: 5
gaggagtgta agcagtacaa g                                              21

<210> SEQ ID NO 6
<211> LENGTH: 21
<212> TYPE: DNA
<213> ORGANISM: Artificial Sequence
<220> FEATURE:
<223> OTHER INFORMATION: Galphai2

<400> SEQUENCE: 6
aatgatcgac aagaacctgc g                                              21

<210> SEQ ID NO 7
<211> LENGTH: 21
<212> TYPE: DNA
<213> ORGANISM: Artificial Sequence
<220> FEATURE:
<223> OTHER INFORMATION: Galphai3

<400> SEQUENCE: 7
ctagcaggcg tgattaaacg t                                              21

<210> SEQ ID NO 8
<211> LENGTH: 36
<212> TYPE: DNA
<213> ORGANISM: Artificial Sequence
<220> FEATURE:
<223> OTHER INFORMATION: primer sequence for Galphai1 shRNA resistant
      construct

<400> SEQUENCE: 8
gggctagcgc caccatgggc tgcacattga gcgctg                              36

<210> SEQ ID NO 9
<211> LENGTH: 43
<212> TYPE: DNA
<213> ORGANISM: Artificial Sequence
<220> FEATURE:
<223> OTHER INFORMATION: Galphai1 shRNA

<400> SEQUENCE: 9
cttatattgt ttgcactcct cttccgagta gccggcttcg tgg                      43

<210> SEQ ID NO 10
<211> LENGTH: 43
<212> TYPE: DNA
```

```
<213> ORGANISM: Artificial Sequence
<220> FEATURE:
<223> OTHER INFORMATION: primer sequence for Galphai1 shRNA resistant
      construct

<400> SEQUENCE: 10
gaggagtgca aacaatataa ggcagtggtc tacagcaaca cta                    43

<210> SEQ ID NO 11
<211> LENGTH: 30
<212> TYPE: DNA
<213> ORGANISM: Artificial Sequence
<220> FEATURE:
<223> OTHER INFORMATION: primer sequence for Galphai1 shRNA resistant
      construct

<400> SEQUENCE: 11
gggaccggtg aagagaccac agtcttttag                                   30

<210> SEQ ID NO 12
<211> LENGTH: 35
<212> TYPE: DNA
<213> ORGANISM: Artificial Sequence
<220> FEATURE:
<223> OTHER INFORMATION: primer for the Gbeta2 shRNA resistant construct

<400> SEQUENCE: 12
gggctagcgc caccatgagt gaacttgacc agctg                             35

<210> SEQ ID NO 13
<211> LENGTH: 42
<212> TYPE: DNA
<213> ORGANISM: Artificial Sequence
<220> FEATURE:
<223> OTHER INFORMATION: primer for the Gbeta2 shRNA resistant construct

<400> SEQUENCE: 13
cagtatgccc ggtgaatgtg gttgtctgct ggccagtctc ga                     42

<210> SEQ ID NO 14
<211> LENGTH: 42
<212> TYPE: DNA
<213> ORGANISM: Artificial Sequence
<220> FEATURE:
<223> OTHER INFORMATION: primer for the Gbeta2 shRNA resistant construct

<400> SEQUENCE: 14
ccacattcac cgggcatact ggagatgtca tgagcctgtc tc                     42

<210> SEQ ID NO 15
<211> LENGTH: 31
<212> TYPE: DNA
<213> ORGANISM: Artificial Sequence
<220> FEATURE:
<223> OTHER INFORMATION: primer for the GBeta2 shRNA resistant construct

<400> SEQUENCE: 15
gggaccggtg ttccagatct tgaggaagct g                                 31

<210> SEQ ID NO 16
<211> LENGTH: 225
<212> TYPE: DNA
<213> ORGANISM: Artificial Sequence
<220> FEATURE:
<223> OTHER INFORMATION: primer

<400> SEQUENCE: 16
```

```
ctagcgccac catggccagc aacaacaccg ccagcatagc acaagccagg aagctggtag      60
aacagctgaa gatggaagcc aatatagata gaataaaggt gtccaaggca gctgctgact     120
tgatggccta ctgtgaggca catgccaagg aagaccctct gctgacccca gtcccagcct     180
cagaaaaccc ctttcgggag aagaagttct tctgcgccat cctta                     225

<210> SEQ ID NO 17
<211> LENGTH: 225
<212> TYPE: DNA
<213> ORGANISM: Artificial Sequence
<220> FEATURE:
<223> OTHER INFORMATION: primer

<400> SEQUENCE: 17
ccggtaagga tggcgcagaa gaacttcttc tcccgaaagg ggttttctga ggctgggact      60
ggggtcagca gagggtcttc cttggcatgt gcctcacagt aggccatcaa gtcagcagct     120
gccttggaca cctttattct atctatattg gcttccatct tcagctgttc taccagcttc     180
ctggcttgtg ctatgctggc ggtgttgttg ctggccatgg tggcg                     225

<210> SEQ ID NO 18
<211> LENGTH: 20
<212> TYPE: DNA
<213> ORGANISM: Artificial Sequence
<220> FEATURE:
<223> OTHER INFORMATION: COX-2 forward primer

<400> SEQUENCE: 18
aagcgaggac ctgggttcac                                                  20

<210> SEQ ID NO 19
<211> LENGTH: 22
<212> TYPE: DNA
<213> ORGANISM: Artificial Sequence
<220> FEATURE:
<223> OTHER INFORMATION: COX-2 reverse primer

<400> SEQUENCE: 19
acacctctcc accaatgacc tg                                               22

<210> SEQ ID NO 20
<211> LENGTH: 22
<212> TYPE: DNA
<213> ORGANISM: Artificial Sequence
<220> FEATURE:
<223> OTHER INFORMATION: Beta1 forward primer

<400> SEQUENCE: 20
gacctactcc catgacaaca tt                                               22

<210> SEQ ID NO 21
<211> LENGTH: 21
<212> TYPE: DNA
<213> ORGANISM: Artificial Sequence
<220> FEATURE:
<223> OTHER INFORMATION: Beta1 reverse primer

<400> SEQUENCE: 21
tgagtgcatc ccagacatta c                                                21

<210> SEQ ID NO 22
<211> LENGTH: 21
<212> TYPE: DNA
```

```
<213> ORGANISM: Artificial Sequence
<220> FEATURE:
<223> OTHER INFORMATION: gamma2 forward primer

<400> SEQUENCE: 22
agccaacatc gacaggataa a                                              21

<210> SEQ ID NO 23
<211> LENGTH: 20
<212> TYPE: DNA
<213> ORGANISM: Artificial Sequence
<220> FEATURE:
<223> OTHER INFORMATION: gamma 2 reverse primer

<400> SEQUENCE: 23
taaaggatgg cgcagaagaa                                                20

<210> SEQ ID NO 24
<211> LENGTH: 20
<212> TYPE: DNA
<213> ORGANISM: Artificial Sequence
<220> FEATURE:
<223> OTHER INFORMATION: NM_010315.4; GAPDH forward primer

<400> SEQUENCE: 24
accacagtcc atgccatcac                                                20

<210> SEQ ID NO 25
<211> LENGTH: 17
<212> TYPE: DNA
<213> ORGANISM: Artificial Sequence
<220> FEATURE:
<223> OTHER INFORMATION: GAPDH reverse primer

<400> SEQUENCE: 25
ccttgcccac agccttg                                                   17

<210> SEQ ID NO 26
<211> LENGTH: 17
<212> TYPE: DNA
<213> ORGANISM: Artificial Sequence
<220> FEATURE:
<223> OTHER INFORMATION: NF-kappaB binding site forward primer

<400> SEQUENCE: 26
ctgtgtgcgt gctctga                                                   17

<210> SEQ ID NO 27
<211> LENGTH: 20
<212> TYPE: DNA
<213> ORGANISM: Artificial Sequence
<220> FEATURE:
<223> OTHER INFORMATION: NF-kappaB binding site reverse primer

<400> SEQUENCE: 27
tcaagagtgt cacagcttcc                                                20
```